US011214799B2

(12) United States Patent
Kapczynski et al.

(10) Patent No.: US 11,214,799 B2
(45) Date of Patent: Jan. 4, 2022

(54) HA-SPECIFIC INFLUENZA VIRUS ATTENUATED VACCINE COMPRISING MUTATIONS IN SEGMENT 7, AND USES THEREFOR

(71) Applicants: The United States of America, as Represented by the Secretary of Agriculture, Washington, DC (US); The Roslin Institute, University of Edinburgh, Edinburgh (GB)

(72) Inventors: Darrell R. Kapczynski, Watkinsville, GA (US); Paul Digard, Edinburgh (GB); Lonneke Vervelde, Edinburgh (GB); David L. Suarez, Athens, GA (US)

(73) Assignee: THE UNIVERSITY COURT OF THE UNIVERSITY OF EDINBURG OLD COLLEGE, Edinburgh (GB)

( * ) Notice: Subject to any disclaimer, the term of this patent is extended or adjusted under 35 U.S.C. 154(b) by 0 days.

(21) Appl. No.: 16/814,286

(22) Filed: Mar. 10, 2020

(65) Prior Publication Data

US 2020/0291397 A1    Sep. 17, 2020

Related U.S. Application Data

(60) Provisional application No. 62/817,163, filed on Mar. 12, 2019.

(51) Int. Cl.

| | |
|---|---|
| *A61K 39/12* | (2006.01) |
| *A61K 48/00* | (2006.01) |
| *A01N 63/00* | (2020.01) |
| *A01N 65/00* | (2009.01) |
| *A61K 39/00* | (2006.01) |
| *C12N 15/11* | (2006.01) |
| *C12N 5/071* | (2010.01) |
| *A61K 39/145* | (2006.01) |

(52) U.S. Cl.
CPC ............ *C12N 15/11* (2013.01); *A61K 39/145* (2013.01); *C12N 5/0602* (2013.01); *C12N 2510/00* (2013.01); *C12N 2760/16034* (2013.01)

(58) Field of Classification Search
CPC ...... A61K 39/12; A61K 39/00; C07K 14/005; A61P 43/00; C12N 7/00
See application file for complete search history.

(56) References Cited

U.S. PATENT DOCUMENTS

| | | |
|---|---|---|
| 9,284,533 B2 | 3/2016 | Bilsel et al. |
| 9,919,042 B2 | 3/2018 | Bilsel et al. |
| 10,119,124 B2 | 11/2018 | Watanabe et al. |
| 10,130,697 B2 | 11/2018 | Watanabe et al. |

OTHER PUBLICATIONS

Wise et al., Identification of a novel splice variant form of the influenza A virus M2 ion channel with an antigenically distinct ectodomain, PLoS Pathogens, 2012, vol. 8(11):1-14.*
Chiang, C., et al., 2008, "Mutations at Alternative 5" Splice Sites of M1 mRNA Negatively Affect Influenza A Virus Viability and Growth Rate," J. Virol. 82: 10873-10886.
Robb N.C., and Fodor E., 2012, "The Accumulation of Influenza A Virus Segment 7 Spliced mRNAs is Regulated by The NS1 Protein," J. Gen. Virol. 93:113-118.
Wise, H.M., et al., 2012, "Identification of a Novel Splice Variant Form of the Influenza A Virus M2 Ion Channel with an Antigenically Distinct Ectodomain," PLOS Pathogens 8(11): e1002998.
Vasin A.V., et al., 2014, "Molecular Mechanisms Enhancing the Proteome of Influenza A Viruses: An Overview of Recently Discovered Proteins," Virus Res. 185: 53-63.

* cited by examiner

*Primary Examiner* — Barry A Chestnut
(74) *Attorney, Agent, or Firm* — John Fado; Maria Restrepo-Hartwig

(57) ABSTRACT

The disclosure relates to mutant recombinant influenza virus gene segment 7 with at least one mutation that modulates expression of M2 and M42 polypeptide. Also disclosed are recombinant influenza viruses comprising the mutant influenza virus gene segment 7, compositions comprising the mutant recombinant influenza virus gene segment 7, use of such mutant recombinant influenza virus gene segment 7 and mutant recombinant Influenza viruses.

17 Claims, 18 Drawing Sheets

Specification includes a Sequence Listing.

FIG. 4

AGCAAAAGCAGGTAGATATTTAAAG [ATG] AGTCTTCTAACCGAGGTCGAAAC*GTACGTTCTCT
CTATCGTCCGTCAGGCCCCCTCAAAGCCGAGATCGCGCAGAGACTTGAAG [ATG] TCTTTGCA
GGGAAAAACACTGATCTT*GAGGTACTTATGGAATGGCTAAAGACAAGACCAATCCTGTCACCTC
TGACTAAGGGGATTTTAGGATTTGTATTTACGCTCACCGTGCCCAGTGAGCGAGGACTGCAGCG
TAGACGCTTTGTCCAAAATGCCCTCAATGGGAATGGGGATCCAAACAACATGGACAGAGCAGTC
AAGCTATACAGGAAGCTCAAAAGAGAAATAACATTCCATGGGGCAAAGGAAGTGGCACTCAGTT
ATTCAACTGGTGCACTTGCCAGTTGCATGGGCCTCATATACAACAGAATGGGGACTGTGACCAC
CGAAGTGGCATTTGGCCTGGTGTGCGCCACATGTGAGCAGATTGCTGATTCCCAGCACCGGTCC
CACAGACAGATGGTGACAACAATCAACCCACTAATCAGGCATGAGAATAGAATGGTACTAGCAA
GCACTACGGCTAAAGCCATGGAGCAAATGGCAGGGTCAAGTGAGCAAGCAGCAGAGGCTATGGA
GGTTGCTAGTCAGGCTAGACAGATGGTGCATGCAATGAGGACCATTGGGACTCATCCTAGTTCC
AGTGCTGGTCTAAGAGATGATCTTCTTGAAAATTTGCAGGCTTACCAGAAACGGATGGGAGTGC
AAATGCAGCGATTCAAGTGATCCTCTCATTATCGCAGCGAGTATCATTGGGATCTTGCACTTGA
TATTGTGGATTCTTGATCGTCTTTTCTTCAAATGCATTTATCGTCGCCTTAAATACGGTTTGAA
AAGAGGGCCTTCTACGGAAGGAGCGCCTGAGTCTATGAGGGAAGAATATCGGCAGGAACAGCAG
AGTGCTGTGGATGTTGACGATGTTCATTTGTCAACATAGAGCTGGAG [TAA] AAAACTACCTT
GTTTCTACT

FIG. 5

MSL<u>QGKTLILRL</u>TRNGWECKCSDSSDPLIIAASIIGILHLILWILDRLFFKCIYRRLKYGLKRGPSTEGAPESMREEYRQEQQSAVDVDDVHFVNIELE

FIG. 6

MSL<u>LTEVETL</u>TRNGWECKCSDSSDPLIIAASIIGILHLILWILDRLFFKCIYRRLKYGLKRGPSTEGAPESMREEYRQEQQSAVDVDDVHFVNIELE

HA-SPECIFIC INFLUENZA VIRUS ATTENUATED VACCINE COMPRISING MUTATIONS IN SEGMENT 7, AND USES THEREFOR

CROSS-REFERENCE TO RELATED APPLICATIONS

This application claims priority to U.S. Provisional Patent Application 62/894,179, filed Mar. 12, 2019, the content of which is expressly incorporated herein by reference in its entirety.

STATEMENT OF FEDERALLY FUNDED RESEARCH

The work described herein was performed with U.S. Government support from the National Institute of Food and Agriculture (NIFA) grant No. 2015-67015-22968, and the Agricultural Research Service (ARS). Additional support was provided by the United Kingdom Biotechnology and Biological Sciences Research Council (BBSRC) grant No. BB/M027163/1. The government has certain rights in this work.

FIELD OF THE INVENTION

The disclosure relates to mutant recombinant influenza virus gene segment 7 where expression of the M2 or M42 coding sequences is modulated. Also disclosed are recombinant influenza viruses comprising the mutant influenza virus gene segment 7, compositions comprising the mutant recombinant influenza virus gene segment 7, and use of such mutant recombinant influenza viruses and mutant recombinant influenza virus gene segment 7.

SEQUENCE LISTING

The instant application contains a Sequence Listing which has been submitted via EFS-Web as ASCII compliant text file format (.txt), and is hereby incorporated by reference in its entirety. The ASCII file was created on Mar. 10, 2020, is named SequenceListing, and has 50 kilobytes. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

BACKGROUND OF THE INVENTION

Influenza A viruses are genetically diverse pathogens that can infect various hosts including birds, swine, and humans. Vaccines and vaccination have emerged during the past three decades as essential tools in influenza control. Their use in poultry can increase resistance to infection, prevent illness and death, reduce virus replication and shed, and reduce virus transmission to birds and mammals, including humans. Historically, only killed influenza virus vaccines are used in animals due to the risk of reversion of the virus in the vaccine to an enhanced virulent state or recombination of the virus in the vaccine with other influenza viruses. In addition, highly pathogenic forms of the virus are not used as vaccines due to concerns over manufacturing issues such as the potential release from improper inactivation.

Recently, recombinant influenza virus vaccines have been licensed for use in poultry. These vaccines express a single key influenza immunogen, the hemagglutinin (HA) protein. The HA protein is responsible for attachment of the virus to host cells, thus immunity against this protein induces protection from influenza disease. Killed (inactivated) influenza virus vaccines only induce systemic antibodies against the virus, whereas a live replicating vaccine virus induces both antibodies and cellular immunity. Currently available recombinant vaccines only induce immunity against the HA protein.

Vaccines comprising isolated recombinant influenza viruses comprising a mutant gene 7 segment that expresses functional M1 protein and a mutant M2 protein with a deletion of the cytoplasmic tail and either lacking the transmembrane domain or having a mutated transmembrane domain have been described by Watanabe T., et al. (U.S. Pat. No. 10,130,697) Live attenuated influenza vaccines comprising a mutation in gene segment 7 resulting in the deletion of eleven amino acids from the C terminus of the M2 protein have been described by Watanabe T., et al. (U.S. Pat. No. 10,119,124). Influenza vaccines comprising gene segment 7 with two stop codons introduced at nucleotides 786 to 791, deletion of nucleotides 792 to 842, and a G to C substitution at nucleotide 52 of influenza A/hvPR8/34 (H1N1) is disclosed by Bilsel P., et al. (U.S. Pat. Nos. 9,284,533 and 9,919,042).

The immunity produced by live virus vaccines is generally more durable, more effective, and more cross-reactive than the immunity induced by inactivated vaccines. Also, live virus vaccines are less costly to produce than are inactivated virus vaccines. However, mutations in attenuated influenza virus vaccines are ill defined and reversion to wild-type virus is a concern. Thus, the need remains for a mutant Influenza A useful in the production of a live attenuated vaccines that induce mucosal immunity, systemic antibodies, and cellular immunity against all influenza proteins.

SUMMARY OF THE INVENTION

Provided herein are recombinant influenza virus gene segment 7 with mutations that modulate expression of M2 and/or M42 polypeptides, methods for preparing such recombinant mutant gene segments, recombinant influenza viruses comprising such mutant gene segments, vaccines comprising such recombinant influenza virus M gene segments, and methods of using the same.

In an embodiment, the invention relates to recombinant influenza virus gene segment 7 with at least one mutation that modulates expression of the M2 and/or M42 polypeptides. In some embodiments, the invention relates to recombinant influenza virus gene segment 7 with at least one mutation that modulates expression of the M2 polypeptide. In some embodiments, the invention relates to recombinant influenza virus gene segment 7 with at least one mutation that modulates expression of the M42 polypeptide.

In an embodiment, the invention relates to a recombinant influenza virus gene segment 7 with a single mutation of either G to C at a nucleotide corresponding to position 52 of the Influenza A/Chicken/Penn/1/1983 gene segment 7 (G52C) or a G to A at a nucleotide corresponding to position 145 of the Influenza A/Chicken/Penn/1/1983 gene segment 7 (G145A). In some embodiments, the invention relates to a recombinant influenza virus gene segment 7 with a G52C mutation. In some embodiments, the invention relates to a recombinant influenza virus gene segment 7 with a G145A mutation.

In an embodiment, the invention relates to a recombinant influenza virus gene segment 7 with a single mutation of a G to C at a nucleotide corresponding to position 52 of the Influenza A/Chicken/Penn/1/1983 gene segment 7 (G52C) or a single mutation of a G to A at a nucleotide corresponding to position 145 of the Influenza A/Chicken/Penn/1/1983 gene segment 7 (G145A). In some embodiments, the invention relates to a recombinant influenza virus gene segment 7 with a G52C mutation. In some embodiments, the invention relates to a recombinant influenza virus gene segment 7 with a G145A mutation.

In an embodiment, the invention relates to a vector comprising a recombinant influenza virus gene segment 7 with at least one mutation that modulates expression of the M2 and/or M42 polypeptides. In some embodiments, the invention relates to a vector comprising a recombinant influenza virus gene segment 7 with at least one mutation that results in a gene segment 7 that does not produce an M2 polypeptide. In some embodiments, the invention relates to recombinant influenza virus gene segment 7 with at least one mutation that results in a gene segment 7 that does not produce an M42 polypeptide.

In an embodiment, the invention relates to a recombinant influenza virus comprising a gene segment 7 with at least one mutation that modulates the expression of the M2 and/or M42 polypeptides. In an embodiment, the invention relates to a recombinant influenza virus comprising a gene 7 segment with at least one mutation that modulates expression of the M2 polypeptide and the M42 polypeptide. In an embodiment, the invention relates to a recombinant influenza virus comprising a gene segment 7 with at least one mutation that modulates expression of the M2 polypeptide and the M42 polypeptide.

In an embodiment, the invention relates to a recombinant influenza virus comprising a gene segment 7 having a single G52C mutation or a single G145A mutation. In some embodiments, the invention relates to a recombinant influenza virus comprising a gene segment 7 with a G52C mutation. In an embodiment, the invention relates to a recombinant influenza virus comprising a gene segment 7 with a G145A mutation.

In an embodiment, the invention relates to a cell comprising a recombinant mutant influenza virus gene 7 segment with at least one mutation that modulates expression of the M2 and/or M42 polypeptides. In an embodiment, the invention relates to a cell comprising a recombinant mutant influenza virus gene segment 7 with a single G52C mutation or a single G145A mutation. In some embodiments, the invention relates to a cell comprising a recombinant mutant influenza virus gene segment 7 with a single G52C mutation. In some embodiments, the invention relates to a cell comprising a recombinant mutant influenza virus gene segment 7 with a single G145A mutation.

In some embodiments, the cell comprising the recombinant mutant influenza virus gene segment 7 is selected from MDCK cells, Vero cells, CV-1 cells, LLcomk.2 cells, MDBK cells, BK-1 cells, Chinese Hamster Ovary cells, 293T cells, human embryonic kidney cells, avian embryonic fibroblasts, and in ovo.

In an embodiment, the invention relates to a composition comprising a recombinant mutant influenza virus gene segment 7 having at least one introduced mutation that modulates expression of the M2 and/or M42 polypeptides. In some embodiments, the recombinant influenza virus gene segment 7 is from an Influenza A virus.

In an embodiment, the invention relates to a composition comprising a recombinant mutant influenza virus gene segment 7 having a single mutation selected from G52C and G145A. In some embodiments, the invention relates to a composition comprising a recombinant mutant influenza virus gene segment 7 having a G52C mutation. In some embodiments, the invention relates to a composition comprising a recombinant mutant influenza virus gene segment 7 having a G145A mutation.

In some embodiments of the invention the composition comprising a recombinant influenza virus gene segment 7 having at least one introduced mutation that modulates expression of the M2 and/or M42 polypeptides further comprises an adjuvant. In some embodiments of the invention the composition comprising a recombinant influenza virus gene segment 7 having a G52C or a G145A further comprises an adjuvant.

In an embodiment, the invention relates to methods for preparing an influenza virus comprising a gene segment 7 having at least one introduced mutation that modulates expression of the M2 and/or M42 polypeptides.

In an embodiment, the invention relates to methods for preparing an influenza virus comprising a gene segment 7 having a single mutation of G52C or G145A. In some embodiments, the invention relates to methods for preparing a composition comprising a recombinant influenza virus comprising a gene segment 7 having a G52C mutation. In some embodiments, the invention relates to a composition comprising a recombinant influenza virus comprising a gene segment having a G145A mutation. In some embodiments, the recombinant influenza virus is an Influenza A virus.

In an embodiment, a composition comprising an influenza virus gene segment 7 having at least one introduced mutation that modulates expression of the M2 and/or M42 polypeptides elicits a detectable immune response after administration of the composition to a vertebrate. In an embodiment, a composition comprising an influenza virus gene segment 7 having a G52C or a G145A mutation elicits a detectable immune response after administration of the composition to a vertebrate. In some aspects of the invention the vertebrate is selected from the group consisting of birds, Canidae, Cetacea, Felidae, Mustelidae, Rodentia, Equidae, Bovidae, Suidae, and Primates. In some embodiments the vertebrate is a bird. In some embodiments, the bird is selected from the group consisting of water fowl, chickens, and turkeys. In some embodiments, the vertebrate is a mammal. In some embodiments, the mammal is selected from the group consisting of pigs, horses, whales, dolphins, and humans.

In an embodiment, the invention relates to a recombinant influenza vaccine comprising a gene 7 segment having at least one introduced mutation that modulates expression of the M2 and/or M42 polypeptides. In an embodiment, the invention relates to a recombinant influenza vaccine, comprising a gene segment 7 with a G52C mutation or a G145A mutation. In an embodiment, the invention relates to a recombinant live influenza vaccine, comprising a gene segment 7 with a G52C mutation. In an embodiment, the invention relates to a recombinant live influenza vaccine, comprising a gene segment 7 with a G145A mutation.

In an embodiment, the invention relates to a method for immunizing a subject comprising administering to the subject a composition comprising a recombinant influenza virus comprising a gene 7 segment having at least one introduced mutation that modulates expression of the M2 and/or M42 polypeptides. In an embodiment, the invention relates to a method for immunizing a subject comprising administering to the subject a composition comprising a recombinant influenza virus comprising a gene segment 7 with a G52C mutation. In an embodiment, the invention relates to a method for immunizing a subject comprising administering to the subject a composition comprising a recombinant influenza virus comprising a gene segment 7 with a G145A mutation.

In an embodiment, the invention relates to an immunogenic composition comprising a recombinant influenza virus comprising a PA viral gene segment, a PB1 viral gene segment, a PB2 viral gene segment, an HA viral gene segment, an NA viral gene segment, an NP viral gene segment, an NS viral gene segment, and an M viral gene segment, wherein the viral M gene segment having at least one introduced mutation as compared to the viral M gene segment of wild type Influenza A virus that modulates expression of the M2 and/or M42 polypeptides. In some embodiments, the M gene segment in the immunogenic composition expresses an M42 polypeptide but does not express an M2 polypeptide. In some embodiments, the M gene segment in the immunogenic composition expresses an M2 polypeptide but does not express an M42 polypeptide.

In an embodiment, the invention relates to an immunogenic composition comprising a recombinant influenza virus comprising a PA viral gene segment, a PB1 viral gene segment, a PB2 viral gene segment, an HA viral gene segment, an NA viral gene segment, an NP viral gene segment, an NS viral gene segment, and an M viral gene segment, wherein the viral M gene segment has a G52C mutation or a G145A mutation as compared to the viral M gene segment of wild type Influenza A virus. In some embodiments, the M gene segment in the immunogenic composition has a G52C mutation. In some embodiments, the M gene segment in the immunogenic composition has a G145A mutation. In some embodiments of the invention, the wild-type viral M gene segment has the nucleotide sequence as set forth in SEQ ID NO: 1.

BRIEF DESCRIPTION OF THE DRAWINGS

FIG. 4 depicts the complete nucleotide sequence of Influenza A/Chicken/Penn/1/1983 H5N2 Segment 7; GenBank: CY015074.1; set forth in SEQ ID NO: 1. Boxed are the initiation codons for M2 and M42, and the termination codon for both. The M2 intron sequence is underlined and the M42 intron sequence is in Italics. Asterisks (*) above the sequence indicate G52 and G145.

FIG. 5 depicts the amino acid sequence of the M42 polypeptide encoded by the influenza gene segment 7 with an introduced G52C mutation (set forth in SEQ ID NO: 2). Amino acids present in M42 but not M2 are underlined.

FIG. 6 depicts amino acid sequence of the M2 polypeptide encoded by the influenza gene segment 7 with an introduced G145A mutation (set forth in SEQ ID NO: 3). Amino acids present in M42 but not M2 are underlined.

FIG. 7A presents a photomicrograph of recombinant influenza virions expressing a wild-type gene segment 7. FIG. 7B to FIG. 7D present photomicrographs of recombinant influenza virions expressing gene segment 7 with a G52C mutation. FIG. 7E to FIG. 7G present photomicrographs of recombinant influenza virions expressing gene segment 7 with a G145A mutation. The white lines through the virions are used to measure the virions in nm. Virion measurements are indicated in each photomicrograph.

FIG. 9A presents results for chickens vaccinated with recombinant influenza A virus expressing wild-type gene segment 7. FIG. 9B presents results for chickens vaccinated with recombinant influenza A virus expressing gene segment 7 with G52C mutation. FIG. 9C presents results for chickens vaccinated with influenza A virus expressing gene segment 7 with G145A mutation. The Y axis shows the $Log_2$ of the Hemagglutination Inhibition (HI) titer.

FIG. 10A presents the virus titer in oral swabs one day post-vaccination. FIG. 10B presents the virus titer in oral swabs two days post-vaccination. FIG. 10C presents the virus titer in oral swabs three days post-vaccination. FIG. 10D presents the virus titer in oral swabs four days post-challenge. FIG. 10E presents the virus titer in oral swabs five days post-vaccination. FIG. 10F: virus titer in oral swab six days post-vaccination. The Y axis shows the $Log_{10}$ of the 50% embryo infectious dose ($log_{10}$ $EID_{50}$). (i) chickens vaccinated with recombinant influenza A virus comprising a wild-type gene segment 7; (ii) chickens vaccinated with recombinant influenza A virus comprising a gene segment 7 with G52C mutation; (iii) chickens vaccinated with recombinant influenza A virus comprising a gene segment 7 with G145A mutation; (iv) birds in contact with chickens vaccinated with recombinant influenza A virus comprising a wild-type gene segment 7; (v) birds in contact with chickens vaccinated with recombinant influenza A virus comprising a gene segment 7 with G52C mutation; (vi) birds in contact with chickens vaccinated with recombinant influenza A virus comprising a gene segment 7 with G145A mutation.

FIG. 11A: Challenge against homologous highly pathogenic avian influenza virus. FIG. 11B: Challenge against heterologous highly pathogenic avian influenza virus. The Y axis presents the percent survival. The X axis presents the days post challenge.

Figures 12A, 12B, 12C, 12D:
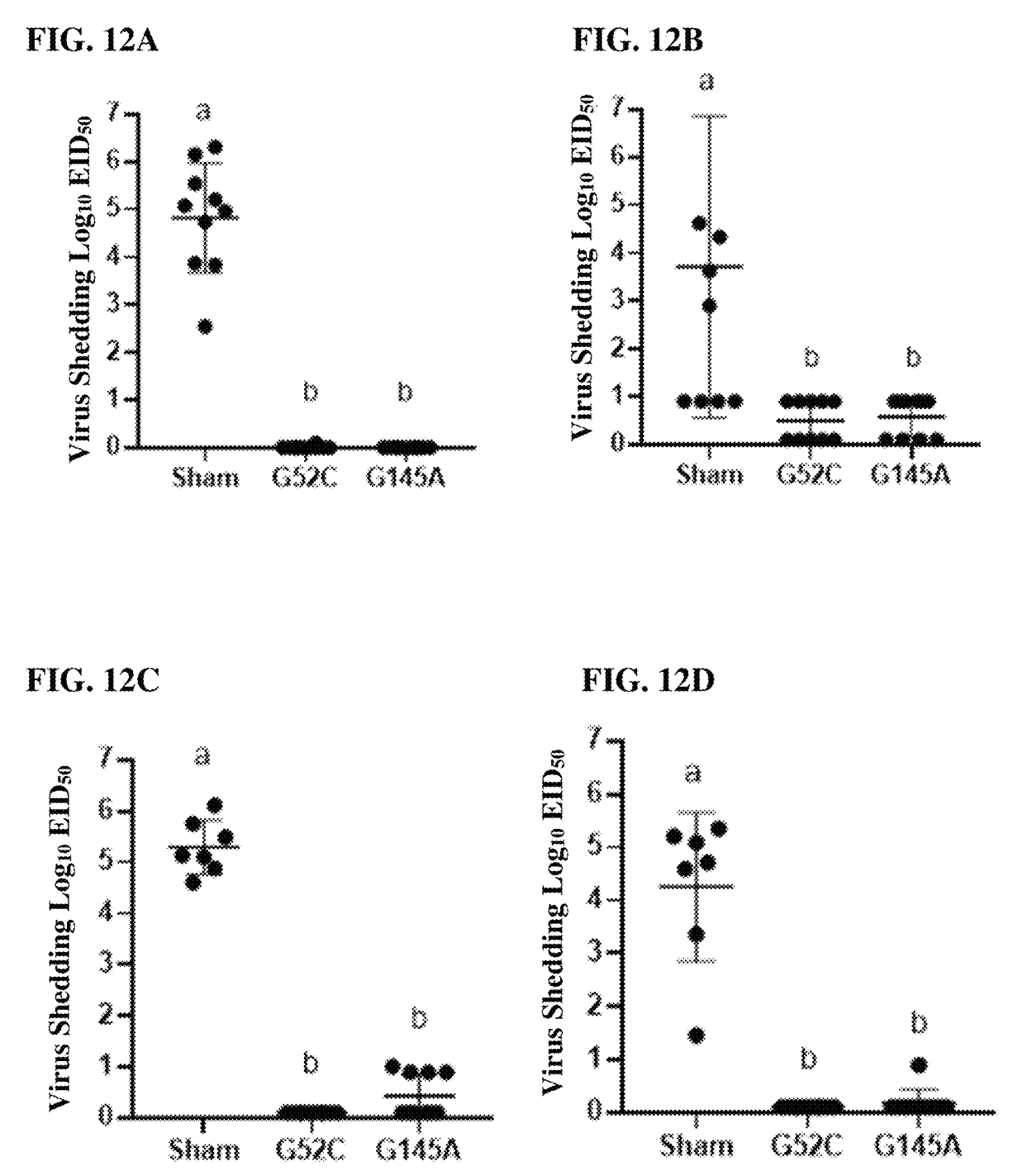

FIG. 12A to FIG. 12D depict graphs of virus shedding in chickens sham vaccinated (Sham); vaccinated with recombinant influenza A virus expressing M gene segment comprising G52C (G52C); or expressing M gene segment comprising G145A (G145A), challenged with A/Chicken/Penn/1370/1983 H5N2, a homologous highly pathogenic influenza A virus. FIG. 12A presents virus shedding in oral swabs 2 days post challenge. FIG. 12B presents virus shedding in cloacal swabs 2 days post challenge. FIG. 12C presents virus shedding in oral swabs 4 days post challenge. FIG. 12D presents virus shedding in cloacal swabs 4 days post challenge. The X axis shows the vaccine groups and the Y axis shows the $\log_{10}$ of the 50% embryo infectious dose ($\log_{10}$ $EID_{50}$).

Figures 13A, 13B, 13C, 13D:
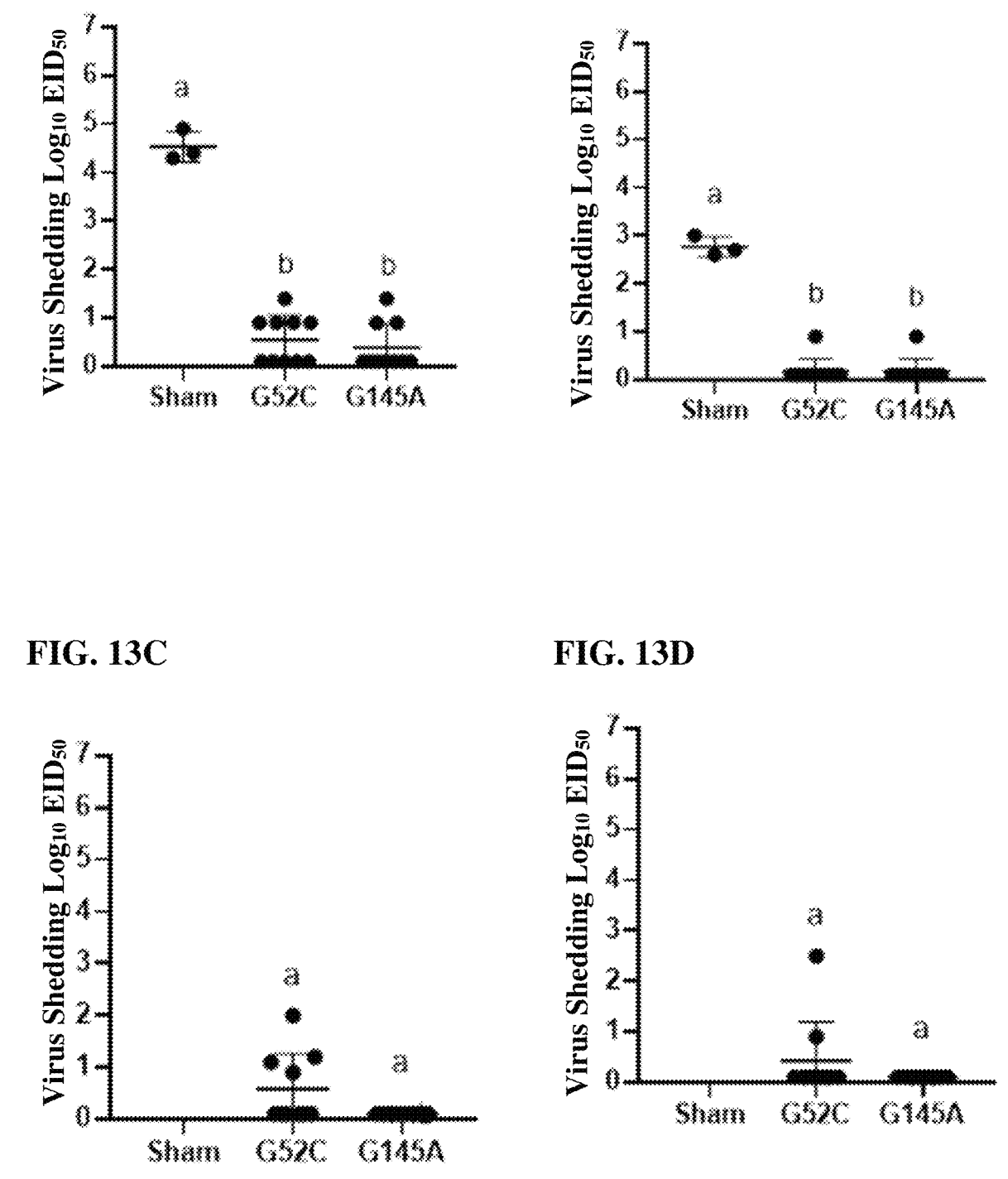

FIG. 13A to FIG. 13D depict graphs of virus shedding in chickens sham vaccinated (Sham); vaccinated with recombinant influenza A virus expressing M gene segment comprising G52C (G52C); or expressing M gene segment comprising G145A (G145A) challenged with A/Chicken/Queretaro/14588-19/1994 H5N2, a heterologous highly pathogenic influenza A virus. FIG. 13A presents virus shedding in oral swabs 2 days post challenge. FIG. 13B presents virus shedding in cloacal swabs 2 days post challenge. FIG. 13C presents virus shedding in oral swabs 4 days post challenge. FIG. 13D presents virus shedding in cloacal swabs 4 days post challenge. The X axis shows the vaccine groups and the Y axis shows the $\log_{10}$ of the 50% embryo infectious dose ($\log_{10}$ $EID_{50}$).

FIG. 15A Challenge with heterologous highly pathogenic avian influenza virus A/Chicken/Hong Kong/37.4/2002 H5N1. FIG. 15B: Challenge with heterologous highly pathogenic avian influenza virus A/Northern Pintail/Washington/40964/2014 H5N2. The Y axis presents the percent survival. The X axis presents the days post challenge.

Figures 16A, 16B, 16C, 16D:
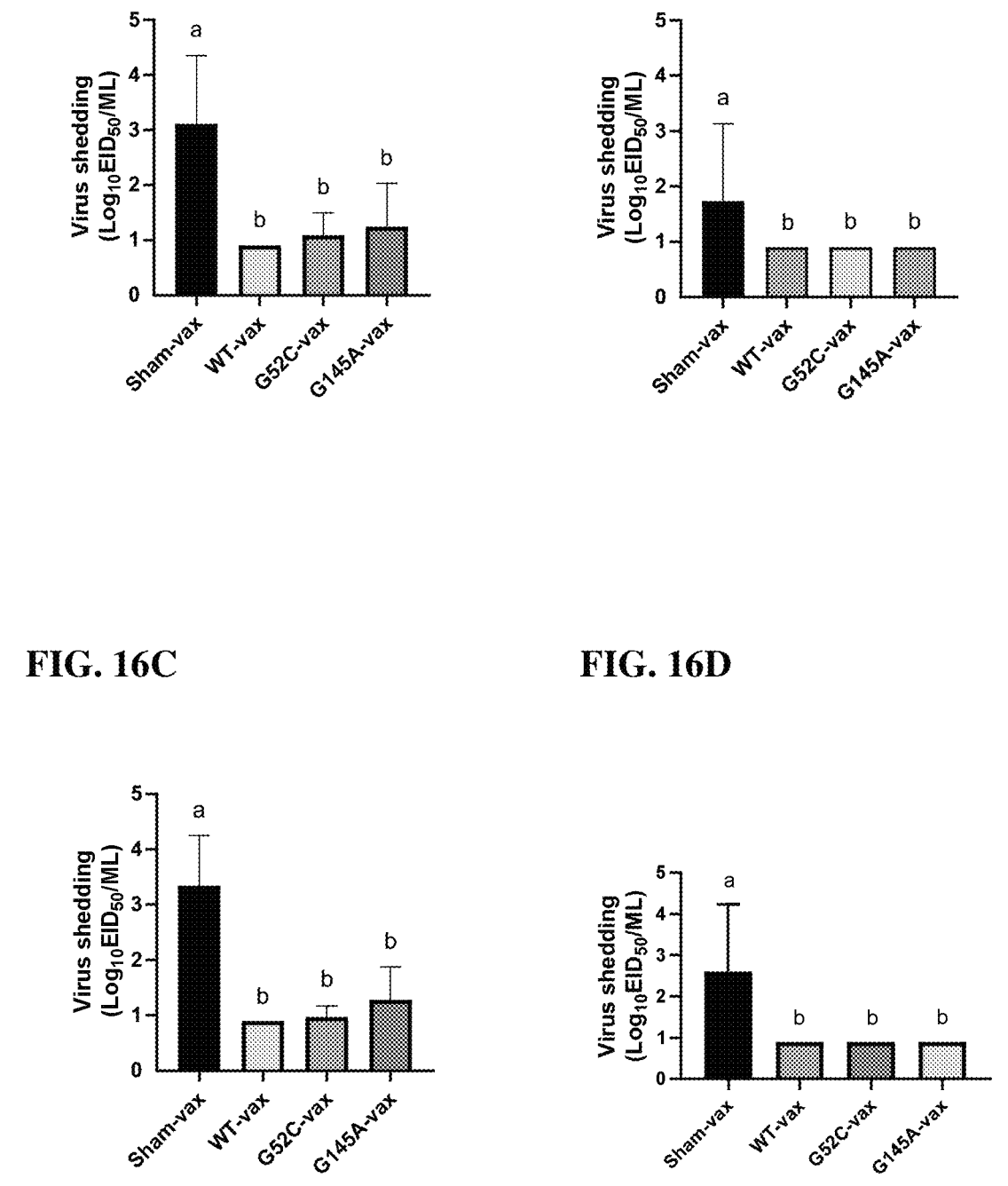

FIG. 16A to FIG. 16D depict graphs of virus shedding in sham vaccinated chickens (Sham-vax); chickens vaccinated with recombinant influenza A virus expressing a wild type M gene segment (WT-vax); chickens vaccinated with recombinant influenza A virus expressing an M gene segment comprising G52C (G52C-vax); or chickens vaccinated with recombinant influenza virus expressing M gene segment comprising G145A (G145A-vax), and challenged with A/Chicken/Hong Kong/483/2002, an H5N1 heterologous highly pathogenic influenza A virus of the Asian lineage. FIG. 16A presents the virus shedding in oral swabs 2 days post challenge. FIG. 16B presents the virus shedding in cloacal swabs 2 days post challenge. FIG. 16C presents the virus shedding in oral swabs 4 days post challenge. FIG. 16D presents the virus shedding in cloacal swabs 4 days post challenge. The X axis shows the vaccine groups, and the Y axis shows the $\log_{10}$ of the 50% embryo infectious dose ($\log_{10}$ $EID_{50}$).

Figures 17A, 17B, 17C, 17D:
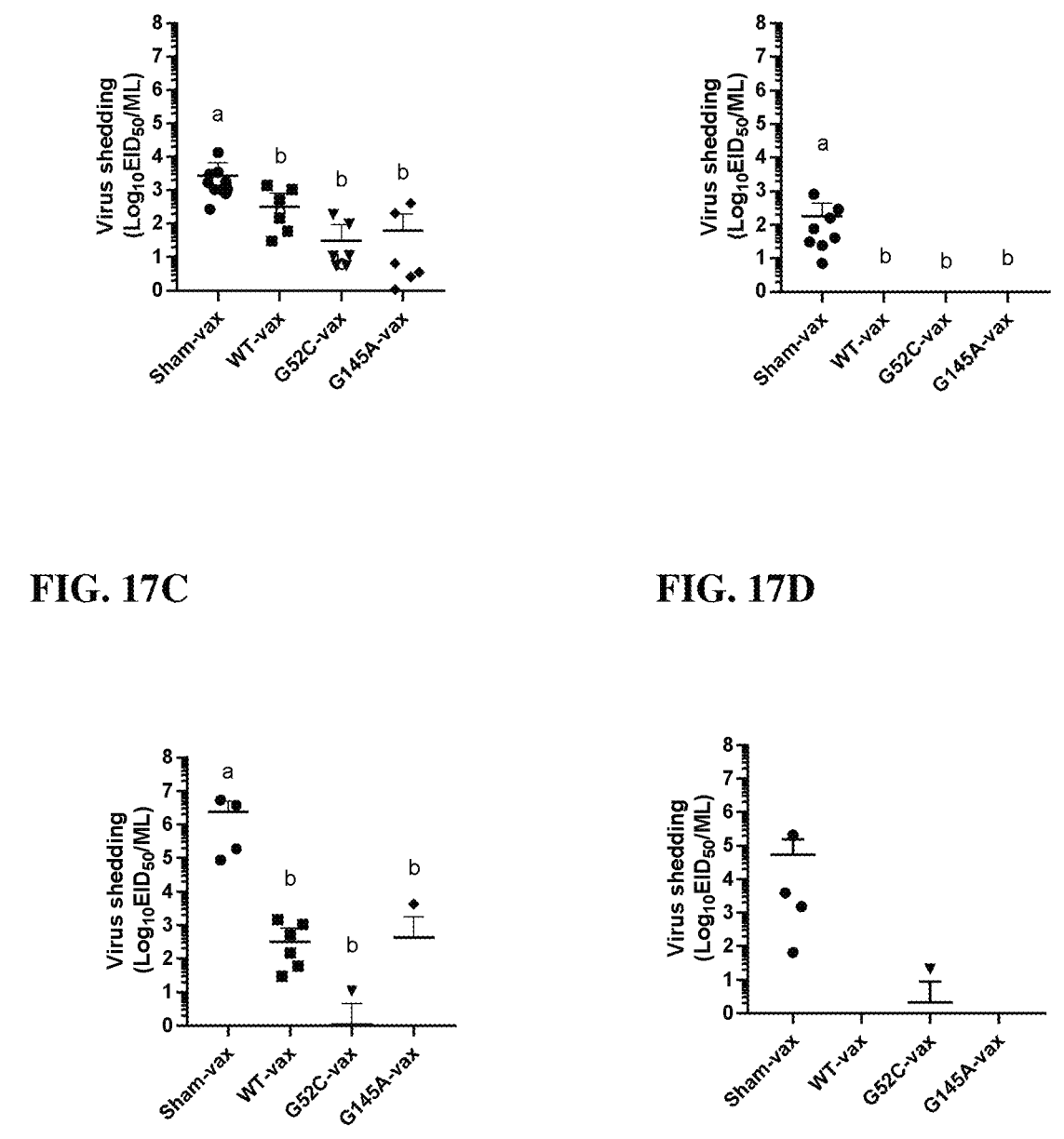

FIG. 17A to FIG. 17D depict graphs of virus shedding in sham vaccinated chickens (Sham-vax); chickens vaccinated with recombinant influenza A virus expressing a wild type M gene segment (WT-vax); chickens vaccinated with recombinant influenza A virus expressing an M gene segment comprising G52C (G52C-vax); or chickens vaccinated with recombinant influenza virus expressing M gene segment comprising G145A (G145A-vax), and challenged with A/Northern Pintail/Washington/40964/2014, a H5N2 heterologous highly pathogenic influenza A virus of the Asian lineage. FIG. 17A presents virus shedding in oral swabs 2 days post challenge. FIG. 17B presents virus shedding in cloacal swabs 2 days post challenge. FIG. 17C presents virus shedding in oral swabs 4 days post challenge. FIG. 17D presents virus shedding in cloacal swabs 4 days post challenge. The X axis shows the vaccine groups, and the Y axis shows the $\log_{10}$ of the 50% embryo infectious dose ($\log_{10}$ $EID_{50}$).

Figures 18A, 18B, 18C, 18D:
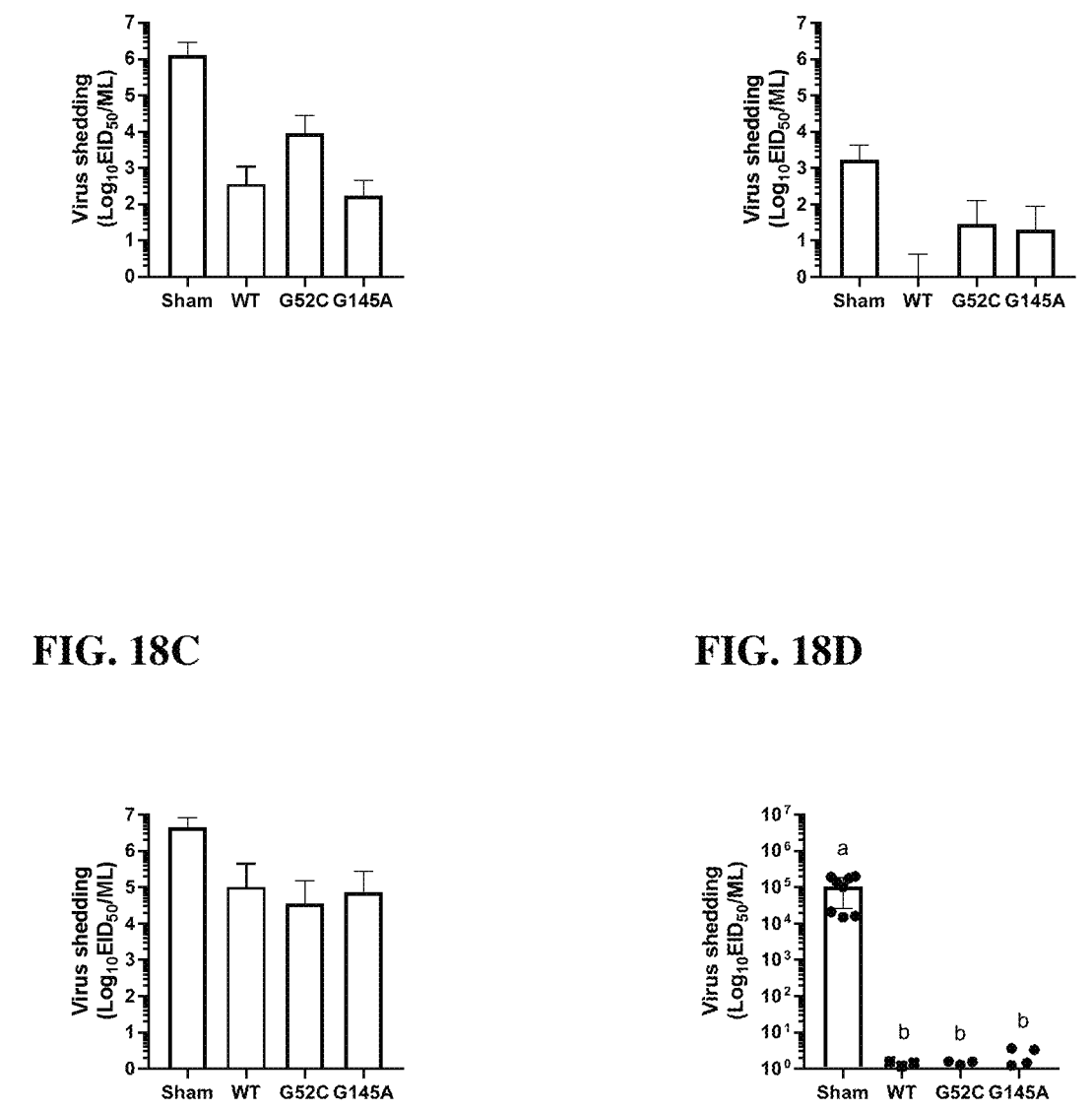

FIG. 18A to FIG. 18D depict graphs of virus shedding in chickens sham vaccinated (Sham); or vaccinated with killed recombinant influenza A virus expressing a wild type M gene segment (WT); expressing an M gene segment comprising G52C (G52C); or expressing an M gene segment comprising G145A (G145A), and challenged with the highly pathogenic H5N2 homologous influenza A virus A/Chicken/Pennsylvania/1370/1983 of the North American lineage. FIG. 18A presents virus shedding in oral swabs 2 days post challenge. FIG. 18B presents virus shedding in oral swabs 4 days post challenge. FIG. 18C presents virus shedding in cloacal swabs 2 days post challenge. FIG. 18D presents virus shedding in cloacal swabs 4 days post challenge. The X axis shows the vaccine groups, and the Y axis shows the $\log_{10}$ of the 50% embryo infectious dose ($\log_{10}$ $EID_{50}$).

BRIEF DESCRIPTION OF THE SEQUENCE LISTING

Figure 1:
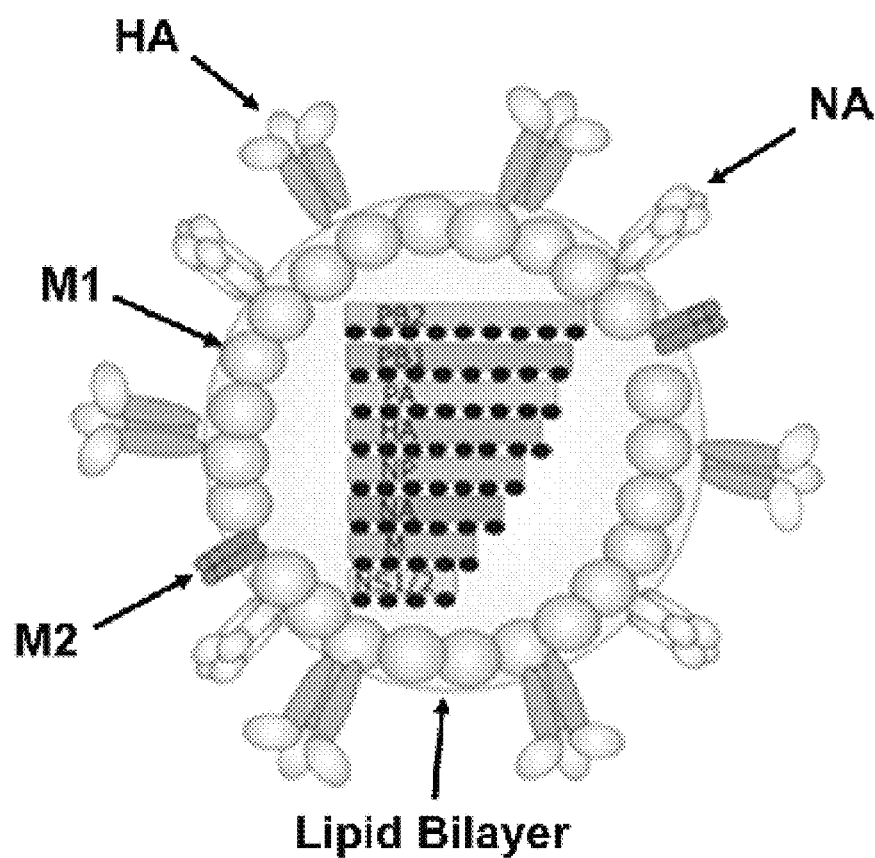
FIG. 1 depicts an influenza A virus schematic showing the virion shape, the lipid bilayer, the location of the membrane bound proteins HA, NA, M1, and M2; and the genome segments PB2, PB1, PA, HA, NP, NA, M, and NS1/2 inside the virion.

Table 1 below, lists the Sequence Identifiers in the instant application.

TABLE 1

| Influenza strain | Type | SEQ ID NO: |
| --- | --- | --- |
| A/chicken/Pennsylvania/1/1983 Segment 7 | nucleotide | SEQ ID NO: 1 |
| M42 protein encoded by segment 7 with G52C | amino acid | SEQ ID NO: 2 |

TABLE 1-continued

| Influenza strain | Type | SEQ ID NO: |
|---|---|---|
| M2 protein encoded by segment 7 with G145A | amino acid | SEQ ID NO: 3 |
| A/chicken/Pennsylvania/1/1983 with G52C | nucleotide | SEQ ID NO: 4 |
| A/chicken/Pennsylvania/1/1983 with G145A | nucleotide | SEQ ID NO: 5 |
| A/chicken/Queretaro/14588_19/1995 with G52C | nucleotide | SEQ ID NO: 6 |
| A/chicken/Queretaro/14588_19/1995 with G145A | nucleotide | SEQ ID NO: 7 |
| A/goose/Guangdong/3/1997 with G52C | nucleotide | SEQ ID NO: 8 |
| A/goose/Guangdong/3/1997 with G145A | nucleotide | SEQ ID NO: 9 |
| A/equine/newMarket/1/77 with G52C | nucleotide | SEQ ID NO: 10 |
| A/equine/newMarket/1/77 with G145A | nucleotide | SEQ ID NO: 11 |
| A/equine/Kentucky/1/1991 with G52C | nucleotide | SEQ ID NO: 12 |
| A/equine/Kentucky/1/1991 with G145A | nucleotide | SEQ ID NO: 13 |
| A/equine/Tennessee/27A/2014 with G52C | nucleotide | SEQ ID NO: 14 |
| A/equine/Tennessee/27A/2014 with G145A | nucleotide | SEQ ID NO: 15 |
| A/canine/Kentucky/20170606_23/2017 with G52C | nucleotide | SEQ ID NO: 16 |
| A/canine/Kentucky/20170606_23/2017 with G145A | nucleotide | SEQ ID NO: 17 |
| A/canine/Guangxi/LZ56/2015 with G52C | nucleotide | SEQ ID NO: 18 |
| A/canine/Guangxi/LZ56/2015 with G145A | nucleotide | SEQ ID NO: 19 |
| A/canine/New_York/1623.1/2010 with G52C | nucleotide | SEQ ID NO: 20 |
| A/canine/New_York/1623.1/2010 with G145A | nucleotide | SEQ ID NO: 21 |
| A/Brevig_Mission/l/1918 with G52C | nucleotide | SEQ ID NO: 22 |
| A/Brevig_Mission/l/1918 with G145A | nucleotide | SEQ ID NO: 23 |
| A/California/VRDL363/2009 with G52C | nucleotide | SEQ ID NO: 24 |
| A/California/VRDL363/2009 with G145A | nucleotide | SEQ ID NO: 25 |
| A/Idaho/19/2018 with G52C mutation | nucleotide | SEQ ID NO: 26 |
| A/Idaho/19/2018 with G145A | nucleotide | SEQ ID NO: 27 |

DETAILED DESCRIPTION OF THE INVENTION

As used herein, the singular forms "a," "an," and "the" designate both the singular and the plural, unless the context clearly indicates otherwise.

The term "about" is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the recited value.

The terms "individual," "subject," and "animal", are used interchangeably herein, and refer to vertebrates that support a negative strand RNA virus infection, specifically influenza A virus infection.

Exemplary subjects may include vertebrates of importance to humans due to being endangered, being of economic importance such as those raised on farms for consumption by humans, and/or being of social importance such as animals kept as pets or in zoos. The methods and compositions of the present disclosure are particularly useful for warm-blooded vertebrates including, but not limited to, birds, Canidae, Cetacea, Felidae, Mustelidae, Rodentia, Equidae, Bovidae, Suidae, and Primates. In some embodiments the vertebrates are birds such as water fowl, chickens, or turkeys. In some embodiments the vertebrates are mammals such as pigs, horses, whales, dolphins, or humans. In some embodiments the vertebrates are humans. In some embodiments the vertebrates are chickens.

As used herein, the terms "isolated," and "purified" refer to material that is substantially or essentially free from components that normally accompany the referenced material in its native state.

As used herein, the terms "gene segment 7," "M1/M2 gene segment," and "M gene segment" are used interchangeably and refer to the Influenza A RNA segment 7 encoding at least the M1/M2/M42 proteins.

As used herein, "substantially free" means below the level of detection for a particular agent, using standard detection methods for that agent, such as unwanted nucleic acids, proteins, cells, viruses, infectious agents, etc.

As used herein, a "recombinant virus" is one which has been manipulated in vitro, e.g., using recombinant nucleic acid techniques to introduce changes to the viral genome, or a virus that is artificially generated.

As used herein, the terms "recombinant nucleic acid," "recombinant segment," and "recombinant polynucleotide" are used interchangeably and refer to a nucleic acid that has been altered in vitro. The sequence of a recombinant polynucleotide is not naturally occurring, or does not correspond to naturally occurring sequences, or that are not positioned as they would be positioned in the native genome.

By "pharmaceutical composition" is meant a composition that contains a recombinant mutant influenza gene segment of the invention, or a recombinant influenza virus of the invention, and that is suitable for administration to a subject. The pharmaceutical composition is suitable to prevent, treat, reduce, or ameliorate one or more influenza symptoms in the subject. For the purposes of this invention, pharmaceutical compositions include vaccines.

As used herein "diluent," excipient," "carrier," and "adjuvant" are used interchangeably, and refer to a diluent, excipient, carrier, or adjuvant which is physiologically acceptable to the subject while retaining the therapeutic properties of the pharmaceutical composition with which it is administered. Physiologically acceptable diluents, excipients, carriers, or adjuvants and their formulations are known to one skilled in the art (see, e.g., U.S. Pat. No. 9,017,691; Chaudhari S. P., et al. 2012, *Pharmaceutical Excipients: A Review,*" IJAPBC Vol 1(1)). Reed S. G., et al. (2013, *"Key Roles of Adjuvants in Modern Medicines,"* Nature Medicine 19(12): 1597-1608) review adjuvants used in vaccines.

As used herein, the term "attenuated," as used in conjunction with a virus, refers to a virus having reduced virulence or pathogenicity as compared to a non-attenuated counterpart, yet is still viable or live. Typically, attenuation renders an infectious agent, such as a virus, less harmful or virulent to an infected subject compared to a non-attenuated virus.

The terms "inoculated" and "vaccinated" are used interchangeably herein and refer to the act of introducing recombinant influenza viruses comprising a G52C mutation or a G145A mutation into chickens.

The Orthomyxoviruses are a family of RNA viruses that includes seven genera: Influenza virus A, Influenza virus B, Influenza virus C, Influenza virus D, Isavirus, Thogotovirus, and Quaranjavirus. Influenza A virus is one of the world's major uncontrolled pathogens, causing seasonal epidemics as well as global pandemics. Influenza A viruses can infect various vertebrate hosts including birds and mammals. Influenza vertebrate hosts are birds, Canidae, Cetacea, Felidae, Mustelidae, Rodentia, Equidae, Bovidae, Suidae, and Primates. In some embodiments the vertebrates are birds such as water fowl, chickens, or turkeys. In some embodiments the vertebrates are mammals such as pigs, horses, whales, dolphins, or humans. In some embodiments the vertebrates are humans. In some embodiments the vertebrates are chickens, turkeys, dolphins, whales, swine, horses, or humans.

The genome of the Influenza A virus is negative-sense, single-stranded, segmented RNA. The Influenza A subtypes are named (HxNy) according to the type of hemagglutinin (H) and the type of neuraminidase (N) present in the virus. Up to date 16 different H antigens and 9 different N antigens are known.

The Influenza virus particle (also called a virion) is made of a viral envelope wrapped around a central core. A schematic diagram of an influenza A virion is shown in FIG. 1. The outer layer of the influenza virion is a lipid membrane taken from the host cell in which the virus multiplies. Inserted into the lipid membrane are the hemagglutinin (HA) protein, the neuraminidase (NA) protein, and the matrix-2 (M2) protein. Four M2 proteins form a proton-selective ion channel where the units are helices stabilized by two disulfide bonds. Beneath the lipid membrane is a layer of the matrix protein (M1) forming a shell. Within the interior of the virion are eight negative strand viral RNA segments consisting of RNA joined with the nucleoprotein (NP), and the three polymerase subunits (Polymerase Basic protein 1 (PB1), Polymerase Basic protein 2 (PB2), and polymerase acidic protein (PA)). Non-Structural protein 1 (NS1) and Non-Structural protein 2 (NS2) are found inside the virion.

Figure 2:
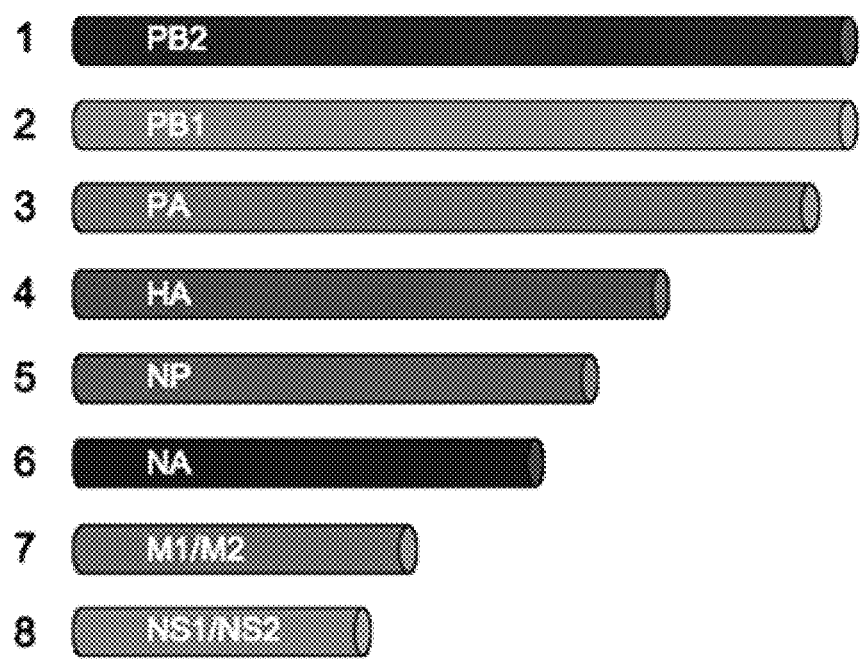
FIG. 2 depicts the eight gene segments present in the influenza A virion. Gene segment 1: PB2; gene segment 2: PB1; gene segment 3: PA; gene segment 4: HA; gene segment 5: NP; gene segment 6: NA; gene segment 7: M1/M2; and gene segment 8: NS1/NS2.

The eight RNA segments of the influenza A viral genome are depicted in FIG. 2. Gene segment 1, also referred to as PB2 gene segment, encodes the cap-binding transcriptase PB2. Using alternative translation initiation sites, gene segment 2, also referred to as PB1 gene segment, encodes elongation-associated proteins PB1, PB1-F2, and PB1-N40. By a ribosomal frameshift gene segment 3, also referred to as PA gene segment, encodes the polymerase acidic proteins PA and PA-X, and by using alternative translation sites and N-terminal truncation encodes PA-N155 and PA-N182. Gene segment 4, also referred to as HA gene segment, encodes the hemagglutinin protein HA. Gene segment 5, also referred to as NP gene segment, encodes the RNA binding nucleoprotein NP. Gene segment 6, also referred to as NA gene segment, encodes the neuraminidase protein NA. Gene segment 8, also referred to as NS1/NS2 gene, encodes the non-structural protein NS1, and by alternative RNA splicing it encodes NS3 and the nuclear export protein NS2/NEP.

Figure 3:
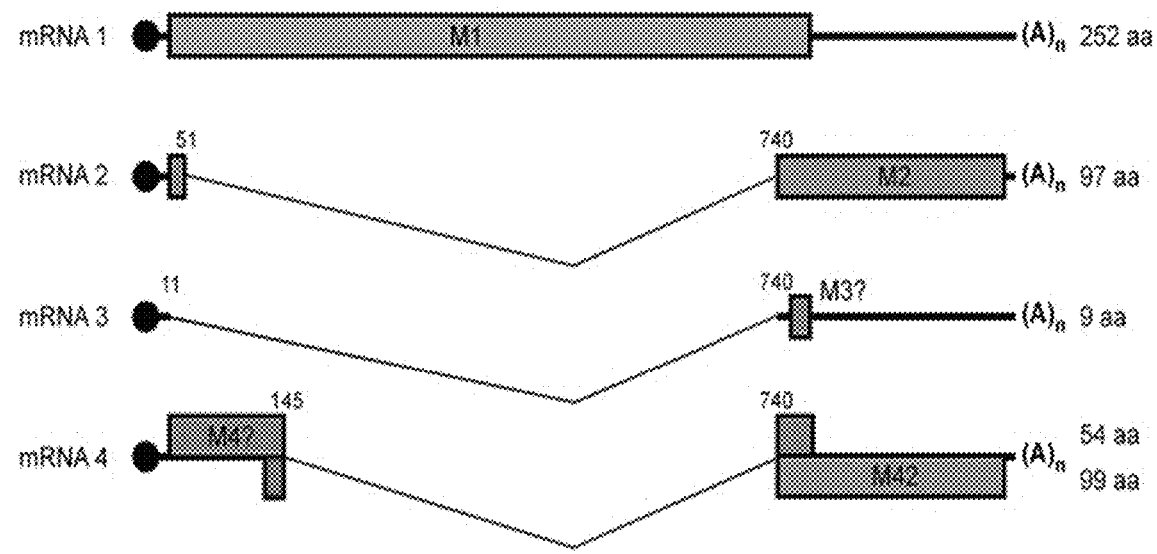
FIG. 3 depicts a diagrammatic summary of the mRNA splice variants from Influenza A Segment 7. The different mRNAs produced are indicated (mRNA1; mRNA2; mRNA3; and mRNA4). The open reading frames are indicated by boxes labeled with the name of the encoded polypeptide (M1; M2; M42) and the possible encoded polypeptide (M3? and M4?). In each mRNA, the number of the nucleotide at the splice site is indicated above the box. The number of amino acids in each polypeptide is indicated to the right of the figure.

The Influenza A virus genome segment 7 is also referred to as M gene or M1/M2 gene, and produces at least four mRNA transcripts (mRNA1, mRNA2, mRNA3, and mRNA4). A schematic diagram of the influenza segment 7 and its transcripts is shown in FIG. 3. The full-length M transcript is 1,004 nt. The M1 protein is encoded by mRNA1, the colinear transcript from the initiation codon at nucleotides 26 to 28 to the termination codon at nucleotides 782 to 784. The M2 protein is encoded by mRNA2 which comprises nucleotides 26 to 28 until nucleotide 51, and nucleotides 740 to nucleotide 1007. mRNA3 is interrupted from nucleotides 11 to 740 and is expected to produce a 9-amino acid polypeptide. mRNA4 codes for a third protein (M42), using an initiation codon at nucleotides 114 to 116. Strain-specific single nucleotide changes in the 5' single strand of segment 7 are said to result in marked alterations of splice site usage. M42 is said to result from leaky ribosomal scanning and to have an antigenically distinct ectodomain that can functionally complement M2 in vitro and in vivo. (Wise et al., 2012, *"Identification of a Novel Splice Variant Form of the Influenza A Virus M2 Ion Channel with an Antigenically Distinct Ectodomain,"* PLOS Pathogens 8(11): e1002998).

As described above, and depicted in FIG. 1, spanning the viral membrane are three proteins: hemagglutinin (HA), neuraminidase (NA), and M2. The extracellular domains (ectodomains) of HA and NA are quite variable, while the ectodomain domain of M2 is essentially invariant among influenza A viruses. Without wishing to be bound by theory, in influenza A viruses, the M2 protein which possesses ion channel activity, is thought to function at an early state in the viral life cycle between host cell penetration and uncoating of viral RNA. Once virions have undergone endocytosis, the virion-associated M2 ion channel, a homotetrameric helix bundle, is believed to permit protons to flow from the endosome into the virion interior to disrupt acid-labile M1 protein-ribonucleoprotein complex (RNP) interactions, thereby promoting RNP release into the cytoplasm. In addition, among some influenza strains whose HAs are cleaved intracellularly, the M2 ion channel is thought to raise the pH of the trans-Golgi network, preventing conformational changes in the HA due to conditions of low pH in this compartment. The M2 protein ion channel activity is thought to be essential in the life cycle of influenza viruses.

The influenza gene segment 7 is highly conserved among organisms. Table 2, below, presents the percent sequence similarity among gene segment 7 sequences from influenza isolates recovered from different species. Included in the table are sequences from 1) A/chicken/Pennsylvania/1/1983; 2) A/chicken/Queretaro/14588_19/1995; 3) A/goose/Guangdong/3/1997; 4) A/equine/Newmarket/1/77; 5) A/equine/Kentucky/1/1991; 6) A/equine/Tennessee/27A/2014; 7) A/canine/Kentucky/20170606_23/2017; 8) A/canine/Guangxi/LZ56/2015; 9) A/canine/New_York/1623.1/2010; 10) A/Brevig_Mission/1/1918; 11) A/California/VRDL363/2009; 12) A/Idaho/19/2018.

TABLE 2

Percent Similarity Among Gene Segment 7 from Influenza Isolates

| | 2 | 3 | 4 | 5 | 6 | 7 | 8 | 9 | 10 | 11 | 12 |
|---|---|---|---|---|---|---|---|---|---|---|---|
| 1 | 94.6 | 87.4 | 89.6 | 89.4 | 92.5 | 91.7 | 85.7 | 92.8 | 88.7 | 86.3 | 87.0 |
| 2 | | 87.5 | 90.3 | 90.0 | 92.9 | 92.0 | 86.3 | 92.6 | 89.6 | 87.0 | 87.4 |

TABLE 2-continued

Percent Similarity Among Gene Segment 7 from Influenza Isolates

|   | 2 | 3 | 4 | 5 | 6 | 7 | 8 | 9 | 10 | 11 | 12 |
|---|---|---|---|---|---|---|---|---|---|---|---|
| 3 |   |   | 91.8 | 90.8 | 86.6 | 90.2 | 91.4 | 87.0 | 91.7 | 86.3 | 89.7 |
| 4 |   |   |      | 96.7 | 91.5 | 87.8 | 89.9 | 91.5 | 94.0 | 87.4 | 87.2 |
| 5 |   |   |      |      | 94.1 | 87.9 | 88.5 | 94.1 | 92.2 | 87.2 | 87.8 |
| 6 |   |   |      |      |      | 91.0 | 84.8 | 97.5 | 87.9 | 85.9 | 86.7 |
| 7 |   |   |      |      |      |      | 86.7 | 90.9 | 87.7 | 85.3 | 87.3 |
| 8 |   |   |      |      |      |      |      | 84.7 | 91.0 | 84.4 | 95.7 |
| 9 |   |   |      |      |      |      |      |      | 88.2 | 85.3 | 86.5 |
| 10 |   |   |      |      |      |      |      |      |      | 90.1 | 88.4 |
| 11 |   |   |      |      |      |      |      |      |      |      | 85.5 |

As seen above in table 2, the highest similarity between influenza gene segment 7 sequences are A/equine/Tennessee/27A/2014 and A/canine/New-York/1623.1/2010 (97.5%, similarity along the entire nucleotide sequence); and A/canine/Goangxi/LZ56/2015 and A/Idaho/19/2018 have the lowest similarity between influenza gene segment 7 (84.4% similarity along the entire nucleotide sequence). Conserved among all Influenza A sequences tested are G52 and G145.

The complete nucleotide sequence of A/chicken/Pennsylvania/1/1983 H5N2 Segment 7 is depicted in FIG. 4 and is set forth in SEQ ID NO: 1. The accession.version of this sequence in GenBank is CY015074.1. The M2 protein initiation codon at nucleotides 26 to 28 is boxed; the M2 intron from nucleotides 51 to 739 is underlined; the M42 protein initiation codon at nucleotides 116 to 118 is boxed; the M42 intron from nucleotides 136 to 739 is written in italics; and the M2/M42 termination codon is boxed.

The inventors have prepared mutant A/chicken/Pennsylvania/1/1983 recombinant influenza viruses comprising a gene 7 segment with a replacement of the G at position 52 for a C. This mutation results in an intron spanning nucleotides 52 to 739 not being removed, and instead, an intron spanning nucleotides 146 to 739 being preferentially removed. Translation of the resulting mRNA starts at the AUG beginning at nucleotide 114, with the stop codon at nucleotides 1005 to 1007, producing the M42 protein. The inventors have prepared recombinant influenza viruses comprising a mutant A/chicken/Pennsylvania/1/1983 gene 7 segment with a replacement of the G at position 145 for an A. This mutation results in an intron spanning nucleotides 146 to 739 not being removed, and instead, an intron spanning nucleotides 52 to 739 being preferentially removed. Translation of the resulting mRNA starts at the AUG at nucleotides 26 to 28, with the stop codon at nucleotides 1005 to 1007, producing the M2 protein.

Surprisingly the inventors found that recombinant influenza viruses comprising a G52C mutation or a G145A mutation were attenuated and may be useful as a vaccine.

The inventors have prepared influenza gene segment mutants where the expression of the M2 and/or the M42 polypeptide is modulated. The inventors have prepared two different influenza gene segment 7 mutants, each with a single introduced mutation. The introduced mutations were a G to C at nucleotide 52 or a G to A at nucleotide 145 of the influenza A/chicken/Pennsylvania/1/1983 gene segment 7. Vectors carrying influenza gene 7 with the introduced mutations were used together with vectors carrying the wild-type remaining gene segments to prepare mutant recombinant influenza viruses.

An influenza virus comprising a gene segment 7 with the G52C mutation produces M42 protein but does not produce M2 protein. The M42 protein produced by the influenza virus comprising the gene segment 7 with the G52C mutation may comprise the amino acid sequence Gln-Gly-Lys-Thr-Leu-Ile-Leu-Arg, as set forth at amino acids 4 to 11 of SEQ ID NO: 2. The M42 protein produced by a virus comprising a gene segment 7 with a G52C mutation may have the amino acid sequence shown in FIG. 5 and set forth in SEQ ID NO: 2.

An influenza virus comprising the gene segment 7 with the G145A mutation produces M2 protein but does not produce M42 protein. The M2 protein produced by an influenza virus comprising a gene segment 7 with a G145A mutation may comprise the amino acid sequence Lys-Thr-Glu-Val-Glu-Thr, as set forth at amino acids 4 to 9 of SEQ ID NO: 3. The M2 protein produced by a virus comprising a gene segment 7 with a G145A mutation may have the amino acid sequence shown in FIG. 6 and set forth in SEQ ID NO: 3.

Recombinant influenza vaccines prepared with either of the mutant recombinant influenza gene segment 7 disclosed herein (with a G52C mutation or a G145A mutation) induce mucosal immunity, systemic antibodies, and cellular immunity against all influenza proteins. The recombinant influenza virus vaccines of the invention also present a broader spectrum of reactivity against all influenza viral proteins. The recombinant mutant influenza virus vaccines comprising a recombinant influenza gene segment 7 (with a G52C mutation or a G145A mutation) have a low pathogenic genotype and phenotype and have limited replication and transmission potential through interruption of the M2 or M42 genes, resulting in a decreased risk of reversion of the recombinant influenza virus vaccines of the invention.

A live attenuated influenza vaccine (LAIV) is currently available from MedImmune, Gaithersburg, Md., U.S.A. for use in humans. This vaccine comprises the HA and NA gene segments from a circulating influenza virus strain and the six remaining gene segments from a cold-adapted master donor influenza virus. The master donor virus imparts temperature sensitivity (ts), attenuation (att), and cold adaptation (ca). The PB1, PB2, and NP genetic loci are responsible for the att and ts phenotypes. A mutation in the M2 gene segment resulting in an M protein comprising a serine (Ser) at position 86 contributes to the att phenotype.

From 2002 to 2010 over 113 billion doses of avian influenza vaccines were applied to poultry. The majority of these vaccines were used in China, and the main type of the vaccines were killed influenza virus vaccines. In addition, in the United States, thousands of doses of killed influenza virus vaccines are applied yearly in the turkey sector, but not yet in the chicken sector.

Moreover, the swine industry, the equine sector, and the pet industry also vaccinate against influenza virus and vaccinations are routinely carried out in the United States. In the United States alone, over 120 million influenza vaccine doses were distributed every week per season since the 2011-2012 influenza season.

Outbreaks of highly pathogenic avian influenza virus have increased globally beginning in 2002. The virus has become more adapted to its natural host, wild migrating birds, which has resulted in increased spread of the virus to commercial poultry. For example, more than 150 million poultry were killed in Southeast Asia during the 2003-2004 Highly Pathogenic Avian Influenza (HPAI) H5N1 outbreaks with losses estimated at U.S. $10 billion dollars. During these outbreaks Thailand suffered the largest economic losses recording total estimates of about U.S. $1.2 billion dollars. Trade losses were severe in Thailand, which accounted for a significant amount of losses since the country had been the world's fifth largest poultry exporter in the world. In Korea, the economic losses associated with HPAI outbreaks were largest in 2016-2017 with expected estimates of at least U.S. $435 million dollars and a maximum of U.S. $1.3 billion dollars.

In the United States, from 2014-2015, an outbreak of HPAI resulted in the death of over 58 million birds. The majority of these birds being commercial poultry, resulting in an economic loss of approximately U.S. $3.3 billion dollars to the industry. This economic loss included U.S. $1.6 billion dollars from destroyed turkeys and turkey eggs. While influenza vaccines were developed and considered during this outbreak, they were not applied.

In an embodiment, the invention relates to recombinant influenza gene segment with at least one mutation that modulates expression of the M2 or the M42 polypeptide. In an embodiment, the invention relates to recombinant influenza gene segment 7 with either a G52C or a G145A mutation. The recombinant influenza gene segment 7 does not comprise a deletion of the M2 cytoplasmic tail and does not lack the transmembrane domain or has a mutated transmembrane domain. The recombinant influenza gene segment 7 does not comprise a deletion of eleven amino acids from the C terminus of the M2 protein. The recombinant gene segment 7 does not comprise two stop codons introduced at nucleotides 786 to 791, a deletion of nucleotides 792 to 842, and a G to C substitution at nucleotide 52 of influenza A/hvPR8/34 (H1N1). In some embodiments, the invention relates to the use of recombinant influenza gene segment 7 with either a G52C or a G145A mutation for the preparation of influenza vaccines. In addition, a distinguishing infected from vaccinated animals (DIVA) can be developed based on the subtype used for vaccine construction. For example, if the outbreak influenza virus has a H5N8 configuration, the vaccine virus can be developed in a H5N2 configuration, allowing for detection of the N2 protein to distinguish the vaccine from the field virus. As increased numbers of influenza outbreaks occur, with huge economic consequences, the future use of influenza vaccines will likely increase. Thus, adaption of the technology found in this invention for designing safe and efficacious vaccines for influenza based on mutant recombinant influenza virus gene segment 7 not expressing the M2 protein, or not expressing the M42 protein should prove to be a benefit to many different sectors.

In an embodiment, the invention relates to a recombinant influenza virus gene segment with at least one introduced mutation that modulates expression of the M2 and/or M42 polypeptides. In an embodiment, the invention relates to a recombinant influenza virus gene segment 7 with a single introduced mutation of G to C (G52C) at a position corresponding to nucleotide 52. In some embodiments, the mutant recombinant influenza virus gene segment 7 with a G52C mutation is from influenza A/chicken/Pennsylvania/1/1983. In some embodiments, the G52C mutation is introduced into gene segment 7 of influenza A/chicken/Pennsylvania/1/1983 having the nucleotide sequence set forth in SEQ ID NO:1.

In an embodiment, the invention relates to a recombinant influenza virus gene segment 7 with a single introduced mutation of G to A (G145A) at a position corresponding to nucleotide 145. In some embodiments, the mutant recombinant influenza virus gene segment 7 with a G145A mutation is from influenza A/chicken/Pennsylvania/1/1983. In some embodiments, the G145A mutation is introduced into gene segment 7 of influenza A/chicken/Pennsylvania/1/1983 having the nucleotide sequence set forth in SEQ ID NO: 1.

Figure 10A:
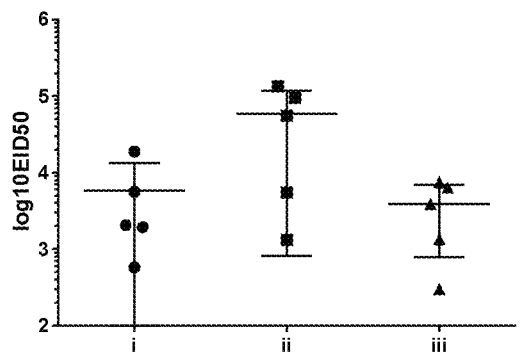
FIG. 10A to FIG. 10F depict graphs of the virus titer measured in chicken oral swabs at different days post vaccination with a recombinant A influenza virus, and in chickens in contact with the vaccinated birds.
Figure 10B:
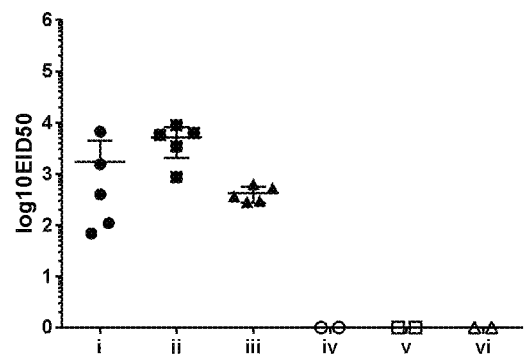
Figure 10C:
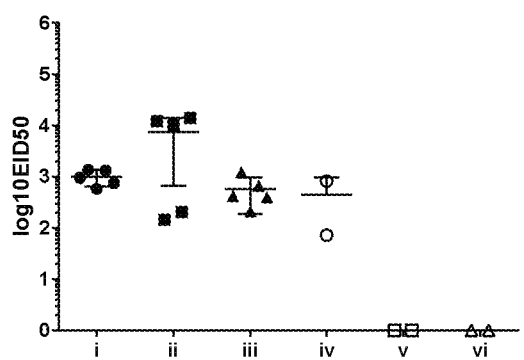
Figure 10D:
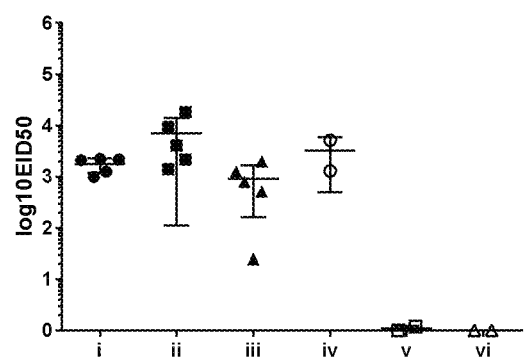
Figure 10E:
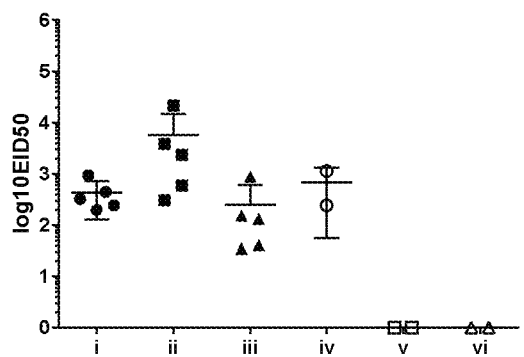
Figure 10F:
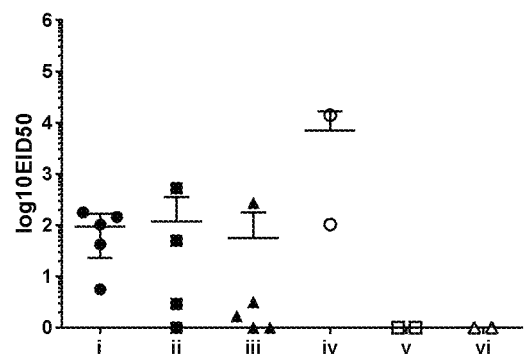

As described in the Examples below, recombinant influenza viruses comprising a gene segment 7 with a G52C mutation or G145A mutation are not transmitted from infected chicken to contact chicken. The results shown in FIG. 10 to FIG. 10F indicate that a virus with a wild type segment 7 is transmitted from vaccinated animals to contact susceptible birds. But, recombinant influenza viruses comprising a gene segment 7 with a G52C mutation (M2-/M42+) or a G145A mutation (M2+/M42-) are not transmitted from vaccinated animals to susceptible birds. These results suggest that recombinant influenza viruses comprising a gene segment 7 with a G52C mutation or a G145A mutation are attenuated viruses, and are potential vaccine candidates.

Vaccines comprising recombinant influenza virus gene segment 7 mutants disclosed herein elicited robust immune responses and protected chickens against challenge with a highly pathogenic influenza virus. Recombinant influenza viruses comprising a gene segment 7 with a G52C mutation or G145A mutation elicit humoral, cellular, and mucosal immune responses in chickens, and protect chickens from lethal challenge. Recombinant influenza viruses comprising mutant gene segment 7s of the invention may protect against challenge with HPAI of the North American lineage or the Asian lineage. The recombinant influenza viruses of the invention may protect against challenge with any HPAI, including A/goose/Zhejiang/925105/2014; A/chicken/Vietnam/NCVD-15A17/2015; A/goose/Yangzhou/ZG60/2009; A Northern pintail/Washington/40964/2014; A/chicken/Zhejiang/7450/2015; A/duck/Jiangsu/m234/20' 1; A/duck/Eastern China/L1120/2012; A/chicken/China/AH/2012; A/spot billed duck/Shanghai/PD1202-3/2013; A/chicken/Jiangxi/NCDZT1123/2014; A/wild pigeon/Jilin/CC01/2014/ A/black-crowned night heron/Vietnam/WBT198/2014; MN12803 1 1704 Goose [A/goose/Guangdong/GS013/2015]; A/chicken/Hubei/XG18/2015; A/duck/Wuhan/JXYFB22/2015; A/common teal/Shanghai/PD1108-8/2013; A/duck/Vietnam/8/05; A/goose/Guangdong/1/1996; A/Hong Kong/483/1997; A/Chicken/Hong Kong/37.4/2002; A/duck/Guangxi/53/2002; A/duck/Guangdong/07/2000; A/duck/Shantou/1437/2001; A/chicken/Queretaro/14588-19/1995; A/chicken/Pennsylvania/1370/1983.

Figure 11A:
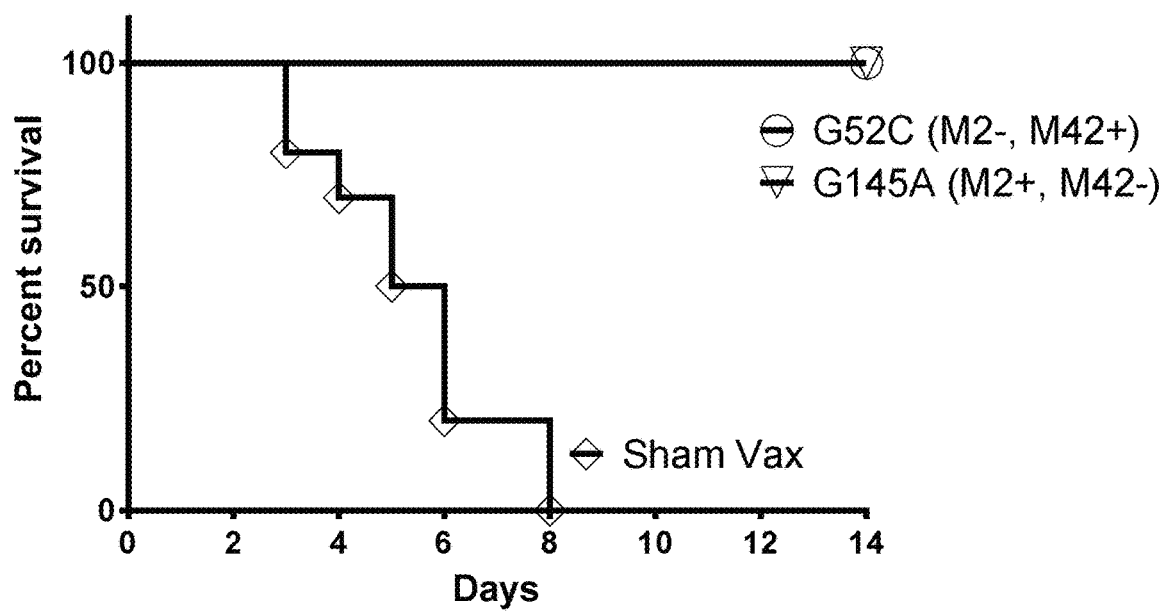
FIG. 11A and FIG. 11B depict graphs of the percent survival of chickens challenged with highly pathogenic avian influenza A virus in either sham-vaccinated (◇; Sham Vax); vaccinated with recombinant influenza A virus expressing M gene segment comprising G52C (⊖; M2−/M42+); or expressing M gene segment comprising G145A (▽; M2+/M42−).
Figure 11B:
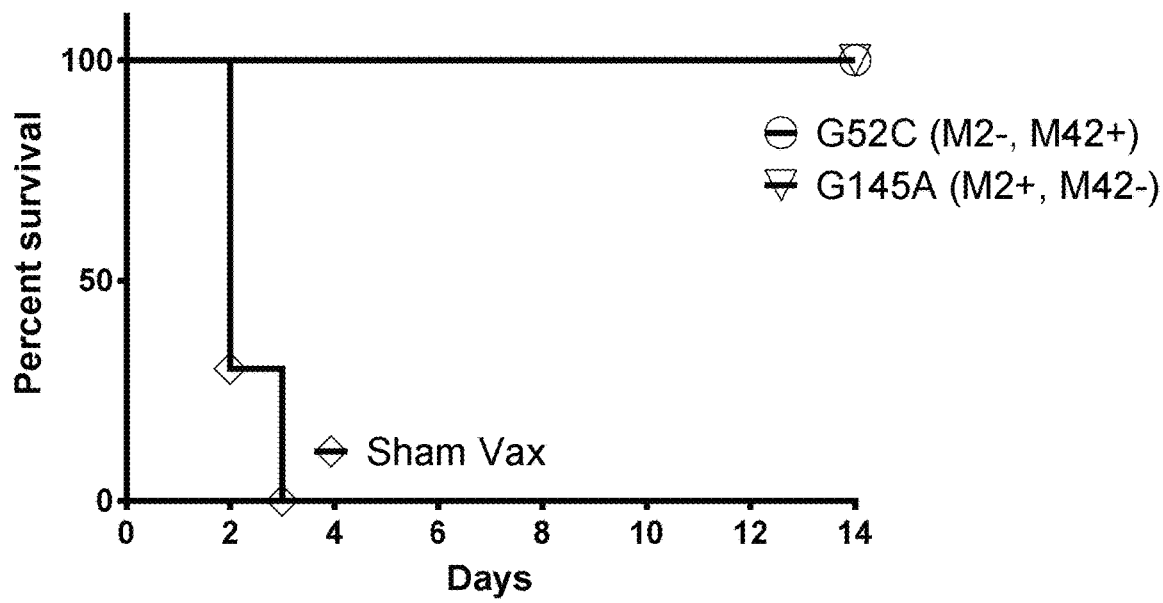
Figure 15A:
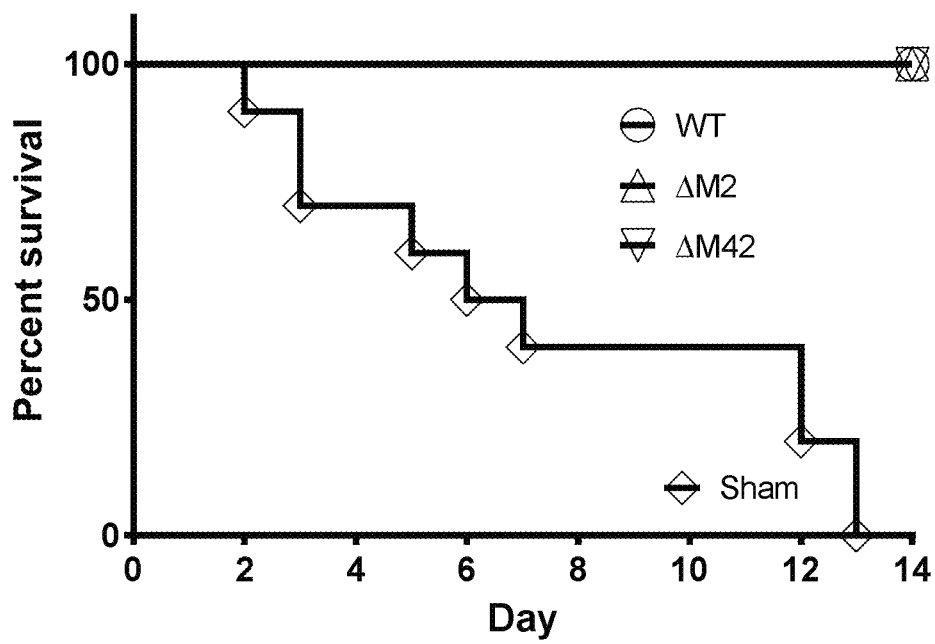
FIG. 15A and FIG. 15B depict graphs of the percent survival of chickens sham-vaccinated (◇; Sham Vax); vaccinated with recombinant influenza A virus expressing M gene segment comprising wild-type (⊖; M2+/M42+); or expressing M gene segment comprising G52C (▲; M2−/M42+); or expressing M gene segment comprising G145A (▽; M2+/M42−), and challenged with highly pathogenic avian influenza A virus of the Asian lineage.

As shown in FIG. 11A, the recombinant influenza viruses of the invention protect against challenge with A/chicken/Pennsylvania/1370/1983. As shown in FIG. 11B, the recombinant influenza viruses of the invention protect against challenge with A/chicken/Queretaro/14588-19/1995. As shown in FIG. 15A, the recombinant influenza viruses of the invention protect against challenge with A//Hong Kong/483/1997. As shown in FIG. 11B, the recombinant influenza viruses of the invention protect against challenge with A/Northern Pintail/Washington/4094/2014. Influenza vaccines comprising recombinant influenza viruses with a gene segment 7 with a G52C mutation or G145A mutation as described herein provide effective protection against influenza challenge and have the advantage of being attenuated in avian hosts. These findings demonstrate that the recombinant influenza viruses comprising a gene segment 7 with a G52C mutation or G145A mutation described herein are useful for the preparation of vaccines against influenza.

Methods of preparing recombinant influenza viruses are known in the art. For example, recombinant mutant influenza virus, such as those carrying a gene segment 7 with a G52C mutation or a G145A mutation, can be generated by plasmid-based reverse genetics as described by Neumann G., et al., (1999, *"Generation of influenza A viruses entirely from clone cDNAs"*, Proc. Natl. Acad. Sci. U.S.A. 96:9345-9350). Briefly, eukaryotic host cells are transfected with one or more plasmids encoding the eight viral RNAs. Each viral RNA sequence is flanked by an RNA polymerase I promoter and an RNA polymerase I terminator. Notably, the viral gene segment 7 includes the mutant nucleic acid sequence. The host cell is additionally transfected with one or more expression plasmids encoding the influenza viral proteins (e.g., polymerases, nucleoproteins and structural proteins). Transfection of the host cell with the viral RNA plasmids results in the synthesis of all eight influenza viral RNAs, one of which harbors a mutant segment 7 sequence. The co-transfected viral polymerases and nucleoproteins assemble the viral RNAs into functional vRNPs that are replicated and transcribed, ultimately forming infectious influenza virus having a mutant segment 7 nucleic acid sequence, and either having a functional M2 polypeptide (if gene segment 7 has a G145A mutation) or a functional M42 polypeptide (if gene segment 7 has a G52C mutation) incorporated into the viral lipid envelope.

Another method for preparing recombinant mutant influenza virus, such as those carrying a gene segment 7 with a G52C mutation or a G145A mutation, can be generated by plasmid-based reverse genetics as described by Wit E. et al. (2004, *"Efficient Generation and Growth of Influenza Virus A/PR/8/34 From Eight cDNA Fragments,"* Virus Res. 103 (1-2): 1555-161; DOI 10.1016/j.virusres.2004.02.028). Briefly, modified pHW2000 plasmids comprising the cDNAs for the—wild type influenza A segments PB2, PB1, PA, HA, NP, NA, NS together with either a construct comprising gene segment 7 with a G52C mutation, or a construct comprising gene segment 7 with a G145A mutation, flanked by bi-directional RNA polymerase I and RNA polymerase II promoters are transfected into 293T cells. The transfected viral segments assemble into mutant influenza viruses. The titers of the resulting viruses may be increased by transfecting fresh 293T cells. Protein assays may be used to determine the level of the M2 protein produced by the virus comprising the gene segment 7 with the G145A mutation, or the level of the M42 protein produced by the virus comprising the gene segment 7 with the G52C mutation.

Another method for preparing recombinant mutant influenza virus, such as those carrying a gene segment 7 with a G52C mutation or a G145A mutation, can be generated as described by Martinez-Sorbido L. and Garcia-Sastre A. (2010, *"Generation of Recombinant Influenza Virus from Plasmid DNA,"* J. Vis. Exp. 42:2057). Briefly, the eight influenza virus genes cloned into the ambisense plasmid pDZ are co-transfected, in suspension, in 293T-MDCK cells co-cultures (day 1). Twenty-four hours post-transfection, media without fetal bovine serum (FBS) but containing TPCK/trypsin is replaced (day 2). Forty-eight hours after changing media, tissue culture supernatant is harvested and used to infect MDCK or 10-day-old embryonated chicken eggs (day 4). 48-72 hours post-amplification, tissue culture supernatants from MDCK infected cells or allantoic fluid from eggs are harvested and assayed for presence of virus by HA (day 6). If no virus is detected, the same supernatants and/or allantoic fluids can be re-passaged into fresh MDCK cells and/or embryonated eggs.

An alternative method of producing a "first generation" mutant influenza virus includes a ribonucleoprotein (RNP) transfection system that allows the replacement of influenza virus genes with in vitro generated recombinant RNA molecules, as described by Enami M. and Palese P. (1991, *High-efficiency Formation of Influenza Virus Transfectants,"* J. Virol. 65(5):2711-2713).

Another method of producing mutant influenza virus includes the synthesis of the viral RNA in vitro and coating of the RNA transcripts with viral nucleoprotein (NP) and polymerase proteins that act as biologically active RNPs in the transfected cell as demonstrated by Luytjes W., et al., 1989, *"Amplification, Expression, and Packaging of a Foreign Gene by Influenza Virus,"* Cell 59:1107-1113).

In some embodiments, Influenza A viral mutants described herein are maintained and passaged in host cells. Exemplary host cells appropriate for growth of influenza A viral mutants include any number of eukaryotic cells, including, Madin-Darby canine kidney cells (MDCK cells), simian cells such as African green monkey cells (e.g., Vero cells), CV-1 cells and rhesus monkey kidney cells (e.g., LLcomk.2 cells), bovine cells (e.g., MDBK cells), swine cells, ferret cells (e.g., mink lung cells) BK-1 cells, rodent cells (e.g., Chinese Hamster Ovary cells), human cells, e.g., embryonic human retinal cells (e.g., PER-C6®), 293T human embryonic kidney cells and avian cells including embryonic fibroblasts.

The eukaryotic host cell in which the influenza virus is maintained and passaged may be modified to enhance viral production, e.g., by enhancing viral infection of the host cell and/or by enhancing viral growth rate. For example, the host cell may be modified to express, or to have increased expression, of 2,6-linked sialic acid on the cell surface, allowing for more efficient and effective infection of these cells by mutant or wild-type influenza A viruses. See e.g., U.S. Pat. Nos. 8,163,523; and 7,176,021. Thus, Chinese Hamster Ovary Cells (CHO cells) and/or Vero cells modified to express at least one copy of a 2,6-sialyltransferase gene (ST6GAL 1) are useful in the production of recombinant influenza viruses, such as those carrying a gene segment 7 with a G52C mutation or a G145A mutation.

Host cells can then be transfected by methods known in the art, cells can be selected and tested for expression of M2 or M42 by cotransfection with a detectable marker or a selectable marker (e.g., hygromycin-resistance) and/or by screening, for example, using an antibody that binds to M2 and/or M42. Expression of M2 or M42 can be determined by indirect immunostaining, flow cytometry, or ELISA.

In some embodiments, cells and viral mutants are cultured and propagated by methods well known in the art. For example, host cells may be grown in the presence of Minimum Essential Medium supplemented with 10% fetal calf serum. Cells expressing M2 and/or M42 are infected at a multiplicity of infection (MOI) of 0.001 by washing with PBS followed by adsorbing virus at 37° C. Viral growth media containing trypsin/TPCK is added, and the cells are incubated for 2-3 days until cytopathic effect is observed.

For long term storage, mutant virus can be stored as frozen stocks.

Different types of influenza virus vaccines can be prepared with the recombinant mutant influenza gene segment 7 disclosed. The vaccines may be live attenuated virus vaccines, inactivated virus vaccines, whole virus vaccines, split virus vaccines, virosomal virus vaccines, viral surface antigen vaccines, and combinations thereof. Thus, there are numerous vaccines capable of producing a protective immune response specific for different influenza viruses where appropriate formulations of any of these vaccine types are capable of producing an immune response, e.g., a systemic immune response including antibodies and cellular immunity. Live attenuated virus vaccines have the advantage of also being able to stimulate local mucosal immunity in the respiratory tract.

In some embodiments, a recombinant influenza virion comprises all eight influenza gene segments, with gene segment 7 having only one introduced mutation, selected from G52C and G145A. In some embodiments, the recombinant influenza virus gene segment 7 may be a A/chicken/Pennsylvania/1983 gene segment 7 with a G52C or a G145A mutation. The wild-type influenza virus gene segment 7 may have the nucleotide sequence set forth in SEQ ID NO: 1.

In some embodiments a complete virion vaccine is provided. A complete virion vaccine can be concentrated by ultrafiltration and then purified using zonal centrifugation or using chromatography.

In some embodiments, live attenuated influenza virus vaccines are provided. Such vaccines can be used for preventing or treating influenza virus infection, according to known method steps.

In some embodiments the recombinant influenza vaccine of the invention includes a gene segment 7 with an introduced mutation that modulates the expression of the M2 and/or M42 polypeptides. In some embodiments, the recombinant influenza vaccine of the invention includes a segment 7 with only one introduced mutation. When the introduced mutation is a G52C mutation the M42 protein is expressed and the M2 protein is not expressed. When the introduced mutation is a G145A mutation the M2 protein is expressed and the M42 protein is not expressed.

Pharmaceutical compositions of the present invention, suitable for intradermal administration, inoculation, or for parenteral or oral administration, comprise attenuated or inactivated influenza viruses, and may optionally further comprising sterile aqueous or non-aqueous solutions, suspensions, and emulsions. The compositions can further comprise auxiliary agents or excipients, as known in the art.

In some embodiments, preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the vaccine. The preparation and use of pharmaceutically acceptable carriers is well known in the art. Except insofar as any conventional media or agent is incompatible with the active ingredient, use thereof in the immunogenic compositions of the present invention is contemplated.

When a composition of the present invention is used for administration to an individual, it may further comprise salts, buffers, adjuvants, or other substances which are desirable for improving the efficacy of the composition. For vaccines, adjuvants, substances that augment a specific immune response, can be used. Normally, the adjuvant and the composition are mixed prior to presentation to the immune system, or presented separately, but into the same site of the organism being immunized.

In some embodiments, the immunogenic compositions (e.g., vaccines) disclosed herein include multiple, different types of virus or viral antigens, at least one of which includes an influenza gene segment 7 with a single introduced mutation selected from the group consisting of G52C and G145A, or an influenza gene segment 7 having the nucleotide sequence set forth in SEQ ID NO:1 with either a G52C or a G145A introduced mutation. In other embodiments, the immunogenic compositions include a single type of virus or viral antigen which includes a mutant influenza gene segment 7 with a single introduced mutation selected from the group consisting of G52C and G145A, or an influenza gene segment 7 having the nucleotide sequence set forth in SEQ ID NO:1 with either a G52C mutation or G145A mutation. For example, in some embodiments, the main constituent of an immunogenic compositions such as a vaccine composition includes one or more influenza viruses of type A, B or C, or any combination thereof, or any combination of antigens from these viruses, wherein at least one virus includes a mutant influenza gene segment 7 with a single introduced mutation selected from the group consisting of G52C and G145A, or an influenza gene segment 7 having the nucleotide sequence set forth in SEQ ID NO:1 with a G52C or G145A introduced mutation. In some embodiments, the immunogenic compositions (e.g., vaccines) include an influenza virus comprising a gene segment 7 comprising a single introduced mutation selected from the group consisting of G52C and G145A, or an influenza gene segment 7 having the nucleotide sequence set forth in SEQ ID NO:1 with a G52C or G145A introduced mutation and about 0.1 to 200 µg, e.g., 10 to 15 µg of hemagglutinin from each of the strains entering into the composition. Heterogeneity in a vaccine may be provided by mixing replicated influenza viruses for at least two influenza virus strains, such as from 2-50 strains, or any range or value therein. In some embodiments, influenza A or B virus strains having a modern antigenic composition are used. In addition, immunogenic compositions (e.g., vaccines) can be provided for variations in a single strain of an influenza virus, using techniques known in the art.

In some embodiments, the vaccine comprises a virus comprising a gene segment 7 with an introduced mutation that modulates expression of the M2 and/or M42 polypeptides. In some embodiments, the vaccine comprises a virus comprising a gene segment 7 with a single introduced mutation selected from the group consisting of G52C and G145A together with other viral components and/or genes expressing other viral components. In some embodiments, the vaccine (e.g., an influenza virus comprising the gene segment 7 with a single introduced mutation selected from the group consisting of G52C and G145A) comprises gene segments from other influenza viral strains, including but not limited to, for example, gene segments from other viral influenza strains. In some embodiments the gene 7 segment in the vaccine is from an avian influenza virus, a feline influenza virus, a canine influenza virus, an equine influenza virus, or a human influenza virus. In some embodiments, the gene segment 7 in the vaccine is from A/chicken/Pennsylvania/1983. In some embodiments, the vaccine comprises recombinant gene segment 7 from human influenza virus type A subtypes such as H5N1, H1N1, H2N2 or H3N2. In some embodiments, the vaccine comprises a gene segment 7 from, for example, PR8×Brisbane/10/2007, A/Vietnam/1203/2004, or A/California/07/2009 (CA07) human viruses. In some embodiments, the vaccine comprises gene segment 7 from canine subtypes, equine subtypes, feline subtypes, and other avian subtypes, for example, A/equine/Kentucky/1/1991, A/canine/Kentucky/20170606_23/2017, or A/chicken/Queretaro/14588_19/1995.

A pharmaceutical composition according to the present invention may further or additionally comprise at least one chemotherapeutic compound, e.g., for gene therapy, an immunosuppressant, an anti-inflammatory agent or an immunostimulatory agent, or anti-viral agents including, but not limited to, gamma globulin, amantadine, guanidine, hydroxybenzimidazole, interferon-.alpha., interferon-.beta., interferon-.gamma., tumor necrosis factor-.alpha., thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition may also contain variable but small quantities of endotoxin-free formaldehyde, and preservatives, which have been found safe and not contributing to undesirable effects in the organism to which the composition of the invention is administered.

An immunogenic composition (e.g., vaccine) as disclosed herein may be administered via any of the routes conventionally used or recommended for vaccines: parenteral route, mucosal route, and may be in various forms: injectable or sprayable liquid, formulation which has been freeze-dried or dried by atomization or air-dried, etc. Vaccines may be administered by means of a syringe or by means of a needle-free injector for intramuscular, subcutaneous or intradermal injection. Vaccines may also be administered by means of a nebulizer capable of delivering a dry powder or a liquid spray to the mucous membranes, whether they are nasal, ocular, pulmonary, vaginal, or rectal.

A vaccine as disclosed herein may confer resistance to one or more influenza strains by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain.

The present invention thus includes methods for preventing or attenuating a disease or disorder, e.g., infection by at least one influenza virus strain. As used herein, a vaccine is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described. For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. In some embodiments, an immunogenic composition as disclosed herein is by intramuscular or subcutaneous application.

In some embodiments, a regimen for preventing, suppressing, or treating an influenza virus-related pathology comprises administration of an effective amount of a vaccine composition as described herein, administered as a single treatment, or repeated as enhancing or booster dosages, over a period up to and including between one week and about 24 months, or any range or value therein. In some embodiments, an influenza vaccine as disclosed herein is administered annually.

According to the present invention, an "effective amount" of a vaccine composition is one that is sufficient to achieve a desired biological effect. It is understood that, in some embodiments, the effective dosage will be dependent upon the species, age, sex, health, and weight of the recipient, kind of concurrent treatment, if any, frequency of treatment, and the nature of the effect wanted. The ranges of effective doses provided below are not intended to be limiting and represent exemplary dose ranges. Thus, in some embodiments, the dosage will be tailored to the individual subject, as is understood and determinable by one of skill in the art. The dosage of an attenuated virus vaccine for a bird (e.g., chicken) can be from about $10^5$ $EID_{50}$ to about $10^7$ $EID_{50}$, or any range or value therein. The dose of inactivated vaccine can range from about 0.1 to 200, e.g., 5 µg of hemagglutinin protein. However, the dosage should be a safe and effective amount as determined by conventional methods, using existing vaccines as a starting point.

Live flu vaccines are traditionally delivered to birds intranasally (IN) or intraocularly (1O) to mimic the natural routes of infection and promote a similar immune response to that of natural virus infection. In some embodiments, an influenza virus comprising an influenza gene segment 7 with one introduced mutation selected from G52C or G145A is used in an influenza vaccine for intranasal administration.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

As described in the Examples below, recombinant mutant influenza virus M segment are useful for preparing recombinant mutant influenza viruses. The recombinant mutant influenza viruses are useful to protect against influenza challenge.

The following examples are intended only to further illustrate the invention and are not intended to limit the scope of the invention as defined by the claims.

EXAMPLES

Example 1

Production of Recombinant Mutant Influenza Viruses

Reverse genetics was utilized to prepare mutant avian influenza virions comprising mutations in the gene segment 7. Mutations were introduced at nucleotide 52 and 145 of the A/chicken/Pennsylvania/1/1983 gene segment 7 to generate G52C (M2−/M42+) and G145A (M2+/M42−), respectively.

The nucleic acid sequence of the wild type A/chicken/Pennsylvania/1/1983 gene segment 7 is set forth in SEQ ID NO: 1, and depicted in FIG. 4. In this figure, the G nucleotides at position 52 and 145 are indicated by an asterisk above the sequence. The nucleotides corresponding to the start and stop codons for the M2 and M42 polypeptides are boxed. The M2 intron sequence is underlined and the M42 intron sequence is in Italics.

Recombinant virions expressing a wild type M gene produced M2 protein and M42 protein (referred to here as M2+/M42+). Recombinant virions expressing an M gene comprising a G52C mutation produced M42 protein but not M2 protein (referred to here as M2−/M42+). FIG. 5 shows the sequence of the M42 protein produced by recombinant virions expressing an influenza gene segment 7 with a G52C mutation. This sequence is set forth in SEQ ID NO: 2. Recombinant virions expressing an M gene comprising a G145A mutation produced an M2 protein but no M42 protein (referred to here as M+/M42−). FIG. 6 shows the sequence of the M2 protein produced by recombinant virions expressing an influenza gene segment 7 with a G145A mutation. The amino acid sequence of the M2 protein is set forth in SEQ ID NO: 3.

The eight influenza gene segments (PB2, PB1, PA, HA, NP, NA, M, NS) from A/chicken/Pennsylvania/1/1983 were commercially synthesized, produced as full-length DNA copies, and supplied as plasmid clones by Biomatik (Cambridge, Ontario, Canada). The resulting eight segments were sequenced, and their identity confirmed by comparing their sequences with those from GenBank having accession.version No. CY015080.1 (PB2); CY015079.1 (PB1); CY015078.1 (PA); CY015073.1 (HA); CY015076.1 (NP); CY015075.1 (NA); CY015074.1 (M); and CY015077.1 (NS). The sequence of the A/chicken/Pennsylvania/1/1983 gene segment is set forth in SEQ ID NO: 1. Two mutant gene segment 7 were also commercially synthesized by Biomatik, one with a G to C change at position 52 (G52C), and one with a G to A change at position 145 (G145A).

The commercially synthesized gene segments were amplified using Polymerase Chain Reaction (PCR) and subcloned into modified pHW2000 plasmids using BsmB1 restriction endonuclease sites. In the resulting plasmids the viral cDNAs are flanked by bi-directional RNA polymerase I and RNA polymerase II promoters which are engineered to express influenza vRNA and mRNA, respectively.

Three different recombinant influenza viruses were prepared, (1) a recombinant virus comprising wild type gene segment 7 (M2+/M42+); (2) a recombinant virus comprising gene segment 7 with G52C (M42); and (3) a recombinant virus comprising gene segment 7 with G145A (M2). Constructs for the wild type PB2; PB1; PA; HA; NP; NA; and NS1/NS2 viral gene segments, together with either a wild-type gene segment 7 construct; a gene segment 7 with a G52C mutation construct; or a gene segment 7 with a G145A mutation construct, were transfected into 293T cells. Viruses were collected and labeled "P0 stock" and the titers increased by transfecting fresh 293T cells. After this transfection, infectious virus titers were detected in the supernatant, collected, and labeled P1 stock. Protein assays were used to determine the levels of the M2 and M42 proteins produced by the different viruses. Table 3, below, shows the levels of M2 and M42 protein produced by each of the three different viruses.

TABLE 3

| M2 and M42 Expression levels | | | |
|---|---|---|---|
| Construct | Wild Type | G52C | G145A |
| M2 levels | Normal | — | Normal |
| M42 levels | Normal | Normal | — |

Recombinant influenza viruses prepared with wild-type gene segment 7 produced both, M2 protein and M42 protein at normal levels. Recombinant influenza viruses prepared with a gene segment 7 containing a G52C mutation produced M42 protein at normal levels, but no M2 protein was detected. Recombinant influenza viruses prepared with gene segment 7 containing the G145A mutation produced M2 protein to normal levels, but no M42 protein was detected.

Example 2

Subcellular Localization of the M Protein and M42 Protein

The polypeptides encoded by influenza A virus gene segment 7 with a G52C mutation or with a G145A mutation present different subcellular localization patterns.

To investigate the subcellular localization patterns of the polypeptides produced by influenza A virus gene segment 7 with a single mutation selected from the group consisting of G52C and G145A, GFP-tagged expression constructs were prepared and used to prepare recombinant influenza virions. All influenza A gene segments for a low pathogenicity avian influenza virus (LPAI virus) and the GFP-labeled gene segment 7 mutant constructs were cloned into a reverse genetics plasmid vector. Standard rescue using 293T cells were successful to create viruses with altered expression of the M2 and M42 proteins.

Differential localization patterns of the M2 polypeptide and the M42 polypeptide were confirmed by quantification and co-localization. The M42 polypeptide appeared predominately localized in the Golgi, in contrast to the M2 polypeptide which was found to be more widespread with a cytoplasmic/plasma membrane-based localization in both QT-35 cells and A549 cells. The QT-35 cells are derived from methylcholanthrene-induced fibrosarcoma of Japanese quail, and available from the European Collection of Authenticated Cell Cultures (ECACC) Catalog No. 93120832). A549 cells are adenocarcinomic human alveolar basal epithelial cells available from the American Type Culture Collection (ATCC) Catalog No. CCL-185.

Mutagenic analysis of the polypeptides defined a dileucine motif present in M2 but absent in M42 that may underlie this difference.

Example 3

Properties of Influenza Virions Comprising Segment 7 Mutants

Recombinant influenza viruses comprising a gene segment 7 with a G52C mutation or a gene segment 7 with a G145A mutation showed changes in general virus morphology as compared to recombinant influenza viruses comprising a wild-type gene segment 7. The recombinant mutant influenza virions also showed decreased replication in both cell culture and in chicken embryos.

Electron photomicrograph images of virions produced by the viruses prepared in Example 1 are shown in FIG. 7A to FIG. 7G. Recombinant influenza virions comprising wild-type gene segment 7 appeared as slightly elongated spheres. An electron photomicrograph from a representative field is shown on FIG. 7A. The virions in this electron photomicrograph measured 125×110 nm; 110×96.2 nm; 104×96.9 nm; 142×181 nm; and 93.1×107 nm.

Figure 7A:
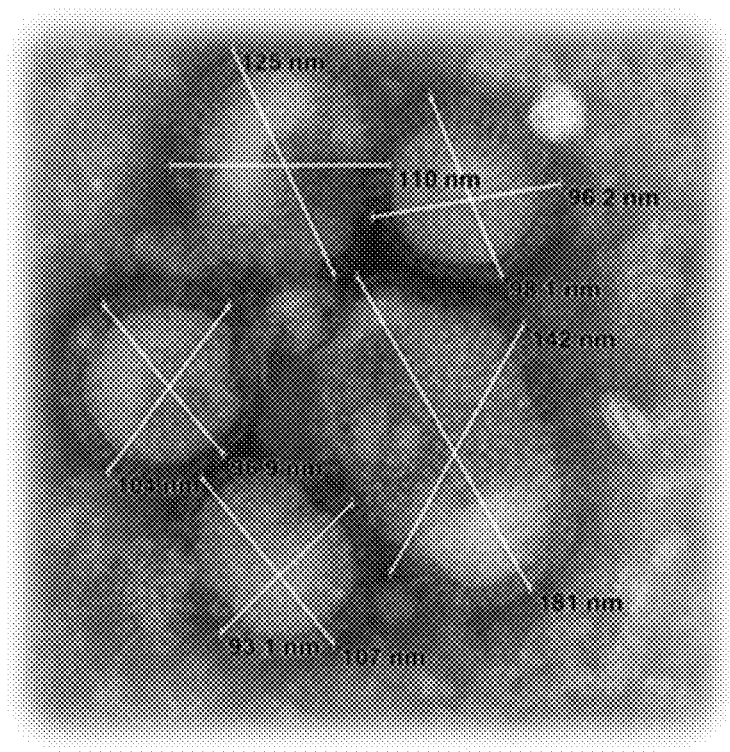
FIG. 7A to FIG. 7G depict electron photomicrographs of recombinant influenza A virions.
Figure 7B:
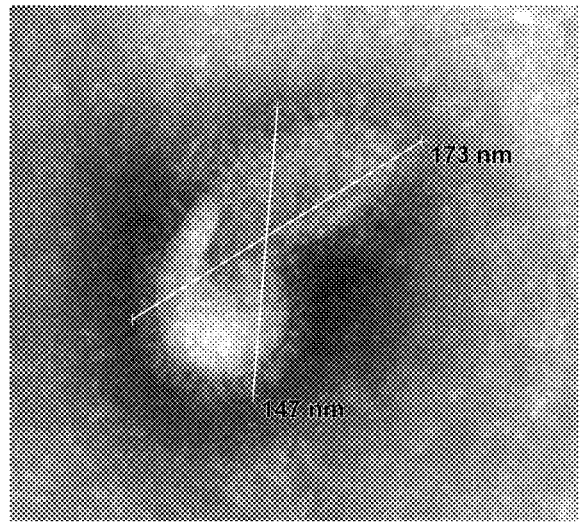
Figure 7C:
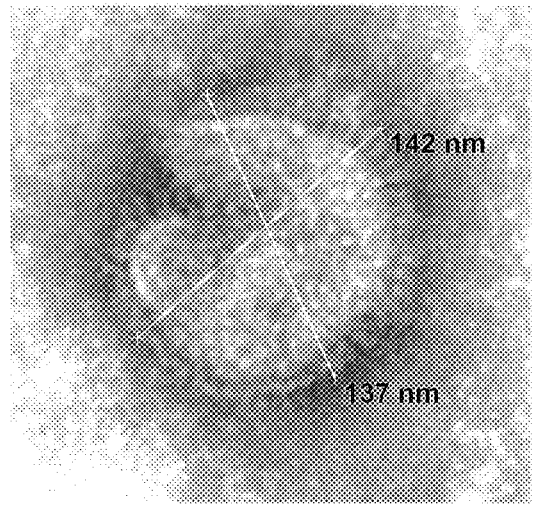
Figure 7D:
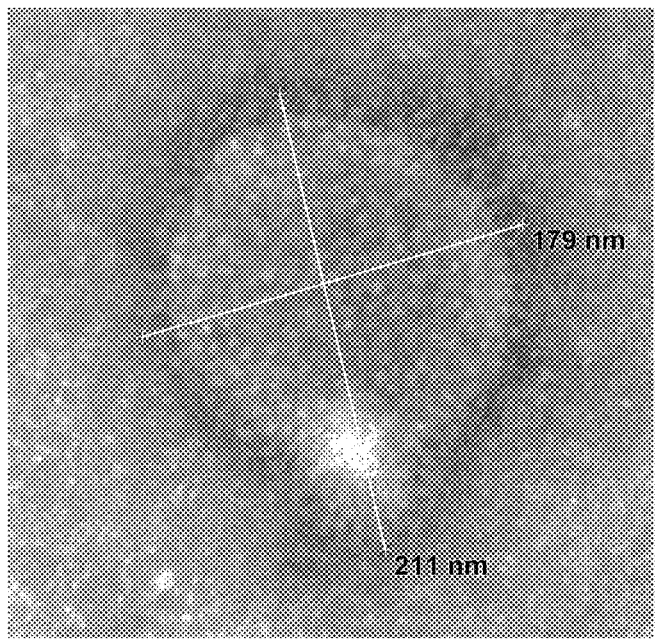

In electronphotomicrographs, virions produced by recombinant influenza viruses prepared with a gene segment 7 with a G52C mutation appeared elongated, filamentous, and much larger than those virions produced by recombinant influenza viruses comprising a wild-type gene segment 7. Electron photomicrographs from three representative virions comprising a gene segment 7 with a G52C mutation are shown in FIG. 7B to FIG. 7D. The virion in the electron photomicrograph shown in FIG. 7B measured 173×147 nm; the virion in the electron photomicrograph shown in FIG. 7C measured 142×137; and the virion in the electron photomicrograph shown in FIG. 7D measured 211×179 nm.

Figure 7E:
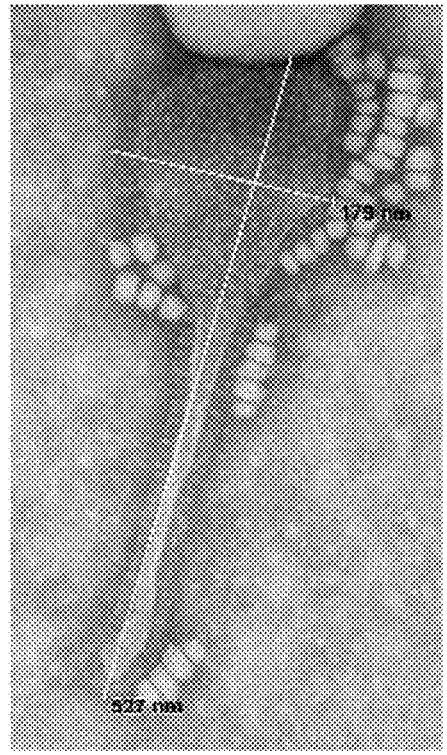
Figure 7F:
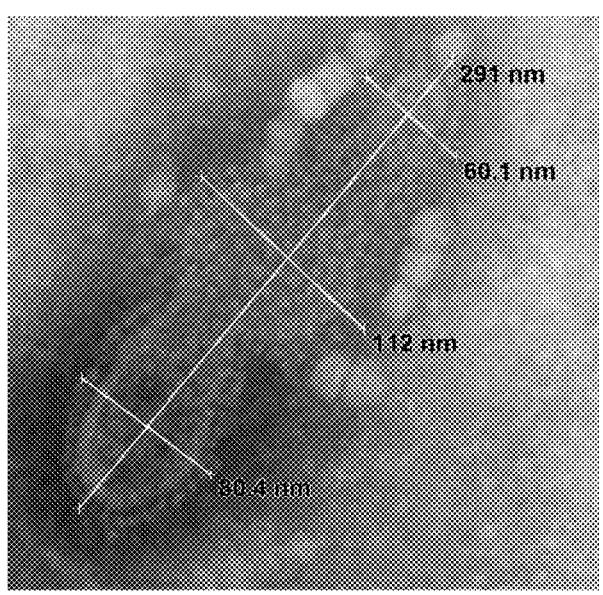
Figure 7G:
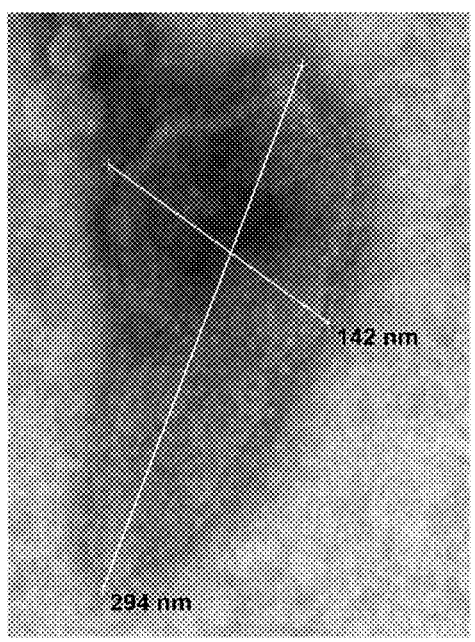

Virions comprising gene segment 7 with a G145A mutation appeared much larger and with varied shapes when compared to those virions comprising wild-type gene segment 7. Virions comprising gene segment 7 with a G145A mutation presented with an uneven and elongated shape. Electron photomicrographs from three representative virions comprising gene segment 7 with a G145A mutation are shown in FIG. 7E to FIG. 7G. The virion in the electro photomicrograph shown in FIG. 7E measured 127×179 nm; the virion in the electron photomicrograph shown in FIG. 7F measured 291×112 nm in the center region, 80.4 nm towards one end, and 60.1 nm towards the other end; and the virion in the electron photomicrograph shown in FIG. 7G presented with an uneven shape and measured 294×142 nm.

Figure 8:
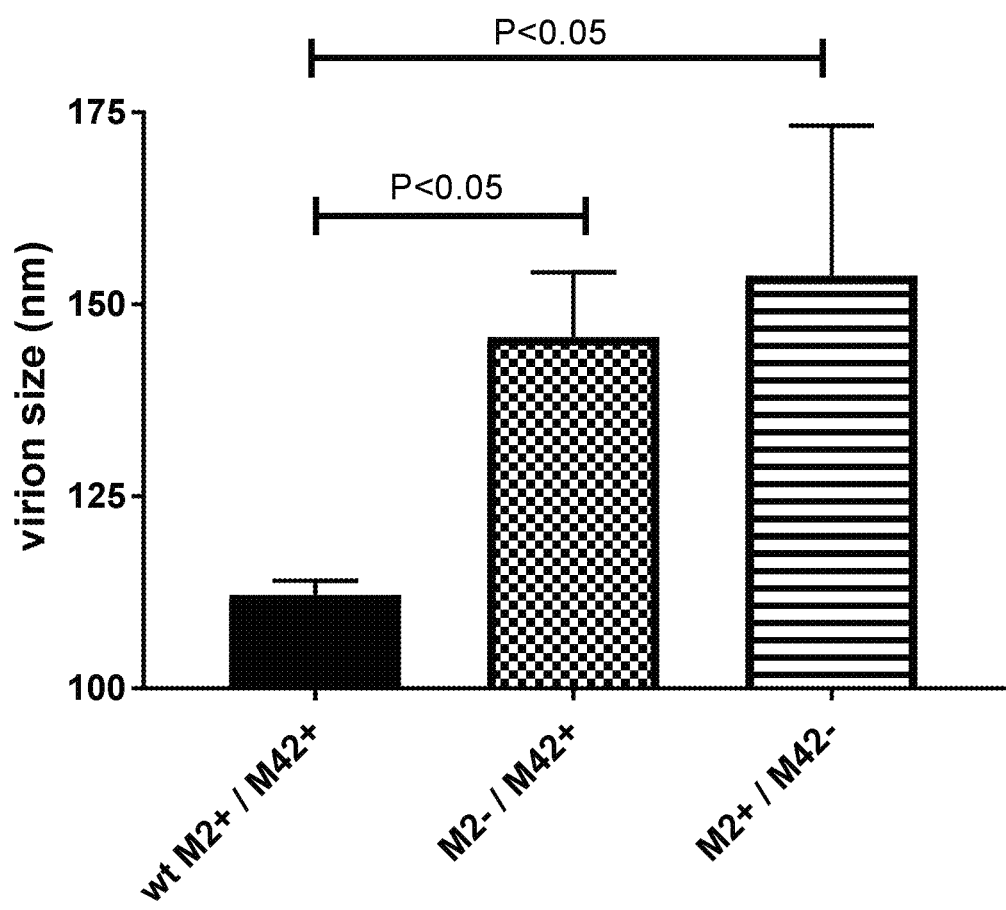
FIG. 8 depicts a graph of virion size of the recombinant influenza A viruses of the invention. The Y axis shows the virion size in nm; the X axis indicates the different virions analyzed. Wt M2+/M42+ are recombinant influenza virus expressing a wild-type gene segment 7. M2−/M42+ are recombinant influenza A virus expressing gene segment 7 with a G52C mutation. M2+/M42− are recombinant influenza A virus expressing gene segment 7 with a G145A mutation. The virion size difference between the viruses having wild-type segment 7 and either one of the two mutants is statistically significant ($P<0.05$).

A graph depicting the average size of the virions comprising wild-type gene segment 7, producing both, M2 protein and M42 protein (M2+/M42+); virions comprising a gene segment 7 with a G52C mutation, producing M42 protein but not M2 protein (M2−/M42+); and virions comprising gene segment 7 with a G145A mutation, producing M2 protein but not M42 protein (M2+/M42−) is shown in FIG. 8. The virion size in nm is presented on the Y axis, and the type of virion produced is shown on the X axis. The statistical difference in size between the M2+/M42+ virus measurements and the M2−/M42+ virus measurements is $P<0.05$. The statistical difference in size between the M2+/M42+ virus measurements and the M2−/M42+ virus measurements is $P<0.05$.

Example 4

Infection and Transmission Study

Contact chickens exposed to birds vaccinated with recombinant influenza viruses comprising gene segment 7 with a G52C mutation or a G145A mutation do not become infected indicating lack of transmission between vaccinated and contact birds and, thus, do not develop an immune response.

For all infection and transmission studies mixed-sex Specific Pathogen-Free (SPF) chickens (White Leghorn egg-layer type) were obtained from and housed at the Southeast Poultry Research Laboratory (SEPRL) in a BSL3E facility. Chickens were maintained in high-efficiency particulate air (HEPA) filtered isolation cabinets with access to feed and water ad libitum. All chicken experimental procedures were approved and performed under the SEPRL Institutional Animal Care and Use Committee.

At 42 days of age, SPF chickens were bled for sera and vaccinated intraocularly and intranasally (IO/IN) with $10^{6.0}$ $EID_{50}$ of one of the three recombinant influenza viruses (M2+/M42+; M2−/M42+; and M2+/M42−) administered in a 0.1 ml volume per route. On day 1 post contact (pc), 2 additional birds (contact birds) were added to the isolators of each virus group for a transmission study. Chickens were observed daily for clinical signs of disease (morbidity and mortality). Oropharyngeal and cloacal swabs were collected daily from all chickens per group. At two weeks post-vaccination, all chickens were bled for sera, and antibody titers were calculated by hemagglutination inhibition (HI) assay. The HI titer results are shown in FIG. 9A to FIG. 9C.

Figure 9A:
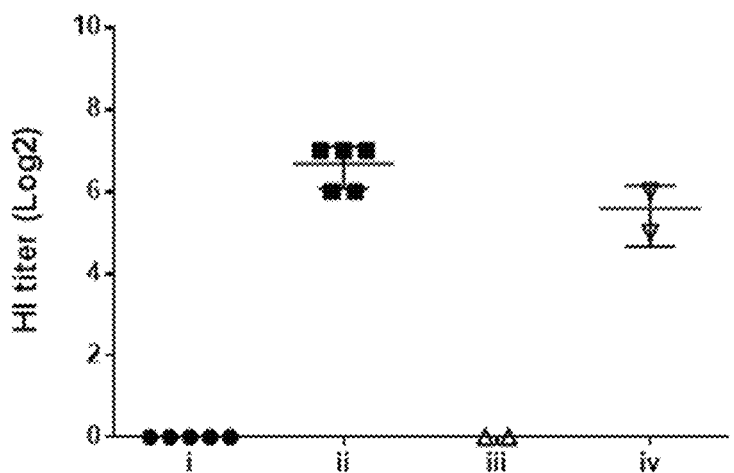
FIG. 9A to FIG. 9C depict graphs of the immune antibody response of chickens (i) pre-vaccination; (ii) 2 weeks-post vaccination; (iii) non-challenged contact birds pre-placement; (iv) non-challenged contact birds 2 weeks-post placement.

The results for chickens treated with or exposed to a recombinant virus comprising a wild-type gene segment 7 are shown in FIG. 9A. No HI titer was detected prior to virus vaccination on treated chickens (i) or prior to contact, on contact chickens (iii). Two weeks post virus challenge the $Log_2$ HI titer on chickens inoculated with recombinant wild type influenza virus containing wild type segment 7 (M2+/M42+) ranged from about 5.5 to about 7 (ii), and the $Log_2$ HI titer on contact placement birds ranged from about 5 to about 6 (iv).

Figure 9B:
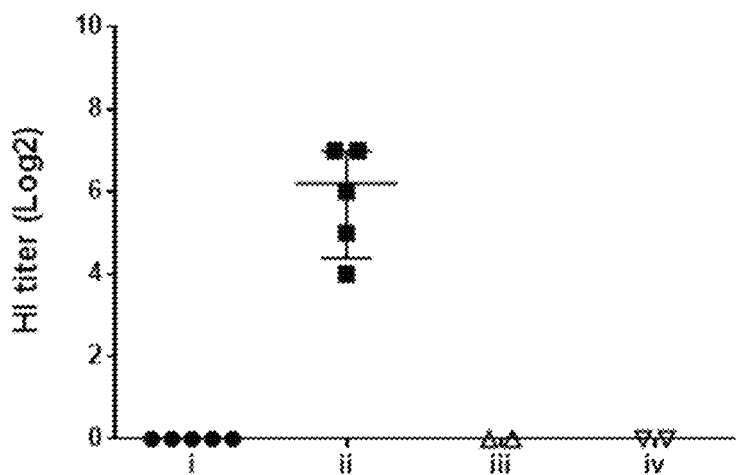

The results for chickens vaccinated with or exposed to a recombinant influenza virus comprising gene segment 7 with a G52C mutation (M2−/M42+) are shown in FIG. 9B. No HI titer was detected on chickens prior to virus vaccination (i), on contact chickens prior to placement (iii), or on contact chickens two weeks post-placement (iv). Two weeks post virus vaccination the $Log_2$ HI titer on chickens vaccinated with the recombinant influenza virus comprising segment 7 with a G52C mutation (M2−/M42+) ranged from about 3 to about 7.5 (ii).

Figure 9C:
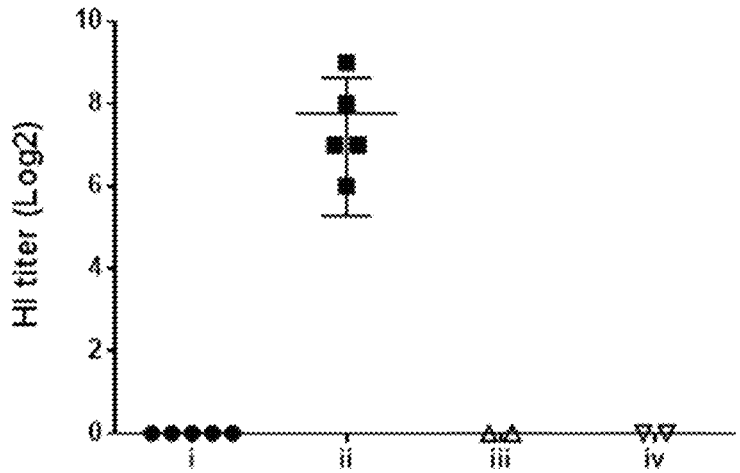

The results for chickens vaccinated with or exposed to a recombinant influenza virus comprising gene segment 7 with a G145A mutation (M2+/M42−) are shown in FIG. 9C. No HI titer was detected on chickens prior to virus vaccination (i), on contact chickens prior to placement (iii), or on contact chickens two weeks post-placement (iv). Two weeks post virus vaccination the $Log_2$ HI titer on chickens inoculated with the recombinant influenza virus comprising segment 7 with a G145A mutation (M2+/M42−) ranged from about 5 to about 9 (ii).

The results above show that recombinant influenza viruses comprising a wild type gene 7 segment, or a gene segment 7 with a G52C mutation or with a G145A mutation induce an immune reaction in vaccinated birds. No immune response was elicited in chickens in contact with the recombinant influenza viruses comprising a mutated gene 7. These results suggest that recombinant influenza viruses comprising a gene segment with a G52C mutation or a G145A mutation are attenuated influenza viruses.

Example 5

Time Course Study

Contact birds exposed to chickens vaccinated with recombinant influenza viruses comprising gene segment 7 with a G52C mutation (M2−/M42+) or a G145A mutation (M2+/M42−) do not induce an immune response. Lack of immune response in contact birds is a result of non-transfer of vaccine virus.

Following the same protocol as in Example 4, chickens were inoculated with recombinant influenza virus comprising a wild-type gene segment 7 (M2+/M42+), comprising a gene segment 7 with a G52C mutation (M2−/M42+), or comprising a gene segment 7 with a G145A mutation (M2+/M42−), and contact birds placed in each virus group. Oral swabs and cloacal swabs were obtained each day for six (6) days post-inoculation.

Oropharyngeal and cloacal swabs were collected in sterile brain heart infusion medium and kept frozen at −70° C. Viral RNA was extracted using Trizol L S reagent (Invitrogen, Carlsbad, Calif.) and the MagMAX AI/ND Viral RNA Isolation Kit (Ambion, Austin, Tex., USA). Quantitative real time RT-PCR (qRRT-PCR) was performed as previously described. Briefly, qRRT-PCR targeting the influenza M gene was conducted using AgPath-ID one-step RT-PCR Kit (Ambion) and the ABI 7500 Fast Real-Time PCR system (Applied Biosystems, Carlsbad, Calif., USA). For viral quantification, a standard curve was established with viral RNA extracted from the titrated challenge virus, A/chicken/Pennsylvania/1370/1983. Results were reported as $EID_{50}$/ml equivalents and the lower limit of detection being $10^{0.9}$ $EID_{50}$/ml for samples from chickens.

Virus titers measured as $\log_{10} EID_{50}$ at days 1 to 6 post challenge in oral swabs are shown in FIG. 10A to FIG. 10F. Viral replication, for all three recombinant virus, was detected in oral swabs of inoculated birds at each day of the experiment FIG. 10A to FIG. 10F (i), (ii), and (iii). In oral swabs of contact on birds placed with chickens vaccinated with recombinant influenza virus comprising wild-type gene segment 7 (M2+/M42+), no virus was detected at day 2 post contact FIG. 10B (iv). In these birds, increasing amounts of virus were detected at each of the additional days FIG. 10C to FIG. 10F (iv). No viral replication was detected at days 2 to 6 post contact in birds placed with chickens vaccinated with recombinant influenza virus comprising gene segment 7 with a G52C mutation (M2−/M42+) or a G145A mutation (M2+/M42−) FIG. 10B to FIG. 10F (v) and (vi). No viral replication was detected in the cloacal samples at any of the time-points tested.

These results show that a virus with a wild type segment 7 is transmitted from vaccinated animals to contact susceptible birds. But, recombinant influenza viruses comprising a gene segment 7 with a G52C mutation (M2−/M42+) or a G145A mutation (M2+/M42−) are not transmitted from vaccinated animals to susceptible birds. These results suggest that recombinant influenza viruses comprising a gene segment 7 with a G52C mutation or a G145A mutation are attenuated viruses, and are potential vaccine candidates.

Example 6

Immune Response and Protective Effects

Recombinant influenza viruses comprising gene segment 7 with a G52C mutation (expressing the M42 polypeptide but not the M2 polypeptide (M2−/M42+)); or comprising gene segment 7 with a G145A mutation (expressing the M2 polypeptide but not the M42 polypeptide (M2+/M42−)) induce an immune response which is protective against subsequent homologous and heterologous virus challenge. This example demonstrates the immune response elicited by the vaccines of the invention is at sufficient level for protection from disease caused by highly pathogenic viruses from the North American lineage (A/Chicken/Pennsylvania/1370/1983 and A/Chicken/Queretaro/14588-19/1995).

At 21 days of age groups of 10 SPF chickens were bled for sera and inoculated with $10^6$ $EID_{50}$ LPAIV via IO/IN route administered in a 0.2 ml volume dose (½ per route). At 42 days of age the birds were bled and challenged with $10^6$ $EID_{50}$ HPAI via IO/IN route. At 56 days of age, all surviving chickens were bled for sera and remaining birds euthanized. Antibody virus titers were calculated by HI.

The experiment set up is summarized in Table 4, below. Vaccine virus 1: rg CK/Penn/83, a wild type H5N2 LPAIV (M2+/M42+); Vaccine V2: rg Ck/Penn/83, the G52C mutant H5N2 LPAIV of the invention (M2−/M42+); Vaccine V3: rg CK/Penn/83, the G145A mutant H5N2 of the invention (M2+/M42−); Sham vaccine: PBS; Challenge V5: A/Ck/Penn/1370/1983 H5N2 HPAIV; Challenge V6: A/Ck/Queretaro/1995 H5N2 HPAIV.

TABLE 4

Experiment Design

| | | Age (days) | | |
|---|---|---|---|---|
| Group # | Group | 21 | 42 | 56 |
| 1 | rg Ck/Penn/83 H5N2 LPAIV WT | Vaccine V1 | Chall V5 | Term |
| 2 | rg Ck/Penn/83 H5N2 LPAIV G52C | Vaccine V2 | Chall V5 | Term |
| 3 | rg Ck/Penn/83 H5N2 LPAIV G145A | Vaccine V3 | Chall V5 | Term |
| 4 | Sham | PBS | Chall V5 | Term |
| 5 | rg Ck/Penn/83 H5N2 LPAIV WT | Vaccine V1 | Chall V6 | Term |
| 6 | rg Ck/Penn/83 H5N2 LPAIV G52C | Vaccine V2 | Chall V6 | Term |
| 7 | rg Ck/Penn/83 H5N2 LPAIV G145A | Vaccine V3 | Chall V6 | Term |
| 8 | Sham | PBS | Chall V6 | Term |

As seen in FIG. 11A and FIG. 11B, all sham inoculated birds died, and all birds vaccinated with a recombinant influenza virus comprising gene segment 7 with a G52C mutation, or comprising gene segment 7 with a G145A mutation survived for the length of the experiment. Regardless of the challenge strain, birds inoculated with wild type rg Chicken/Pennsylvania/1370/83 also survived for the length of the experiment.

Birds were challenged with the homologous highly pathogenic H5N2 influenza A virus A/Chicken/Penn/1370/1983. Shedding was measured in swabs obtained from oral and cloacal swabs two (2) and four (4) days post-challenge. As seen in FIG. 12A to FIG. 12D all sham-inoculated birds shed high titers of virus at days 2 and 4 post challenge. In contrast, significant lower levels of virus were shed by challenged birds vaccinated with a recombinant influenza virus comprising gene segment 7 with a G52C mutation, or comprising gene segment 7 with a G145A mutation.

Birds were challenged with the heterologous highly pathogenic H5N2 influenza A virus A/Chicken/Queretaro/14588-19/1994. Shedding was measured in swabs obtained from oral and cloacal swabs two (2) and four (4) days post-challenge. As seen in FIG. 13A to FIG. 13D all sham inoculated birds shed high titers of virus at days 2 and 4 post challenge. In contrast, significant lower levels of virus were shed by challenged birds vaccinated with a recombinant influenza virus comprising gene segment 7 with a G52C mutation, or comprising gene segment 7 with a G145A mutation. Similar results were obtained with the birds from groups 1 and 5, where the birds survived the length of the experiment, and shed significantly lower levels of virus than sham inoculated birds.

Figure 14:
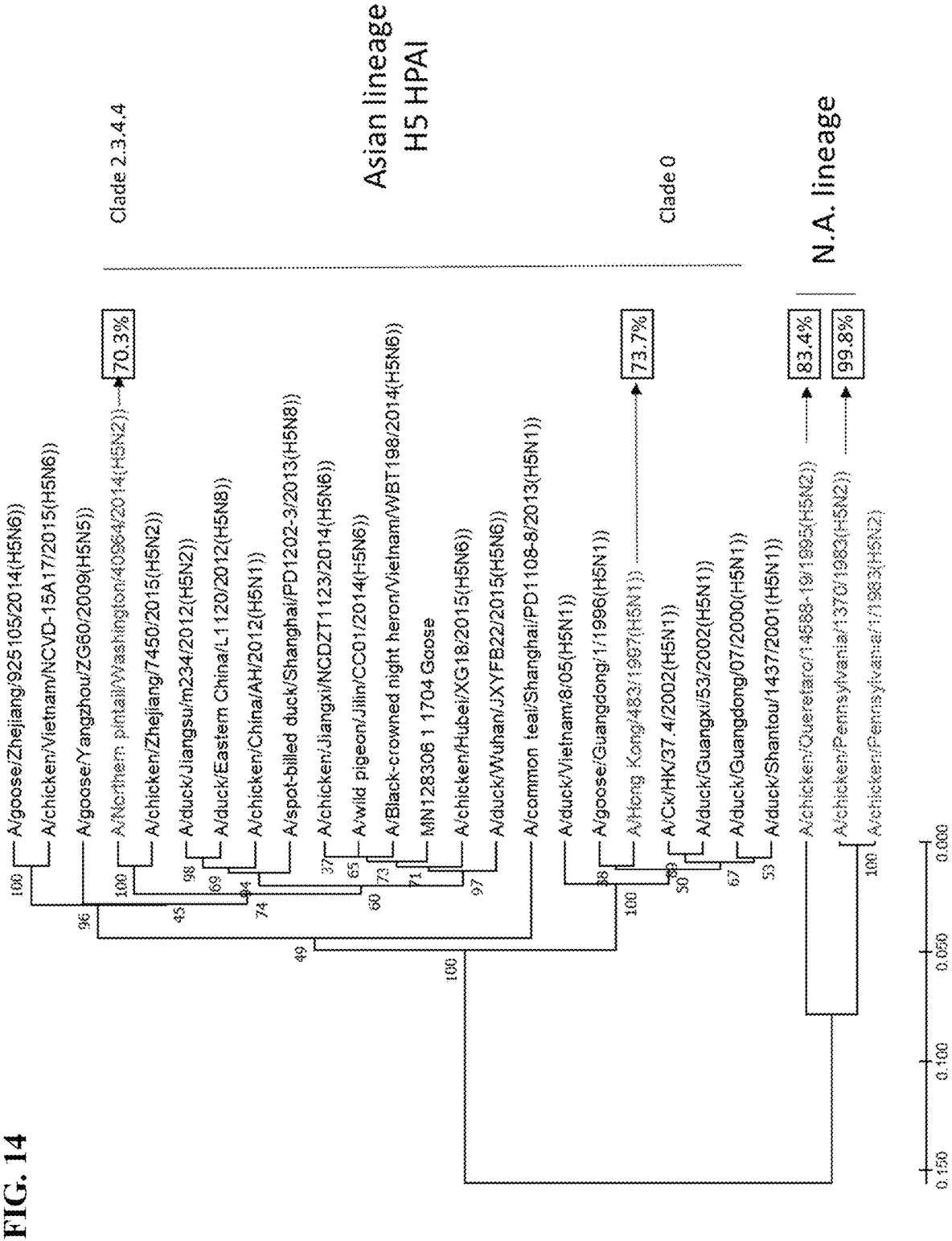
FIG. 14 depicts a phylogenetic tree of the hemagglutinin gene of Influenza viruses. The tree is rooted to A/Chicken/Pennsylvania/1/1983 (H5N2). The boxed numbers present the percent similarity between the HA from A/Chicken/Pennsylvania/1/1983 and the virus to its left. The three viruses listed at the bottom of the figure are from the North American Lineage, and the remaining viruses are from the Asian Lineage.

A phylogenetic tree of the hemagglutinin gene of highly pathogenic influenza viruses is shown in FIG. 14. The tree is rooted to A/Chicken/Pennsylvania/1/1983. As seen in the figure, the HA from A/Chicken/Pennsylvania/1370/1983 has 99.8% similarity to the root virus HA, and the HA from A/Chicken/Queretaro/14588-19/1995 has 83.4 similarity to the root virus HA. All three viruses are H5N2 viruses, and are from the North American lineage.

The results in this example show that the recombinant, live attenuated viruses of the invention protect birds against challenge by homologous and heterologous influenza viruses of the North American lineage.

Example 7

Protection Against Challenge with Asian-Lineage Influenza Virus

Recombinant influenza viruses comprising a wild type gene segment 7, or a gene segment 7 with a G52C mutation (expressing the M42 polypeptide but not the M2 polypeptide (M2−/M42+)); or a gene segment 7 with a G145A mutation (expressing the M2 polypeptide but not the M42 polypeptide (M2+/M42−)) induce an immune response which is protective against subsequent heterologous virus challenge with highly pathogenic viruses of the Asian lineage.

A phylogenetic tree of the hemagglutinin gene of highly pathogenic influenza viruses is shown in FIG. 14. In this figure, the percent similarity between the hemagglutinin gene from A/Ck/Penn/1/193, an H5N2 and the hemagglutinin gene from other viruses is indicated. The HA from A//Hong Kong/483/1997, an H5N1 virus, has 73.7% similarity to the root virus HA, and the HA from A/Northern Pintail/Washington/40964/2014, an H5N2 virus, has 70.3% similarity to the root virus HA.

Figure 15B:
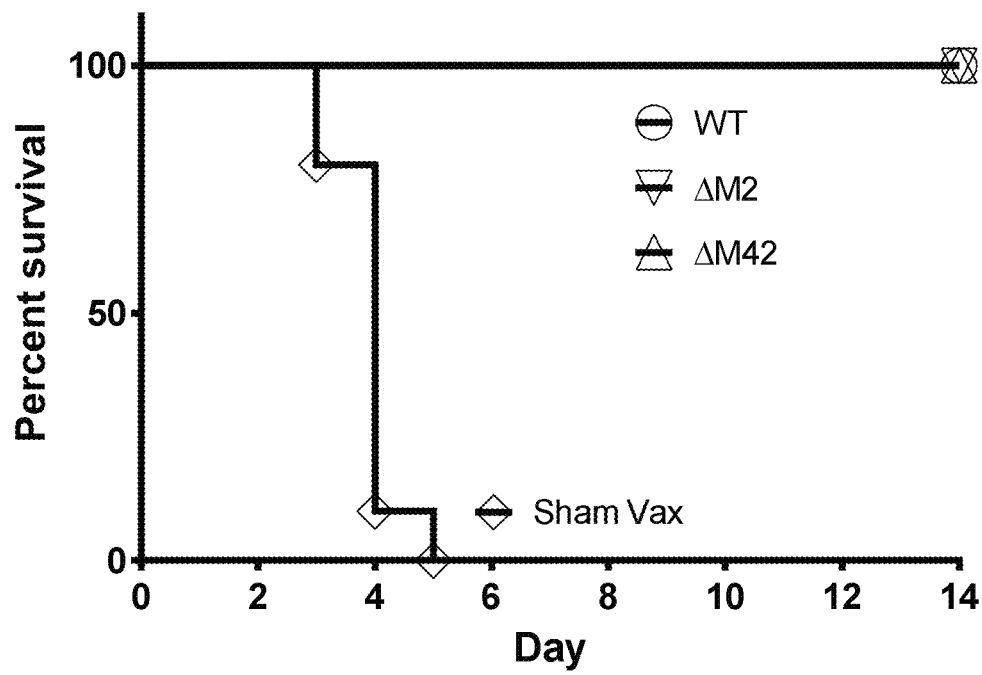

Inoculation and challenge were performed as in Example 6, above. As seen in FIG. 15A and FIG. 15B, all sham inoculated birds died, and all birds vaccinated with a recombinant influenza virus comprising a wild type gene segment 7, or a gene segment 7 with a G52C mutation, or with a G145A mutation survived for the length of the experiment.

Birds were challenged with the heterologous highly pathogenic H5N1 influenza A virus A//Hong Kong/483/1997. Shedding was measured in swabs obtained from oral and cloacal swabs two (2) and four (4) days post-challenge. As seen in FIG. 16A to FIG. 16D all sham-inoculated birds shed high titers of virus at days 2 and 4 post challenge. In contrast, significant lower levels of virus were shed by challenged birds vaccinated with a recombinant influenza virus comprising a wild type gene 7, a gene segment 7 with a G52C mutation, or a gene segment 7 with a G145A mutation.

Birds were challenged with the heterologous highly pathogenic H5N2 influenza A virus A/Northern Pintail/Washington/40964/2014. Shedding was measured in swabs obtained from oral and cloacal swabs two (2) and four (4) days post-challenge. As seen in FIG. 17A to FIG. 17D all sham-inoculated birds shed high titers of virus at days 2 and 4 post challenge. In contrast, significant lower levels of virus were shed by challenged birds vaccinated with a recombinant influenza virus comprising a wild type gene 7, a gene segment 7 with a G52C mutation, or a gene segment 7 with a G145A mutation.

The results in this example show that birds inoculated with a recombinant influenza vaccine comprising wild type gene segment 7, a gene segment 7 with a G52C mutation, or a gene segment 7 with a G145A mutation are protected against viruses from a different lineage, and that contain a HA protein with at least 70% similarity.

Example 8

Comparison of Live Attenuated Vaccine with Killed Vaccine

Live recombinant influenza vaccines of the invention protected birds better from challenge with the highly pathogenic A/CK/Pennsylvania/1370/83 virus better than did killed vaccines prepared with the same recombinant influenza viruses.

The recombinant influenza viruses prepared in Example 1 were inactivated (killed) by 0.1% beta-propiolactone treatment the recombinant influenza viruses prepared in Example 1, above. Inactivation of avian influenza is performed by adding BPL to final concentration of 0.1% and mixing for 1 minute. The virus is transferred to a clean tube, sealed and mixed for 4-6 hours at ambient room temperature. The vial is kept at 4° C. overnight and adjusted to pH 7.0 with 7.5% sodium bicarbonate. The virus is safety tested for inactivation of virus before use. The killed vaccines were than mixed into SEPPIC MONTANIDE ISA 70 emulsion (registered mark of Societe d'Exploitation de Produits pour les Industries Chimiques SEPPIC société anonyme (sa), Paris, France) containing 70% oil adjuvant with 30% aqueous killed virus containing 512 hemagglutinin units per dose At 28 days of age groups of 10 SPF chickens were bled for sera and inoculated with $10^6$ $EID_{50}$ either live-attenuated or killed recombinant influenza virus vaccine via IO/IN route administered in a 0.2 ml volume dose (½ per route). At 49 days of age the birds were bled and challenged with $10^6$ $EID_{50}$ highly pathogenic A/Pennsylvania via IO/IN route. At 56 days of age, all surviving chickens were bled for sera and remaining birds euthanized. Antibody virus titers were calculated by HI.

Birds were challenged with the A/Chicken/Pennsylvania/1/1983, H5N2 influenza A virus Shedding was measured in swabs obtained from oral and cloacal swabs two (2) and four (4) days post-challenge. As seen in FIG. 18A to FIG. 18D all sham-inoculated birds shed high titers of virus at days 2 and 4 post challenge. In contrast, lower levels of virus were shed at day 2 by challenged birds vaccinated with a killed recombinant influenza virus comprising a wild type gene segment 7, a gene segment with a with a G52C mutation, or a gene segment 7 with a G145A mutation. The virus levels shed were even lower at day 4 post-challenge.

The results in this example show that killed and live recombinant influenza virus vaccines protect against challenge. The results also show that there is an increase in viral shedding in challenged birds vaccinated with the killed recombinant vaccine as compared to challenged birds vaccinated with a live recombinant vaccine.

Example 9

Mutation Rate of Influenza Virus Vaccines of the Invention

Only random mutations were observed in the recombinant influenza viruses of the invention, indicating that the introduced mutations are stable.

To examine the mutation rates within the vaccines, New Generation Sequencing (NGS) was performed on oral swab samples from chickens vaccinated with recombinant influenza viruses comprising a wild type gene segment 7 (M2+/M42+), a gene segment 7 with a G52C mutation (M2−/M42+), or a G145A mutation (M2+/M42−). The relative frequency of mutation in each influenza gene segment was determined. To be considered a mutation, the mutation would have at least 5% minimum variant frequency, and at least 1000 minimum coverage. Approximately $10^4$ $EID_{50}$ are needed to use NGS.

Oral swabs from 23 chickens vaccinated with recombinant influenza virus comprising a wild type gene segment 7 were analyzed. In these samples 98 mutations were detected, which resulted in 54 amino acid changes. Oral swabs from 12 chickens vaccinated with recombinant influenza virus comprising a gene segment 7 with a G52C mutation were analyzed. In these samples 52 mutations were detected, which resulted in 28 amino acid changes. Oral swabs from 13 chickens vaccinated with recombinant influenza virus comprising a gene segment 7 with a G145A mutation were analyzed. In these samples 33 mutations were detected, which resulted in 19 amino acid changes.

All the mutations observed appeared to be random. The majority of the changes were identified in segment 1 (PB2) and segment 4 (HA). A total of 98 point mutations were detected in the samples from the birds vaccinated with the recombinant influenza virus comprising a wild type gene segment 7, these nucleotide changes resulted in a total of 54 amino acid changes. A total of 58 point mutations were detected in the samples from the birds vaccinated with the recombinant influenza virus comprising a gene segment 7 with a G52C mutation, these nucleotide changes resulted in 28 amino acid changes. A total of 33 point mutations were detected in the samples from the birds vaccinated with the recombinant influenza virus comprising a gene segment 7 with a G145A mutation, these nucleotide changes resulted in 19 amino acid changes. Only three instances of changes at the same residue. In the samples from the birds vaccinated with the recombinant influenza virus comprising a wild type gene segment 7, PB2 nucleotide 250 was mutated twice, and resulted in the same amino acid change. In the samples from the birds vaccinated with the recombinant influenza virus comprising a gene segment 7 with a G52C mutation, HA nucleotide 465 was mutated twice, and M nucleotide 94 was mutated twice. These changes did not result in an amino acid change.

Table 5, below, presents the amino acid substitutions observed per influenza virus segment.

| PB2 | PB1 | PA | HA | NP | NA | M | NS |
|---|---|---|---|---|---|---|---|
| | | | Wild type Segment 7 - M2+ M42+ | | | | |
| 136 R > G | 228 T > I | 670 N > D | 115 E > K | 27 A > T | 390 F > L | 23 S > N | 31 M > V |
| 186 T > I | 344 F > S | | 116 E > G | 47 L > P | | 27 I > V | 59 S > R |
| 187 K > R | 402 S > L | | 124 T > A | 137 M > T | | 36 L > S | 120 L > F |
| 195 D > N | 422 S > P | | 214 V > A | 176 S > P | | 46 L > I | 200 R > G |
| 203 V > A | 546 M > K | | 294 C > G | 193 L > S | | 68 A > V | |
| 250 V > A | 640 V > A | | 369 S > R | 256 L > P | | 94 D > G | |
| 250 V > A | 667 I > T | | 371 E > K | 290 D > G | | 166 V > M | |
| 262 A > V | | | 382 S > P | 450 N > S | | 168 T > A | |
| 531 Y > F | | | 494 V > I | | | 199 A > T | |
| 551 Q > R | | | 494 V > A | | | | |
| 576 E > G | | | 505 S > P | | | | |
| 654 P > S | | | | | | | |
| 739 R > Q | | | | | | | |
| | | | Segment 7 with G52C mutation - M2− M42+ | | | | |
| 252 N > D | | 367 > K | 118 K > E | 197 I > T | 172 V > A | 76 Y −> C | |
| 276 P > L | | | 210 S > P | 223 C > Y | | 94 D > M | |
| 416 G > S | | | 222 N > D | 235 Q > R | | 95 R > G | |
| 670 K > R | | | 254 A > V | 241 Q > P | | 106 E > G | |
| 730 D > G | | | 291 D > N | 367 S > T | | | |
| 741 S > P | | | 444 M > I | 408 V > I | | | |
| | | | 448 R > K | | | | |
| | | | 465 R > L | | | | |
| | | | 465 R > Q | | | | |
| | | | 493 S > G | | | | |
| | | | Segment 7 with G145A mutation - M2+ M42− | | | | |
| 79 S > I | | 611 S > C | 55 G > E | 224 N > K | | 154 I > V | 88 R > C |
| 83 D > N | | | 327 L > M | 316 I > F | | 189 M > K | 138 F > S |
| 125 L > Q | | | 399 D > G | 352 V > A | | | |
| 273 S > A | | | 483 Y > C | | | | |
| 342 E > G | | | | | | | |
| 446 F > L | | | | | | | |
| 646 R > K | | | | | | | |

The data in this example shows that viruses comprising the mutant recombinant gene 7 segment comprising a G52C mutation or a G145A mutation do not mutate to revert to wild type, but only random mutations are observed.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention.

All publications, patents, and patent applications mentioned in this specification are herein incorporated by reference to the same extent as if each individual publication, patent, or patent application was specifically and individually indicated to be incorporated by reference.

We claim:

1. An HA-specific influenza virus live attenuated vaccine comprising a mutant recombinant influenza virus gene segment 7 with a single mutation of a G to C at a nucleotide corresponding to position 52 of the Influenza A/Chicken/Penn/1/1983 gene segment 7 (G52C mutation) or a single mutation of a G to A at a nucleotide corresponding to position 145 of the Influenza A/Chicken/Penn/1/1983 gene segment 7 (G145A mutation) wherein the vaccine virus does not jump between vaccinated hosts.

2. The HA-specific influenza virus live attenuated vaccine of claim 1, wherein the recombinant influenza virus gene segment 7 has a G52C mutation.

3. The HA-specific influenza live virus attenuated vaccine of claim 1, wherein the recombinant influenza virus gene segment 7 has a G145A mutation.

4. A cell expressing the HA-specific influenza virus live attenuated vaccine of claim 1.

5. The cell of claim 4, wherein the cell is selected from the group consisting of MDCK cells, Vero cells, CV-1 cells, LLcomk.2 cells, MDBK cells, BK-1 cells, Chinese Hamster Ovary cells, 293T cells, human embryonic cells, avian embryonic cells, or in ovo.

6. A composition comprising the HA-specific influenza virus live attenuated vaccine of claim 1, and optionally an adjuvant.

7. The composition of claim 6, wherein the mutant recombinant influenza virus gene segment 7 in the HA-specific influenza virus live attenuated vaccine has a G52C mutation.

8. The composition of claim 6, wherein the mutant recombinant influenza virus gene segment 7 in the HA-specific influenza virus live attenuated vaccine has a G145A mutation.

9. The composition of claim 6, wherein the composition comprises an adjuvant.

10. Use of the HA-specific influenza virus live attenuated vaccine of claim 1 for treatment of influenza in a vertebrate.

11. The use of claim 10, wherein the vertebrate is selected from the group consisting of birds, Canidae, Cetacea, Felidae, Mustelidae, Rodentia, Equidae, Bovidae, Suidae, and Primates.

12. The use of claim 11, wherein the birds are selected from the group consisting of water fowl, chickens, and turkeys.

13. The use of claim 10, wherein the vertebrate is a mammal.

14. The use of claim 13, wherein the mammal is selected from pigs, horses, whales, dolphins, and humans.

15. An HA-specific influenza virus live attenuated vaccine comprising a recombinant influenza virus comprising a PA viral gene segment, a PB1 viral gene segment, a PB2 viral gene segment, an HA viral gene segment, an NA viral gene segment, an NP viral gene segment, an NS viral gene segment having coding sequences for NS1 and NS2, and an M viral gene segment, wherein the viral M gene segment has a G52C mutation or a G145A mutation as compared to the viral M gene segment of wild type Influenza A virus, wherein the vaccine virus does not jump between vaccinated hosts.

16. The HA-specific influenza virus live attenuated vaccine of claim 15, wherein the wild-type M gene segment is from Influenza A/Chicken/Penn/1/1983; A/chicken/Queretaro/14588_19/1995; A/goose/Guangdong/3/1997; A/equine/newMarket/1/77; A/equine/Kentucky/1/1991; A/equine/Tennessee/27A/2014; A/canine/Kentucky/20170606; A/canine/Guangxi/LZ56/2015; A/canine/New_York/1623.1/2010; A/Brevig_Mission/1/1918; A/California/VRDL363/2009; or A/Idaho/19/2018.

17. The HA-specific influenza virus live attenuated vaccine of claim 1, wherein the gene segment 7 encodes an amino acid sequence of SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQID NO: 16; SEQID NO: 17; SEQID NO: 18; SEQID NO: 19; SEQID NO: 20; SEQID NO: 21; SEQID NO: 22; SEQID NO: 23; SEQID NO: 24; SEQID NO: 25; SEQID NO: 26; or SEQ ID NO: 27.

* * * * *

SEQUENCE LISTING

<160> NUMBER OF SEQ ID NOS: 27

<210> SEQ ID NO 1
<211> LENGTH: 1027
<212> TYPE: DNA
<213> ORGANISM: Influenza A virus

<400> SEQUENCE: 1

```
agcaaaagca ggtagatatt taaagatgag tcttctaacc gaggtcgaaa cgtacgttct      60
ctctatcgtc ccgtcaggcc ccctcaaagc cgagatcgcg cagagacttg aagatgtctt     120
tgcagggaaa aacactgatc ttgaggtact tatggaatgg ctaaagacaa gaccaatcct     180
gtcacctctg actaagggga ttttaggatt tgtatttacg ctcaccgtgc ccagtgagcg     240
aggactgcag cgtagacgct ttgtccaaaa tgccctcaat gggaatgggg atccaaacaa     300
catggacaga gcagtcaagc tatacaggaa gctcaaaaga gaaataacat tccatggggc     360
aaaggaagtg gcactcagtt attcaactgg tgcacttgcc agttgcatgg gcctcatata     420
caacagaatg gggactgtga ccaccgaagt ggcatttggc ctggtgtgcg ccacatgtga     480
gcagattgct gattcccagc accggtccca cagacagatg gtgacaacaa tcaacccact     540
aatcaggcat gagaatagaa tggtactagc aagcactacg gctaaagcca tggagcaaat     600
ggcagggtca agtgagcaag cagcagaggc tatggaggtt gctagtcagg ctagacagat     660
ggtgcatgca atgaggacca ttgggactca tcctagttcc agtgctggtc taagagatga     720
tcttcttgaa aatttgcagg cttaccagaa acggatggga gtgcaaatgc agcgattcaa     780
gtgatcctct cattatcgca gcgagtatca ttgggatctt gcacttgata ttgtggattc     840
ttgatcgtct tttcttcaaa tgcatttatc gtcgccttaa atacggtttg aaaagagggc     900
cttctacgga aggagcgcct gagtctatga gggaagaata tcggcaggaa cagcagagtg     960
ctgtggatgt tgacgatgtt catttgtca acatagagct ggagtaaaaa actaccttgt    1020
ttctact                                                            1027
```

<210> SEQ ID NO 2
<211> LENGTH: 99
<212> TYPE: PRT
<213> ORGANISM: Artificial Sequence
<220> FEATURE:
<223> OTHER INFORMATION: Chemically Synthesized

<400> SEQUENCE: 2

```
Met Ser Leu Gln Gly Lys Thr Leu Ile Leu Arg Leu Thr Arg Asn Gly
1               5                   10                  15

Trp Glu Cys Lys Cys Ser Asp Ser Asp Pro Leu Ile Ile Ala Ala
            20                  25                  30

Ser Ile Ile Gly Ile Leu His Leu Ile Leu Trp Ile Leu Asp Arg Leu
        35                  40                  45

Phe Phe Lys Cys Ile Tyr Arg Arg Leu Lys Tyr Gly Leu Lys Arg Gly
    50                  55                  60
```

```
Pro Ser Thr Glu Gly Ala Pro Glu Ser Met Arg Glu Tyr Arg Gln
 65                  70                  75                  80

Glu Gln Gln Ser Ala Val Asp Val Asp Asp Val His Phe Val Asn Ile
                 85                  90                  95

Glu Leu Glu

<210> SEQ ID NO 3
<211> LENGTH: 97
<212> TYPE: PRT
<213> ORGANISM: Artificial Sequence
<220> FEATURE:
<223> OTHER INFORMATION: Chemically Synthesized

<400> SEQUENCE: 3

Met Ser Leu Leu Thr Glu Val Glu Thr Leu Thr Arg Asn Gly Trp Glu
 1               5                  10                  15

Cys Lys Cys Ser Asp Ser Ser Asp Pro Leu Ile Ile Ala Ala Ser Ile
                20                  25                  30

Ile Gly Ile Leu His Leu Ile Leu Trp Ile Leu Asp Arg Leu Phe Phe
             35                  40                  45

Lys Cys Ile Tyr Arg Arg Leu Lys Tyr Gly Leu Lys Arg Gly Pro Ser
         50                  55                  60

Thr Glu Gly Ala Pro Glu Ser Met Arg Glu Tyr Arg Gln Glu Gln
 65                  70                  75                  80

Gln Ser Ala Val Asp Val Asp Asp Val His Phe Val Asn Ile Glu Leu
                 85                  90                  95

Glu

<210> SEQ ID NO 4
<211> LENGTH: 1027
<212> TYPE: DNA
<213> ORGANISM: Artificial Sequence
<220> FEATURE:
<223> OTHER INFORMATION: Chemically Synthesized

<400> SEQUENCE: 4
agcaaaagca ggtagatatt taaagatgag tcttctaacc gaggtcgaaa cctacgttct     60
ctctatcgtc ccgtcaggcc ccctcaaagc cgagatcgcg cagagacttg aagatgtctt    120
tgcagggaaa acactgatc ttgaggtact tatggaatgg ctaaagacaa gaccaatcct    180
gtcacctctg actaagggga ttttaggatt tgtatttacg ctcaccgtgc ccagtgagcg    240
aggactgcag cgtagacgct ttgtccaaaa tgccctcaat gggaatgggg atccaaacaa    300
catggacaga gcagtcaagc tatacaggaa gctcaaaaga gaaataacat tccatggggc    360
aaaggaagtg gcactcagtt attcaactgg tgcacttgcc agttgcatgg cctcatata    420 caacagaatg gggactgtga ccaccgaagt ggcatttggc ctggtgtgcg ccacatgtga    480
gcagattgct gattcccagc accggtccca cagacagatg gtgacaacaa tcaacccact    540
aatcaggcat gagaatagaa tggtactagc aagcactacg gctaaagcca tggagcaaat    600
ggcagggtca agtgagcaag cagcagaggc tatggaggtt gctagtcagg ctagacagat    660
ggtgcatgca atgaggacca ttgggactca tcctagttcc agtgctggtc taagagatga    720
tcttcttgaa aatttgcagg cttaccagaa acggatggga gtgcaaatgc agcgattcaa    780
gtgatcctct cattatcgca gcgagtatca ttgggatctt gcacttgata ttgtggattc    840
ttgatcgtct tttcttcaaa tgcatttatc gtcgccttaa atacggtttg aaaagagggc    900
```
cttctacgga aggagcgcct gagtctatga gggaagaata tcggcaggaa cagcagagtg    960
ctgtggatgt tgacgatgtt cattttgtca acatagagct ggagtaaaaa actaccttgt   1020
ttctact                                                             1027

<210> SEQ ID NO 5
<211> LENGTH: 1027
<212> TYPE: DNA
<213> ORGANISM: Artificial Sequence
<220> FEATURE:
<223> OTHER INFORMATION: Chemically Synthesized

<400> SEQUENCE: 5
agcaaaagca ggtagatatt taaagatgag tcttctaacc gaggtcgaaa cgtacgttct     60
ctctatcgtc ccgtcaggcc ccctcaaagc cgagatcgcg cagagacttg aagatgtctt    120
tgcagggaaa aacactgatc ttgaagtact tatggaatgg ctaaagacaa gaccaatcct    180
gtcacctctg actaagggga ttttaggatt tgtatttacg ctcaccgtgc ccagtgagcg    240
aggactgcag cgtagacgct ttgtccaaaa tgccctcaat gggaatgggg atccaaacaa    300
catggacaga gcagtcaagc tatacaggaa gctcaaaaga gaaataacat tccatggggc    360
aaaggaagtg gcactcagtt attcaactgg tgcacttgcc agttgcatgg gcctcatata    420
caacagaatg gggactgtga ccaccgaagt ggcatttggc ctggtgtgcg ccacatgtga    480
gcagattgct gattcccagc accggtccca cagacagatg gtgacaacaa tcaacccact    540
aatcaggcat gagaatagaa tggtactagc aagcactacg gctaaagcca tggagcaaat    600
ggcagggtca agtgagcaag cagcagaggc tatggaggtt gctagtcagg ctagacagat    660
ggtgcatgca atgaggacca ttgggactca tcctagttcc agtgctggtc taagagatga    720
tcttcttgaa aatttgcagg cttaccagaa acggatggga gtgcaaatgc agcgattcaa    780
gtgatcctct cattatcgca gcgagtatca ttgggatctt gcacttgata ttgtggattc    840
ttgatcgtct tttcttcaaa tgcatttatc gtcgccttaa atacggtttg aaaagagggc    900
cttctacgga aggagcgcct gagtctatga gggaagaata tcggcaggaa cagcagagtg    960
ctgtggatgt tgacgatgtt cattttgtca acatagagct ggagtaaaaa actaccttgt   1020
ttctact                                                             1027

<210> SEQ ID NO 6
<211> LENGTH: 1027
<212> TYPE: DNA
<213> ORGANISM: Artificial Sequence
<220> FEATURE:
<223> OTHER INFORMATION: Chemically Synthesized

<400> SEQUENCE: 6
agcaaaagca ggtagatatt gaaagatgag tcttctaacc gaggtcgaaa cctacgttct     60
ctctatcgtc ccgtcaggcc ccctcaaagc cgagatcgcg cagagacttg aagatgtctt    120
tgcagggaag aacaccgatc ttgaggcact catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa cgcccttaat gggaatgggg atccaaacaa    300
catggacaga gcagtcaaac tgtacaggaa gctaaaaagg gaaataacat tccatggagc    360
aaaagaagtg gcactcagtt actcagctgg tgcacttgcc agttgcatgg gcctcatata    420
caacagaatg gggactgtga ccaccgaagt ggcatttggc ctggtgtgcg ccacatgtga    480
gcaaattgct gattcccagc atcggtctca cagacaaatg gtgacaacaa ccaacccact    540

-continued

```
gattagacat gaaaacagaa tggtgctggc cagtactacg gcaaaagcca tggagcaaat    600
ggcagggtca agtgaacagg cagcagaagc tatggaggtt gctagtcagg ctagacagat    660
ggtgcaggca atgagaacga ttggaaccca tcctagctcc agtgctggtt aaaagatga    720 tcttcttgaa aatttgcagg cctaccagaa acggatggga gtgcaaatgc agcgattcaa    780
gtgatcctct cgttattgcc gcaaacatca ttgggatctt gcacttgata ttgtggattc    840
ttgatcgtct tttcttcaaa tgcatctatc gtcgctttaa atacggtttg aaaagagggc    900
cttctacgga aggagtgcct gaatctatga gggaagaata tcggcaggaa cagcagagtg    960
ctgtggatgt tgacgatggt cattttgtca acatagagct ggagtaaaaa actaccttgt   1020
ttctact                                                             1027
```

<210> SEQ ID NO 7
<211> LENGTH: 1027
<212> TYPE: DNA
<213> ORGANISM: Artificial Sequence
<220> FEATURE:
<223> OTHER INFORMATION: Chemically Synthesized

<400> SEQUENCE: 7

```
agcaaaagca ggtagatatt gaaagatgag tcttctaacc gaggtcgaaa cgtacgttct     60
ctctatcgtc ccgtcaggcc ccctcaaagc cgagatcgcg cagagacttg aagatgtctt    120
tgcagggaag aacaccgatc ttgaagcact catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa cgcccttaat gggaatgggg atccaaacaa    300
catggacaga gcagtcaaac tgtacaggaa gctaaaaagg gaataacat tccatggagc    360 aaaagaagtg gcactcagtt actcagctgg tgcacttgcc agttgcatgg gcctcatata    420
caacagaatg gggactgtga ccaccgaagt ggcatttggc ctggtgtgcg ccacatgtga    480
gcaaattgct gattcccagc atcggtctca cagacaaatg gtgacaacaa ccaacccact    540
gattagacat gaaaacagaa tggtgctggc cagtactacg gcaaaagcca tggagcaaat    600
ggcagggtca agtgaacagg cagcagaagc tatggaggtt gctagtcagg ctagacagat    660
ggtgcaggca atgagaacga ttggaaccca tcctagctcc agtgctggtt aaaagatga    720 tcttcttgaa aatttgcagg cctaccagaa acggatggga gtgcaaatgc agcgattcaa    780
gtgatcctct cgttattgcc gcaaacatca ttgggatctt gcacttgata ttgtggattc    840
ttgatcgtct tttcttcaaa tgcatctatc gtcgctttaa atacggtttg aaaagagggc    900
cttctacgga aggagtgcct gaatctatga gggaagaata tcggcaggaa cagcagagtg    960
ctgtggatgt tgacgatggt cattttgtca acatagagct ggagtaaaaa actaccttgt   1020
ttctact                                                             1027
```

<210> SEQ ID NO 8
<211> LENGTH: 985
<212> TYPE: DNA
<213> ORGANISM: Artificial Sequence
<220> FEATURE:
<223> OTHER INFORMATION: Chemically Synthesized

<400> SEQUENCE: 8

```
aagatgagtc ttctaaccga ggtcgaaacc tacgttctct ctatcgtccc gtcaggcccc     60
ctcaaagccg agatcgcgca gagacttgaa gatgtctttg caggaaagaa caccgatctc    120
```

```
gaggctctca tggaatggct aaagacaaga ccaatcctgt cacctctgac taaagggatt      180
ttaggatttg tgttcacgct caccgtgccc agtgagcgag gactgcagcg tagacgcttt      240
gtccagaatg ccttaaatgg aaatggagat ccaaacaata tggatagggc agttaagcta      300
tacaagaagc tgaaaagaga ataacattc catgggcta aggaggtcgc actcagctac        360
tcaaccggtg cacttgccag ttgtatgggt ctcatataca acaggatggg aacggtgacc      420
acagaagtgg cttttggcct agtgtgtgcc acttgtgagc agattgcaga ttcacagcat      480
cggtctcaca gacagatggc aactaccacc aacccactaa tcaggcatga aacagaatg      540 gtgccggcca gcactacagc taaggctatg gagcagatgg ctggatcgag tgagcaggca      600
gcggaagcca tggaggttgc tagtcagact aggcagatgg tgcaggcaat gaggacaatt      660
gggactcatc ctagctccag tgccggtctg aaagataatc ttcttgaaaa tttgcaggcc      720
caccagaaac gaatgggagt gcaaatgcag cgattcaagt gatcctcttg ttgttgccgc      780
aagtatcatt gggatcttgc acttgatatt gtggattctt gatcgtcttt tcttcaaatg      840
catttatcgt cgccttaaat acggtttgaa agagggcct tctatggaag gggtacctgg      900
gtctatgagg aagagtatc ggcaggaaca gcagagtgct gtggatgttg acgatggtca      960
ttttgtcaac atagagctgg agtaa                                            985
```

<210> SEQ ID NO 9
<211> LENGTH: 985
<212> TYPE: DNA
<213> ORGANISM: Artificial Sequence
<220> FEATURE:
<223> OTHER INFORMATION: Chemically Synthesized

<400> SEQUENCE: 9

```
aagatgagtc ttctaaccga ggtcgaaacg tacgttctct ctatcgtccc gtcaggcccc       60
ctcaaagccg agatcgcgca gagacttgaa gatgtctttg caggaaagaa caccgatctc      120
gaagctctca tggaatggct aaagacaaga ccaatcctgt cacctctgac taaagggatt      180
ttaggatttg tgttcacgct caccgtgccc agtgagcgag gactgcagcg tagacgcttt      240
gtccagaatg ccttaaatgg aaatggagat ccaaacaata tggatagggc agttaagcta      300
tacaagaagc tgaaaagaga ataacattc catgggcta aggaggtcgc actcagctac        360
tcaaccggtg cacttgccag ttgtatgggt ctcatataca acaggatggg aacggtgacc      420
acagaagtgg cttttggcct agtgtgtgcc acttgtgagc agattgcaga ttcacagcat      480
cggtctcaca gacagatggc aactaccacc aacccactaa tcaggcatga aacagaatg      540 gtgccggcca gcactacagc taaggctatg gagcagatgg ctggatcgag tgagcaggca      600
gcggaagcca tggaggttgc tagtcagact aggcagatgg tgcaggcaat gaggacaatt      660
gggactcatc ctagctccag tgccggtctg aaagataatc ttcttgaaaa tttgcaggcc      720
caccagaaac gaatgggagt gcaaatgcag cgattcaagt gatcctcttg ttgttgccgc      780
aagtatcatt gggatcttgc acttgatatt gtggattctt gatcgtcttt tcttcaaatg      840
catttatcgt cgccttaaat acggtttgaa agagggcct tctatggaag gggtacctgg      900
gtctatgagg aagagtatc ggcaggaaca gcagagtgct gtggatgttg acgatggtca      960
ttttgtcaac atagagctgg agtaa                                            985
```

<210> SEQ ID NO 10
<211> LENGTH: 982
<212> TYPE: DNA
<213> ORGANISM: Artificial Sequence

```
<220> FEATURE:
<223> OTHER INFORMATION: Chemically Synthesized

<400> SEQUENCE: 10
atgagtcttc tgaccgaggt cgaaacctac gttctctcta tcgtaccatc aggcccctc      60 aaagccgaga tcgcgcagag acttgaagat gtctttgcag gaaagaacac cgatcttgag    120
gcactcatgg aatggctaaa gacaagacca atcctgtcac ctctgactaa ggggatttta    180
ggatttgtgt tcacgctcac cgtgcccagt gagcgaggac tgcagcgtag acgctttgtc    240
caaaatgccc ttaatgggaa cggagatcca acaacatgg  acagagcagt aaaactgtac    300
aggaagctta aagggaaat  aacattccat ggggcaaaag aggtggcact cagctattcc    360
actggtgcac tagccagctg catgggactc atatacaaca gaatggggac tgtgacaacc    420
gaagtggcat ttggcctggt atgcgccaca tgtgaacaga ttgctgattc ccagcaccga    480
tctcacagac agatggtgac aacaaccaac ccactaatca gacacgagaa cagaatggta    540
ctagccagta ccacagctaa agccatggag cagatggcag gtcgagtga  gcaggcagca    600 gaggccatgg aggttgctag tcaggccagg cagatggtgc aggcaatgag aaccattggg    660
acccacccta gctccagtgc cggttttgaaa aatgatcttc ttgaaaattt gcaggcctac    720
cagaaacgga tgggagtgca aatgcagcga ttcaagtgat cctctcgtta ttgcagcaag    780
tatcattggg atcttgcact tgatattgtg gattcttgat cgtctttttct tcaaatgcat    840 ttatcgtcgt cttaaatacg gtttgaaaag agggccttct acggaaggag tacctgagtc    900
tatgagggaa gaatatcggc aggaacagca gagtgctgtg gatgttgacg atggtcattt    960
tgtcaacata gagctggagt aa                                             982

<210> SEQ ID NO 11
<211> LENGTH: 982
<212> TYPE: DNA
<213> ORGANISM: Artificial Sequence
<220> FEATURE:
<223> OTHER INFORMATION: Chemically Synthesized

<400> SEQUENCE: 11
atgagtcttc tgaccgaggt cgaaacgtac gttctctcta tcgtaccatc aggcccctc      60 aaagccgaga tcgcgcagag acttgaagat gtctttgcag gaaagaacac cgatcttgaa    120
gcactcatgg aatggctaaa gacaagacca atcctgtcac ctctgactaa ggggatttta    180
ggatttgtgt tcacgctcac cgtgcccagt gagcgaggac tgcagcgtag acgctttgtc    240
caaaatgccc ttaatgggaa cggagatcca acaacatgg  acagagcagt aaaactgtac    300
aggaagctta aagggaaat  aacattccat ggggcaaaag aggtggcact cagctattcc    360
actggtgcac tagccagctg catgggactc atatacaaca gaatggggac tgtgacaacc    420
gaagtggcat ttggcctggt atgcgccaca tgtgaacaga ttgctgattc ccagcaccga    480
tctcacagac agatggtgac aacaaccaac ccactaatca gacacgagaa cagaatggta    540
ctagccagta ccacagctaa agccatggag cagatggcag gtcgagtga  gcaggcagca    600 gaggccatgg aggttgctag tcaggccagg cagatggtgc aggcaatgag aaccattggg    660
acccacccta gctccagtgc cggttttgaaa aatgatcttc ttgaaaattt gcaggcctac    720
cagaaacgga tgggagtgca aatgcagcga ttcaagtgat cctctcgtta ttgcagcaag    780
tatcattggg atcttgcact tgatattgtg gattcttgat cgtctttttct tcaaatgcat    840 ttatcgtcgt cttaaatacg gtttgaaaag agggccttct acggaaggag tacctgagtc    900
```

| | |
|---|---|
| tatgagggaa gaatatcggc aggaacagca gagtgctgtg gatgttgacg atggtcattt | 960 |
| tgtcaacata gagctggagt aa | 982 |

<210> SEQ ID NO 12
<211> LENGTH: 990
<212> TYPE: DNA
<213> ORGANISM: Artificial Sequence
<220> FEATURE:
<223> OTHER INFORMATION: Chemically Synthesized

<400> SEQUENCE: 12

| | |
|---|---|
| tttaaagatg agtcttctga ccgaggtcga aacctacgtt ctctctatcg taccatcagg | 60 |
| cccccctcaaa gccgagatcg cgcagagact tgaagatgtc tttgcaggga agaacaccga | 120 |
| tcttgaggca ctcatggaat ggctaaagac aagaccaatc ctgtcacctc tgactaaagg | 180 |
| gattttagga ttcgtattca cgctcaccgt gcccagtgag cgaggactgc agcgtagacg | 240 |
| ctttgtccaa aatgcccttta gtggaaacgg agatccaaac aacatggaca gagcagtaaa | 300 |
| actgtacagg aagcttaaaa gagaaataac attccatggg gcaaaagagg tggcactcag | 360 |
| ctattccact ggtgcactag ccagctgcat gggactcata caacagaa tgggaactgt | 420 |
| gacaaccgaa gtggcatttg gcctggtatg cgccacatgt gaacagatcg ctgattccca | 480 |
| gcatcgatct cacaggcaga tggtgacaac aaccaaccca ttaatcagac atgaaaacag | 540 |
| aatggtatta gccagtacca cggctaaagc catggagcag atggcagggt cgagtgagca | 600 |
| ggcagcagag gccatggagg ttgctagtaa ggctaggcag atggtacagg caatgagaac | 660 |
| cattgggacc caccctagct ccagtgccgg tttgaaagat gatctccttg aaaatttgca | 720 |
| ggcctaccag aaacggatgg gagtgcaaat gcagcgattc aagtgatcct ctcgttattg | 780 |
| cagcaagtat cattgggatc ttgcacttga tattgtggat tcttgatcgc cttttcttca | 840 |
| aattcattta tcgtcgcctt aaatacgggt tgaaagagg gccttctacg aaggagtac | 900 |
| ctgagtctat gagggaagaa atatcggcagg aacagcagaa tgctgtggat gttgacgatg | 960 |
| gtcattttgt caacatagag ctggagtaaa | 990 |

<210> SEQ ID NO 13
<211> LENGTH: 990
<212> TYPE: DNA
<213> ORGANISM: Artificial Sequence
<220> FEATURE:
<223> OTHER INFORMATION: Chemically Synthesized

<400> SEQUENCE: 13

| | |
|---|---|
| tttaaagatg agtcttctga ccgaggtcga aacgtacgtt ctctctatcg taccatcagg | 60 |
| cccccctcaaa gccgagatcg cgcagagact tgaagatgtc tttgcaggga agaacaccga | 120 |
| tcttgaagca ctcatggaat ggctaaagac aagaccaatc ctgtcacctc tgactaaagg | 180 |
| gattttagga ttcgtattca cgctcaccgt gcccagtgag cgaggactgc agcgtagacg | 240 |
| ctttgtccaa aatgcccttta gtggaaacgg agatccaaac aacatggaca gagcagtaaa | 300 |
| actgtacagg aagcttaaaa gagaaataac attccatggg gcaaaagagg tggcactcag | 360 |
| ctattccact ggtgcactag ccagctgcat gggactcata caacagaa tgggaactgt | 420 |
| gacaaccgaa gtggcatttg gcctggtatg cgccacatgt gaacagatcg ctgattccca | 480 |
| gcatcgatct cacaggcaga tggtgacaac aaccaaccca ttaatcagac atgaaaacag | 540 |
| aatggtatta gccagtacca cggctaaagc catggagcag atggcagggt cgagtgagca | 600 |
| ggcagcagag gccatggagg ttgctagtaa ggctaggcag atggtacagg caatgagaac | 660 |

```
cattgggacc cacccctagct ccagtgccgg tttgaaagat gatctccttg aaaatttgca    720
ggcctaccag aaacggatgg gagtgcaaat gcagcgattc aagtgatcct ctcgttattg    780
cagcaagtat cattgggatc ttgcacttga tattgtggat tcttgatcgc ctttttcttca   840 aattcattta tcgtcgcctt aaatacgggt tgaaaagagg gccttctacg gaaggagtac    900
ctgagtctat gagggaagaa tatcggcagg aacagcagaa tgctgtggat gttgacgatg    960
gtcattttgt caacatagag ctggagtaaa                                      990
```

<210> SEQ ID NO 14
<211> LENGTH: 1027
<212> TYPE: DNA
<213> ORGANISM: Artificial Sequence
<220> FEATURE:
<223> OTHER INFORMATION: Chemically Synthesized

<400> SEQUENCE: 14

```
agcaaaagca ggtagatatt taaagatgag tcttctaacc gaggtcgaaa cctacgttct     60
ctctatcatg ccatcaggcc ccctcaaagc cgagatcgcg cagagacttg aagatgtctt    120
tgcagggaag aacaccgatc ttgaggcact catggaatgg ctaaagacaa gaccaatcct    180
gtcacctcta actaaaggga ttttaggatt tgtattcacg ctcaccgtgc ccagtgagcg    240
aggactgcag cgtagacgct ttgtccaaaa tgcccttagt ggaaacggag atccaaacaa    300
catggacaga gcggtaaaac tgtacaggaa gcttaaaaga gaataacat tccatggggc    360 aaaagaggtg gcactcagct attccactgg tgcactagcc agctgcatgg gactcatata    420
caacagaatg ggaactgtta caaccgaagt ggcatttggc ctggtatgtg ccacatgtga    480
acagattgct gattcccagc accggtctca taggcagatg gtgacaacaa ccaacccatt    540
aatcagacat gaaaacagaa tggtattagc cagtaccacg gctaaagcca tggaacagat    600
ggcaggatca agtgagcagg cagcagaggc catggaggtt gctagtaggg ctaggcagat    660
ggtacaggca atgagaacca tgggacccca tcctagctcc agtgctggtt tgaaagatga    720
tctccttgaa aacttacagg cctaccagaa acggatggga gtgcaaatgc agcgattcaa    780
gtgatcctct cgttattgca gcaagtatca ttgggatatt gcacttgata ttgtggattc    840
ttgatcgtct tttcttcaaa ttcatttatc gtcgccttaa atacgggatg aaaagagggc    900
cttctacgga aggagtacct gagtctatga gggaagaata tcggcaggaa cagcagaatg    960
ctgtggatgt tgacgatggt cattttgtca acatagagct agagtaaaaa actaccttgt   1020
ttctact                                                              1027
```

<210> SEQ ID NO 15
<211> LENGTH: 1027
<212> TYPE: DNA
<213> ORGANISM: Artificial Sequence
<220> FEATURE:
<223> OTHER INFORMATION: Chemically Synthesized

<400> SEQUENCE: 15

```
agcaaaagca ggtagatatt taaagatgag tcttctaacc gaggtcgaaa cgtacgttct     60
ctctatcatg ccatcaggcc ccctcaaagc cgagatcgcg cagagacttg aagatgtctt    120
tgcagggaag aacaccgatc ttgaagcact catggaatgg ctaaagacaa gaccaatcct    180
gtcacctcta actaaaggga ttttaggatt tgtattcacg ctcaccgtgc ccagtgagcg    240
aggactgcag cgtagacgct ttgtccaaaa tgcccttagt ggaaacggag atccaaacaa    300
```

| catggacaga | gcggtaaaac | tgtacaggaa | gcttaaaaga | gaaataacat | tccatggggc | 360 |
| aaaagaggtg | gcactcagct | attccactgg | tgcactagcc | agctgcatgg | gactcatata | 420 |
| caacagaatg | ggaactgtta | caaccgaagt | ggcatttggc | ctggtatgtg | ccacatgtga | 480 |
| acagattgct | gattcccagc | accggtctca | taggcagatg | gtgacaacaa | ccaacccatt | 540 |
| aatcagacat | gaaaacagaa | tggtattagc | cagtaccacg | gctaaagcca | tggaacagat | 600 |
| ggcaggatca | agtgagcagg | cagcagaggc | catggaggtt | gctagtaggg | ctaggcagat | 660 |
| ggtacaggca | atgagaacca | ttgggaccca | tcctagctcc | agtgctggtt | tgaaagatga | 720 |
| tctccttgaa | aacttacagg | cctaccagaa | acggatggga | gtgcaaatgc | agcgattcaa | 780 |
| gtgatcctct | cgttattgca | gcaagtatca | ttgggatatt | gcacttgata | ttgtggattc | 840 |
| ttgatcgtct | tttcttcaaa | ttcatttatc | gtcgccttaa | atacgggatg | aaaagagggc | 900 |
| cttctacgga | aggagtacct | gagtctatga | gggaagaata | tcggcaggaa | cagcagaatg | 960 |
| ctgtggatgt | tgacgatggt | cattttgtca | acatagagct | agagtaaaaa | actaccttgt | 1020 |
| ttctact | | | | | | 1027 |

<210> SEQ ID NO 16
<211> LENGTH: 1027
<212> TYPE: DNA
<213> ORGANISM: Artificial Sequence
<220> FEATURE:
<223> OTHER INFORMATION: Chemically Synthesized

<400> SEQUENCE: 16

| agcaaaagca | ggtagatatt | gaaagatgag | tcttctaacc | gaggtcgaaa | cctacgttct | 60 |
| ctctatcatc | ccatcaggcc | ccctcaaagc | cgagatcgcg | cagagacttg | aagatgtctt | 120 |
| tgcagggaaa | aacaccgatc | tcgaggctct | catggaatgg | ctaaagacaa | gaccaatcct | 180 |
| gtccccttta | actaaggga | ttttaggatt | tgtgttcacg | ctcaccgtgc | ccagtgagcg | 240 |
| aggactgcag | cgtagacgct | ttgtccaaaa | tgccctaaat | gggaatggag | acccaaacaa | 300 |
| catggacaag | gcagtcaaac | tgtacaggaa | gttgaaaaga | gagataacat | tccacggggc | 360 |
| taaagaagtt | gcactcagct | actcaaccgg | tgcacttgcc | agttgtatgg | gtctcatata | 420 |
| caacaggatg | ggaacagtga | ccacagaagt | ggcttttggc | ctagtgtgtg | ccacctgtga | 480 |
| acagattgct | gattcacagc | atcggtccca | caggcagatg | gtaactacca | ctaacccact | 540 |
| aatcaggcat | gaaaacagga | tggtgctagc | cagcaccaca | gctaaggcta | tggagcagat | 600 |
| ggctgggtcg | agtgagcagg | cagcagaagc | catggaggtt | gccaatcagg | ctaggcagat | 660 |
| ggtgcaagca | atgaggacaa | ttggaactca | ccctagctcc | agtgccggtc | taaaagatga | 720 |
| tcttcttgaa | aacttgcagg | cctaccagaa | acgaatggga | gtgcaaatgc | agcgatttaa | 780 |
| gtgatcctct | cattattgcc | gcaagtatca | ttggaatctt | gcacttgata | ttgtggattc | 840 |
| ttgatcgtct | tttcttcaaa | tgtatttatc | gtcgccttaa | atacggtttg | aaaagagggc | 900 |
| cttctacgga | aggagtgcct | gagtctatga | gggaagagta | tcggcaggaa | cagcagagtg | 960 |
| ctgtggatgt | tgacgatggt | cattttgtca | acatagagct | ggagtaaaaa | actaccttgt | 1020 |
| ttctact | | | | | | 1027 |

<210> SEQ ID NO 17
<211> LENGTH: 1027
<212> TYPE: DNA
<213> ORGANISM: Artificial Sequence
<220> FEATURE:
<223> OTHER INFORMATION: Chemically Synthesized

<400> SEQUENCE: 17

```
agcaaaagca ggtagatatt gaaagatgag tcttctaacc gaggtcgaaa cgtacgttct    60
ctctatcatc ccatcaggcc ccctcaaagc cgagatcgcg cagagacttg aagatgtctt   120
tgcagggaaa aacaccgatc tcgaagctct catggaatgg ctaaagacaa gaccaatcct   180
gtcaccttta actaagggga ttttaggatt tgtgttcacg ctcaccgtgc ccagtgagcg   240
aggactgcag cgtagacgct ttgtccaaaa tgccctaaat gggaatggag acccaaacaa   300
catggacaag gcagtcaaac tgtacaggaa gttgaaaaga gagataacat tccacggggc   360
taaagaagtt gcactcagct actcaaccgg tgcacttgcc agttgtatgg gtctcatata   420
caacaggatg ggaacagtga ccacagaagt ggcttttggc ctagtgtgtg ccacctgtga   480
acagattgct gattcacagc atcggtccca caggcagatg gtaactacca ctaacccact   540
aatcaggcat gaaaacagga tggtgctagc cagcaccaca gctaaggcta tggagcagat   600
ggctgggtcg agtgagcagg cagcagaagc catggaggtt gccaatcagg ctaggcagat   660
ggtgcaagca atgaggacaa ttggaactca ccctagctcc agtgccggtc taaaagatga   720
tcttcttgaa aacttgcagg cctaccagaa acgaatggga gtgcaaatgc agcgatttaa   780
gtgatcctct cattattgcc gcaagtatca ttggaatctt gcacttgata ttgtggattc   840
ttgatcgtct tttcttcaaa tgtatttatc gtcgccttaa atacggtttg aaaagagggc   900
cttctacgga aggagtgcct gagtctatga gggaagagta tcggcaggaa cagcagagtg   960
ctgtggatgt tgacgatggt cattttgtca acatagagct ggagtaaaaa actaccttgt  1020
ttctact                                                            1027
```

<210> SEQ ID NO 18
<211> LENGTH: 982
<212> TYPE: DNA
<213> ORGANISM: Artificial Sequence
<220> FEATURE:
<223> OTHER INFORMATION: Chemically Synthesized

<400> SEQUENCE: 18

```
atgagtcttc taaccgaggt cgaaacctac gttctttcta tcatcccgtc aggccccctc    60
aaagccgaga tcgcgcagag actggaaagt gtctttgcag gaaagaacac agatcttgag   120
gctctcatgg aatggctaaa gacaagacca atccttgtca ctctgactaa gggaatttta   180
ggatttgtgt tcacgctcac cgtgcccagt gagcgaggac tgcagcgtag acgctttgtc   240
caaaatgcac taaatgggaa tggggacccg aacaacatgg atagagcagt taaactatac   300
aaaaagctca aaagagaaat aacgttccat ggggccaagg aggtgtcact aagctattca   360
actggtgcac ttgccggttg catgggcctc atatacaaca ggatgggaac agtgaccaca   420
gaagctgctt ttggtctagt gtgtgccact tgtgaacaga ttgctgattc acagcatcga   480
tctcacagac aaatggctac taccaccaat ccactaatca ggcatgaaaa cagaatggtg   540
ctggctagca ctacggcaaa ggctatggaa cagatggctg atcgagtgaa caggcagca   600
gaggccatgg aggttgctaa tcagactaga cagatggtac atgcaatgag aactattggg   660
actcatccta gctccagtgc tggtctgaaa gatgaccttc ttgaaaattt gcaggcctac   720
cagaagcgaa tgggagtgca gatgcagcga ttcaagtgat cctctcgtca ttgcagcaaa   780
tatcattgga atcttgcacc tgatattgtg gatcactgat cgtctttttt tcaaatgtat   840
ttatcgtcgc tttaaatacg gtttgaaaag agggccttct acggaaggag tgcctgagtc   900
```

| | |
|---|---|
| catgagggaa gaatatcaac aggaacagca gagtgctgtg gatgttgacg atggtcattt | 960 |
| tgtcaacata gagctagagt aa | 982 |

<210> SEQ ID NO 19
<211> LENGTH: 982
<212> TYPE: DNA
<213> ORGANISM: Artificial Sequence
<220> FEATURE:
<223> OTHER INFORMATION: Chemically Synthesized

<400> SEQUENCE: 19

| | |
|---|---|
| atgagtcttc taaccgaggt cgaaacgtac gttctttcta tcatcccgtc aggcccctc | 60 |
| aaagccgaga tcgcgcagag actggaaagt gtctttgcag gaaagaacac agatcttgaa | 120 |
| gctctcatgg aatggctaaa gacaagacca atcttgtcac ctctgactaa gggaatttta | 180 |
| ggatttgtgt tcacgctcac cgtgcccagt gagcgaggac tgcagcgtag acgctttgtc | 240 |
| caaaatgcac taaatgggaa tgggaccccg aacaacatgg atagagcagt taaactatac | 300 |
| aaaaagctca aagagaaat aacgttccat ggggccaagg aggtgtcact aagctattca | 360 |
| actggtgcac ttgccggttg catgggcctc atatacaaca ggatgggaac agtgaccaca | 420 |
| gaagctgctt ttggtctagt gtgtgccact tgtgaacaga ttgctgattc acagcatcga | 480 |
| tctcacagac aaatggctac taccaccaat ccactaatca ggcatgaaaa cagaatggtg | 540 |
| ctggctagca ctacggcaaa ggctatggaa cagatggctg atcgagtga acaggcagca | 600 |
| gaggccatgg aggttgctaa tcagactaga cagatggtac atgcaatgag aactattggg | 660 |
| actcatccta gctccagtgc tggtctgaaa gatgaccttc ttgaaaattt gcaggcctac | 720 |
| cagaagcgaa tgggagtgca gatgcagcga ttcaagtgat cctctcgtca ttgcagcaaa | 780 |
| tatcattgga atcttgcacc tgatattgtg atcactgat cgtcttttt tcaaatgtat | 840 |
| ttatcgtcgc tttaaatacg gtttgaaaag agggccttct acggaaggag tgcctgagtc | 900 |
| catgagggaa gaatatcaac aggaacagca gagtgctgtg gatgttgacg atggtcattt | 960 |
| tgtcaacata gagctagagt aa | 982 |

<210> SEQ ID NO 20
<211> LENGTH: 1027
<212> TYPE: DNA
<213> ORGANISM: Artificial Sequence
<220> FEATURE:
<223> OTHER INFORMATION: Chemically Synthesized

<400> SEQUENCE: 20

| | |
|---|---|
| agcaaaagca ggtagatatt taaagatgag tcttctaacc gaagtcgaaa cctacgttct | 60 |
| ctctatcata ccatcaggcc ccctcaaagc cgagatcgcg cagagacttg aagatgtctt | 120 |
| tgcgggaaag aacaccgatc ttgaggcact tatggaatgg ctaaagacaa gaccaatcct | 180 |
| gtcacctctg actaaaggga ttttaggatt tgtattcacg ctcaccgtgc ccagtgagcg | 240 |
| aggactgcag cgtagacgct ttgtccaaaa tgcccttagt ggaaacggag atccaaacaa | 300 |
| catggacaga gcagtaaaac tatacaggaa gcttaaaaga gaataacat tccatggggc | 360 |
| aaaagaagtg gcactcagct attccactgg tgcactagcc agttgcatgg gactcatata | 420 |
| caacagaatg ggaactatta caaccgaagt ggcatttggc ctggtatgcg ccacatgtga | 480 |
| acagattgct gattcccagc atcggtctca caggcagatg gtgacaacaa ccaacccatt | 540 |
| aatcagacat gaaaacagaa tggtattagc cagcaccacg gctaaagcca tggaacagat | 600 |
| ggcaggatcg agtgagcaag cagcagaggc catggaggtt gctagtaggg ctaggcagat | 660 |

```
ggtacaggca atgagaacca ttgggaccca ccctagctcc agtgccggtt tgaaagatga    720
tctccttgaa aatttacagg cctaccagaa acggatggga gtgcaaatgc agcgattcaa    780
gtgatcctct cgttactgca gcaagtatca ttgggatctt gcacttgata ttgtggattc    840
ttgatcgtct tttcttcaaa ttcatttatc gtcgccttaa atacgggtta aaaagagggc    900
cttctatgga aggagtacct gagtctatga gggaagaata tcggcaggaa cagcagaatg    960
ctgtggatgt tgacgatggt cattttgtca acatagagct ggagtaaaaa actaccttgt   1020
ttctact                                                             1027
```

<210> SEQ ID NO 21
<211> LENGTH: 1027
<212> TYPE: DNA
<213> ORGANISM: Artificial Sequence
<220> FEATURE:
<223> OTHER INFORMATION: Chemically Synthesized

<400> SEQUENCE: 21

```
agcaaaagca ggtagatatt taaagatgag tcttctaacc gaagtcgaaa cgtacgttct     60
ctctatcata ccatcaggcc ccctcaaagc cgagatcgcg cagagacttg aagatgtctt    120
tgcgggaaag aacaccgatc ttgaagcact tatggaatgg ctaaagacaa gaccaatcct    180
gtcacctctg actaaaggga ttttaggatt tgtattcacg ctcaccgtgc ccagtgagcg    240
aggactgcag cgtagacgct ttgtccaaaa tgcccttagt ggaaacggag atccaaacaa    300
catggacaga gcagtaaaac tatacaggaa gcttaaaaga gaataacat tccatggggc     360 aaaagaagtg gcactcagct attccactgg tgcactagcc agttgcatgg gactcatata    420
caacagaatg gaactatta caaccgaagt ggcatttggc ctggtatgcg ccacatgtga    480
acagattgct gattcccagc atcggtctca caggcagatg gtgacaacaa ccaacccatt    540
aatcagacat gaaaacagaa tggtattagc cagcaccacg gctaaagcca tggaacagat    600
ggcaggatcg agtgagcaag cagcagaggc catggaggtt gctagtaggg ctaggcagat    660
ggtacaggca atgagaacca ttgggaccca ccctagctcc agtgccggtt tgaaagatga    720
tctccttgaa aatttacagg cctaccagaa acggatggga gtgcaaatgc agcgattcaa    780
gtgatcctct cgttactgca gcaagtatca ttgggatctt gcacttgata ttgtggattc    840
ttgatcgtct tttcttcaaa ttcatttatc gtcgccttaa atacgggtta aaaagagggc    900
cttctatgga aggagtacct gagtctatga gggaagaata tcggcaggaa cagcagaatg    960
ctgtggatgt tgacgatggt cattttgtca acatagagct ggagtaaaaa actaccttgt   1020
ttctact                                                             1027
```

<210> SEQ ID NO 22
<211> LENGTH: 982
<212> TYPE: DNA
<213> ORGANISM: Artificial Sequence
<220> FEATURE:
<223> OTHER INFORMATION: Chemically Synthesized

<400> SEQUENCE: 22

```
atgagtcttt taaccgaggt cgaaacctac gttctctcta tcgtcccgtc aggccccctc     60
aaagccgaga tcgcgcagag acttgaagat gtctttgcag gaagaacac cgatcttgag     120 gctctcatgg aatggctaaa gacaagacca atcctgtcac ctctgactaa ggggatttta    180
ggatttgtgt tcacgctcac cgtgcccagt gagcgaggac tgcagcgtag acgctttgtc    240
```

| | |
|---|---|
| caaaatgccc ttaatgggaa cggggatcca aataacatgg acagagcagt taaactgtac | 300 |
| aggaagctta agagggagat aacattccat ggggccaaag aagtagcact cagttattcc | 360 |
| gctggtgcac ttgccagttg tatgggcctc atatacaaca ggatgtgggac tgtgaccact | 420 |
| gaagtggcat ttggcctggt atgcgcaacc tgtgaacaga ttgctgattc ccagcatcgg | 480 |
| tctcacaggc aaatggtgac aacaaccaat ccactaatca gacatgagaa cagaatggta | 540 |
| ctggccagca ctacggctaa ggctatggag caaatggctg gatcgagtga gcaagcagca | 600 |
| gaggccatgg aggttgctag tcaggctagg caaatggtgc aggcgatgag aaccattggg | 660 |
| actcatccta gctccagtgc tggtctgaaa gacgatctta ttgaaaattt gcaggcctac | 720 |
| cagaaacgaa tggggggtgca gatgcaacga ttcaagtgat cctctcgtta ttgccgcaag | 780 |
| tatcattggg atcttgcact tgatattgtg gattcttgat cgtctttttt tcaaatgcat | 840 |
| ttatcgtcgc cttaaatacg gtttgaaaag agggccttct acggaaggag tgccggagtc | 900 |
| tatgagggaa gaatatcgaa aggaacagca gagtgctgtg gatgttgacg atggtcattt | 960 |
| tgtcaacata gagctggagt aa | 982 |

<210> SEQ ID NO 23
<211> LENGTH: 982
<212> TYPE: DNA
<213> ORGANISM: Artificial Sequence
<220> FEATURE:
<223> OTHER INFORMATION: Chemically Synthesized

<400> SEQUENCE: 23

| | |
|---|---|
| atgagtcttt taaccgaggt cgaaacgtac gttctctcta tcgtcccgtc aggccccctc | 60 |
| aaagccgaga tcgcgcagag acttgaagat gtctttgcag ggaagaacac cgatcttgaa | 120 |
| gctctcatgg aatggctaaa gacaagacca atcctgtcac ctctgactaa ggggattta | 180 |
| ggatttgtgt tcacgctcac cgtgcccagt gagcgaggac tgcagcgtag acgctttgtc | 240 |
| caaaatgccc ttaatgggaa cggggatcca aataacatgg acagagcagt taaactgtac | 300 |
| aggaagctta agagggagat aacattccat ggggccaaag aagtagcact cagttattcc | 360 |
| gctggtgcac ttgccagttg tatgggcctc atatacaaca ggatgtgggac tgtgaccact | 420 |
| gaagtggcat ttggcctggt atgcgcaacc tgtgaacaga ttgctgattc ccagcatcgg | 480 |
| tctcacaggc aaatggtgac aacaaccaat ccactaatca gacatgagaa cagaatggta | 540 |
| ctggccagca ctacggctaa ggctatggag caaatggctg gatcgagtga gcaagcagca | 600 |
| gaggccatgg aggttgctag tcaggctagg caaatggtgc aggcgatgag aaccattggg | 660 |
| actcatccta gctccagtgc tggtctgaaa gacgatctta ttgaaaattt gcaggcctac | 720 |
| cagaaacgaa tggggggtgca gatgcaacga ttcaagtgat cctctcgtta ttgccgcaag | 780 |
| tatcattggg atcttgcact tgatattgtg gattcttgat cgtctttttt tcaaatgcat | 840 |
| ttatcgtcgc cttaaatacg gtttgaaaag agggccttct acggaaggag tgccggagtc | 900 |
| tatgagggaa gaatatcgaa aggaacagca gagtgctgtg gatgttgacg atggtcattt | 960 |
| tgtcaacata gagctggagt aa | 982 |

<210> SEQ ID NO 24
<211> LENGTH: 1000
<212> TYPE: DNA
<213> ORGANISM: Artificial Sequence
<220> FEATURE:
<223> OTHER INFORMATION: Chemically Synthesized

<400> SEQUENCE: 24

| | |
|---|---|
| atattgaaag atgagccttc taaccgaggt cgaaacctat gttctctcta tcgttccatc | 60 |
| aggcccctc aaagccgaga tcgcgcagag acttgaagat gtctttgctg ggaaaaacac | 120 |
| agatcttgag gctctcatgg aatggctaaa gacaagacca attctgtcac ctctgactaa | 180 |
| ggggattttg gggtttgtgt tcacgctcac cgtgcccagt gagcgaggac tgcagcgtag | 240 |
| acgctttgtc caaaatgccc tcaatgggaa tggagaccca ataacatgg acaaagcagt | 300 |
| taaactgtat aggaaactta agagggagat aacgttccat ggggccaaag aaatagctct | 360 |
| cagttattct gctggtgcac ttgccagttg catgggcctc atatacaata ggatgggggc | 420 |
| tgtaaccact gaagtggcat ttggcctggt atgtgcaaca tgtgagcaga ttgctgactc | 480 |
| ccagcacagg tctcataggc agatggtggc aacaaccaat ccattaataa acatgagaa | 540 |
| cagaatggtt ttggccagca ctacagctaa ggctatggag caaatggctg atcaagtga | 600 |
| gcaggcagcg gaggccatgg agattgctag tcaggccagg cagatggtgc aggcaatgag | 660 |
| agccattgga actcatccta gttccagtac tggtctaaga gatgatcttc ttgaaaattt | 720 |
| gcagacctat cagaaacgaa tggggtgca gatgcaacga ttcaagtgac ccgcttgttg | 780 |
| ttgccgcgaa tatcattggg atcttgcact tgatattgtg gattcttgat cgtctttct | 840 |
| tcaaatgcgt ctatcgactc ttcaaacacg gccttaaaag aggcccttct acggaaggag | 900 |
| tacctgagtc tatgagggaa gaatatcgaa aggaacagca gaatgctgtg gatgctgacg | 960 |
| acagtcattt tgtcagcata gagttggagt aaaaaactac | 1000 |

<210> SEQ ID NO 25
<211> LENGTH: 1000
<212> TYPE: DNA
<213> ORGANISM: Artificial Sequence
<220> FEATURE:
<223> OTHER INFORMATION: Chemically Synthesized

<400> SEQUENCE: 25

| | |
|---|---|
| atattgaaag atgagccttc taaccgaggt cgaaacgtat gttctctcta tcgttccatc | 60 |
| aggcccctc aaagccgaga tcgcgcagag acttgaagat gtctttgctg ggaaaaacac | 120 |
| agatcttgaa gctctcatgg aatggctaaa gacaagacca attctgtcac ctctgactaa | 180 |
| ggggattttg gggtttgtgt tcacgctcac cgtgcccagt gagcgaggac tgcagcgtag | 240 |
| acgctttgtc caaaatgccc tcaatgggaa tggagaccca ataacatgg acaaagcagt | 300 |
| taaactgtat aggaaactta agagggagat aacgttccat ggggccaaag aaatagctct | 360 |
| cagttattct gctggtgcac ttgccagttg catgggcctc atatacaata ggatgggggc | 420 |
| tgtaaccact gaagtggcat ttggcctggt atgtgcaaca tgtgagcaga ttgctgactc | 480 |
| ccagcacagg tctcataggc agatggtggc aacaaccaat ccattaataa acatgagaa | 540 |
| cagaatggtt ttggccagca ctacagctaa ggctatggag caaatggctg atcaagtga | 600 |
| gcaggcagcg gaggccatgg agattgctag tcaggccagg cagatggtgc aggcaatgag | 660 |
| agccattgga actcatccta gttccagtac tggtctaaga gatgatcttc ttgaaaattt | 720 |
| gcagacctat cagaaacgaa tggggtgca gatgcaacga ttcaagtgac ccgcttgttg | 780 |
| ttgccgcgaa tatcattggg atcttgcact tgatattgtg gattcttgat cgtctttct | 840 |
| tcaaatgcgt ctatcgactc ttcaaacacg gccttaaaag aggcccttct acggaaggag | 900 |
| tacctgagtc tatgagggaa gaatatcgaa aggaacagca gaatgctgtg gatgctgacg | 960 |
| acagtcattt tgtcagcata gagttggagt aaaaaactac | 1000 |

<210> SEQ ID NO 26
<211> LENGTH: 1002
<212> TYPE: DNA
<213> ORGANISM: Artificial Sequence
<220> FEATURE:
<223> OTHER INFORMATION: Chemically Synthesized

<400> SEQUENCE: 26

| | |
|---|---|
| tagatgttta aagatgagtc ttctaaccga ggtcgaaacc tacgttcttt ctatcatccc | 60 |
| gtcaggcccc ctcaaagccg agatcgcaca gagactggaa agtgtctttg caggaaagaa | 120 |
| cacagatctt gaggctctca tggaatggct aaagacaaga ccaatcttgt cacctctgac | 180 |
| taagggaatt ttaggatttg tgttcacgct caccgtgccc agtgagcgag gactgcagcg | 240 |
| tagacgcttt atccaaaatg ccctaaatgg aaatggggac ccgaacaaca tggatagagc | 300 |
| agttaaacta tacaagaagc tcaaaagaga ataacgttc catggggcca aggaggtgtc | 360 |
| actaagctat tcaactggtg cacttgcaag ttgcatgggc ctcatataca acaggatggg | 420 |
| aacagtgacc acagaagctg ctttcggtct agtttgtgcc acttgtgaac agattgctga | 480 |
| ttcacagcat cggtctcaca gacaaatggc tactaccaca aatccactaa tcaggcatga | 540 |
| aaacagaatg gtgctggcta gcactacggc aaaggctatg aacaggtgg ctggatcgag | 600 |
| tgaacaggca gcggaggcca tggaggttgc taataagact aggcagatgg tacatgcaat | 660 |
| gagaactatt gggactcatc ctagctccag tgctggtctg agagatgacc ttcttgaaaa | 720 |
| tttgcaggcc taccagaagc ggatgggagt gcagatgcag cggttcaagt gatcctctcg | 780 |
| tcattgcagc aaacatcatt gggatcttgc acctgatatt gtggattact gatcgtcttt | 840 |
| ttttcaaatg catttatcgt cgctttaaat acggtctgaa agagggcct tctacggaag | 900 |
| gagtgcctga gtccatgagg gaagaatatc aacaggagca gcagagtgct gtggatgttg | 960 |
| acgatggtca ttttgtcaac atagagctag agtaaaaaac ta | 1002 |

<210> SEQ ID NO 27
<211> LENGTH: 1002
<212> TYPE: DNA
<213> ORGANISM: Artificial Sequence
<220> FEATURE:
<223> OTHER INFORMATION: Chemically Synthesized

<400> SEQUENCE: 27

| | |
|---|---|
| tagatgttta aagatgagtc ttctaaccga ggtcgaaacg tacgttcttt ctatcatccc | 60 |
| gtcaggcccc ctcaaagccg agatcgcaca gagactggaa agtgtctttg caggaaagaa | 120 |
| cacagatctt gaagctctca tggaatggct aaagacaaga ccaatcttgt cacctctgac | 180 |
| taagggaatt ttaggatttg tgttcacgct caccgtgccc agtgagcgag gactgcagcg | 240 |
| tagacgcttt atccaaaatg ccctaaatgg aaatggggac ccgaacaaca tggatagagc | 300 |
| agttaaacta tacaagaagc tcaaaagaga ataacgttc catggggcca aggaggtgtc | 360 |
| actaagctat tcaactggtg cacttgcaag ttgcatgggc ctcatataca acaggatggg | 420 |
| aacagtgacc acagaagctg ctttcggtct agtttgtgcc acttgtgaac agattgctga | 480 |
| ttcacagcat cggtctcaca gacaaatggc tactaccaca aatccactaa tcaggcatga | 540 |
| aaacagaatg gtgctggcta gcactacggc aaaggctatg aacaggtgg ctggatcgag | 600 |
| tgaacaggca gcggaggcca tggaggttgc taataagact aggcagatgg tacatgcaat | 660 |
| gagaactatt gggactcatc ctagctccag tgctggtctg agagatgacc ttcttgaaaa | 720 |
| tttgcaggcc taccagaagc ggatgggagt gcagatgcag cggttcaagt gatcctctcg | 780 |

```
tcattgcagc aaacatcatt gggatcttgc acctgatatt gtggattact gatcgtcttt    840
ttttcaaatg catttatcgt cgctttaaat acggtctgaa aagagggcct tctacggaag    900
gagtgcctga gtccatgagg gaagaatatc aacaggagca gcagagtgct gtggatgttg    960
acgatggtca ttttgtcaac atagagctag agtaaaaaac ta                      1002
```